United States Patent [19]

Stembridge et al.

[11] Patent Number: 4,780,861
[45] Date of Patent: Oct. 25, 1988

[54] AUTOMATIC CONTROL SYSTEM FOR FILLING BEVERAGE CONTAINERS

[75] Inventors: William F. Stembridge, College Park, Ga.; James C. Sturrock, Espanola, N. Mex.; W. Frank Stembridge, III, East Point, Ga.

[73] Assignee: The Coca-Cola Company, Atlanta, Ga.

[21] Appl. No.: 12,758

[22] Filed: Feb. 9, 1987

Related U.S. Application Data

[60] Division of Ser. No. 684,215, Dec. 20, 1984, which is a continuation-in-part of Ser. No. 629,397, Jul. 10, 1984, abandoned.

[51] Int. Cl.$^4$ .......................... H04R 17/00; B65B 1/30
[52] U.S. Cl. .................... 367/150; 367/162; 367/165; 367/176; 367/908; 73/624; 73/290 V; 181/124; 141/95
[58] Field of Search ................ 73/622, 623, 624, 628, 73/642, 644, 290 A, 294, 298; 141/94, 95, 83, 198, 367, 368, 369, 370, 371, 372; 222/1; 181/108, 110, 123, 124, 196, 198, 256, 400, 402; 367/87, 140, 141, 150, 151, 155, 157, 162, 165, 173, 176, 908, 909; 340/901, 904; 310/326, 327, 334, 335, 337, 345, 348, 358

[56] References Cited

U.S. PATENT DOCUMENTS

| | | | |
|---|---|---|---|
| 1,149,256 | 8/1915 | Godfrey | 73/290 V |
| 2,938,551 | 5/1960 | Hallstein | 73/290 |
| 2,960,678 | 11/1960 | Beard et al. | 73/290 V |
| 3,184,969 | 5/1965 | Bolton | 73/290 V |
| 3,223,964 | 12/1965 | Stadlin | 73/290 V |
| 3,486,377 | 12/1969 | Franchi | 73/290 V |
| 3,603,149 | 9/1971 | McKown | 73/290 V |
| 3,640,122 | 2/1972 | Nusbickel, Jr. | 73/67.9 |
| 3,791,199 | 2/1974 | Toth et al. | 73/67.9 |
| 3,814,146 | 6/1974 | Mesh | 141/1 |
| 3,823,846 | 7/1974 | Probst | 222/70 |
| 3,847,016 | 11/1974 | Ziedonis | 73/71.5 V |
| 3,910,116 | 10/1975 | Smith | 73/290 |
| 3,916,963 | 11/1975 | McIntosh | 141/198 |
| 3,985,030 | 10/1976 | Charlton | 73/290 V |
| 4,000,650 | 1/1977 | Snyder | 73/290 V |
| 4,004,266 | 1/1977 | Cook et al. | 367/162 X |
| 4,065,960 | 1/1978 | Grabendorfer et al. | 73/627 |
| 4,083,387 | 4/1978 | Stieber et al. | 141/95 |
| 4,114,441 | 9/1978 | Magri | 73/290 V |
| 4,121,094 | 10/1978 | DiVito et al. | 255/92 FL |
| 4,145,914 | 3/1979 | Newman | 73/290 V |
| 4,170,143 | 10/1979 | Ries et al. | 73/609 |
| 4,170,765 | 10/1979 | Austin et al. | 73/290 V |
| 4,183,007 | 1/1980 | Baird | 367/119 |
| 4,221,004 | 9/1980 | Combs et al. | 367/114 |
| 4,236,553 | 12/1980 | Reichenberger | 141/198 |
| 4,359,055 | 11/1982 | Carlson | 128/660 |
| 4,437,497 | 3/1984 | Enander | 141/1 |
| 4,437,499 | 3/1984 | Devale | 141/1 |
| 4,458,735 | 7/1984 | Houman | 141/95 |
| 4,469,150 | 9/1984 | Grimaldi | 141/195 |
| 4,488,271 | 12/1984 | Held et al. | 367/151 |
| 4,559,979 | 12/1985 | Koblasz et al. | 141/9 |
| 4,572,253 | 2/1986 | Farmer et al. | 141/95 |

FOREIGN PATENT DOCUMENTS

| | | |
|---|---|---|
| 0075492 | 3/1983 | European Pat. Off. |
| 0021953 | 2/1978 | Japan ................ 367/140 |
| 1494699 | 10/1974 | United Kingdom. |
| 1587617 | 3/1977 | United Kingdom. |
| 1600079 | 5/1978 | United Kingdom. |
| 20151296 | 2/1979 | United Kingdom. |
| 2099791 | 5/1982 | United Kingdom. |

*Primary Examiner*—Deborah L. Kyle
*Assistant Examiner*—Brian J. Steinberger

[57] ABSTRACT

An automatic, ultrasonic system for controlling the filling of different sizes of beverage containers which may or may not contain various quantities of ice. The system includes a transducer assembly and a control module, both preferably connected to a beverage dispenser valve assembly. The transducer assembly includes a pair of piezo-electric crystals for separately transmitting and receiving ultrasonic wave energy from the grate, the cup lip, the top of any ice in the cup, and the rising liquid level. The control module includes a microcomputer and associated circuitry.

8 Claims, 59 Drawing Sheets

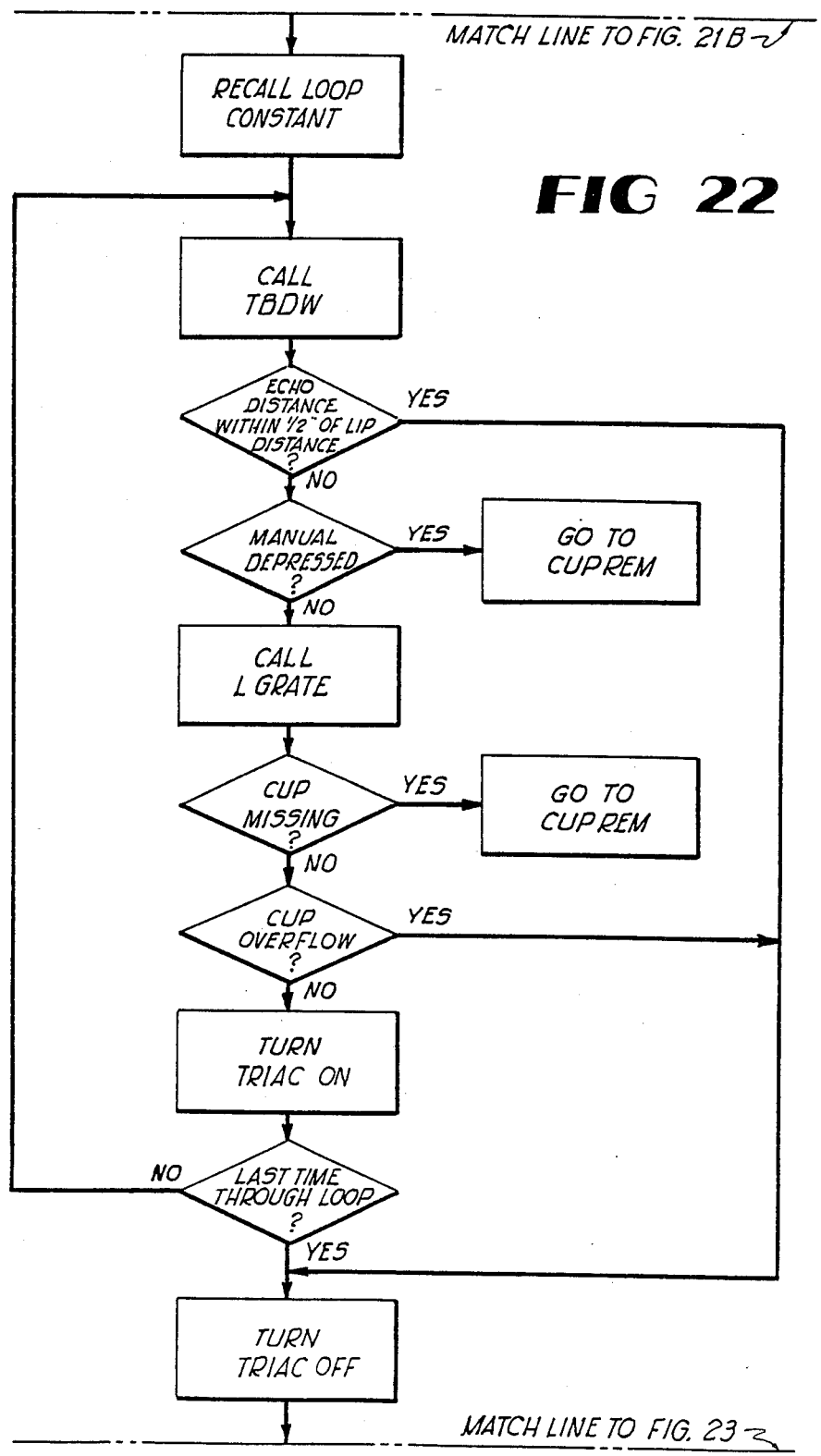

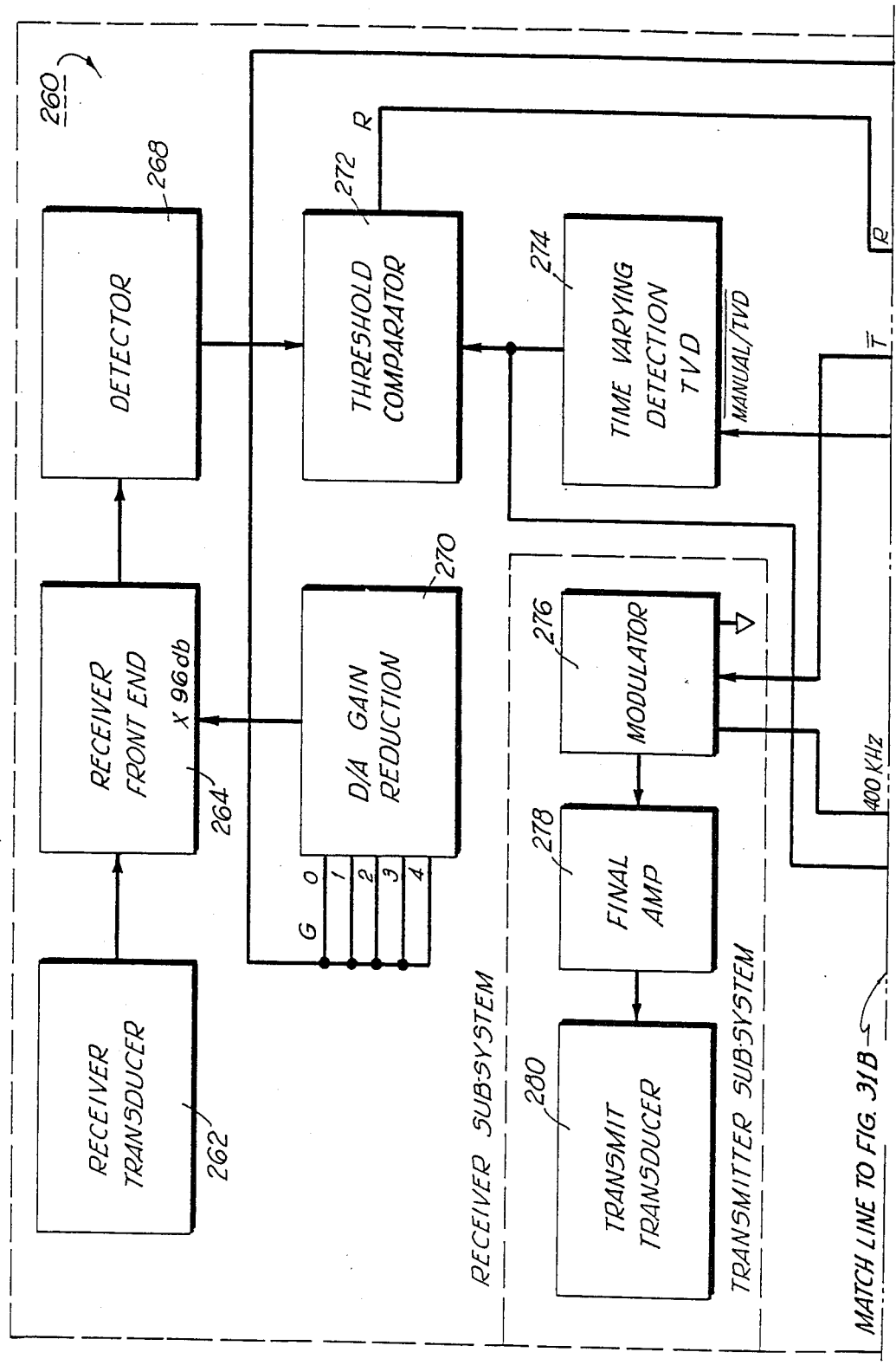

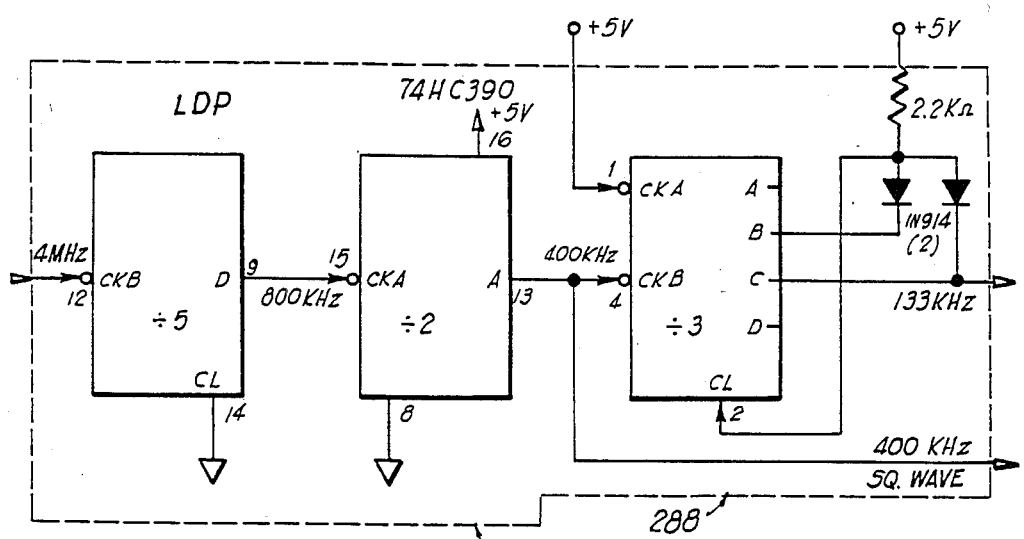
FIG 37
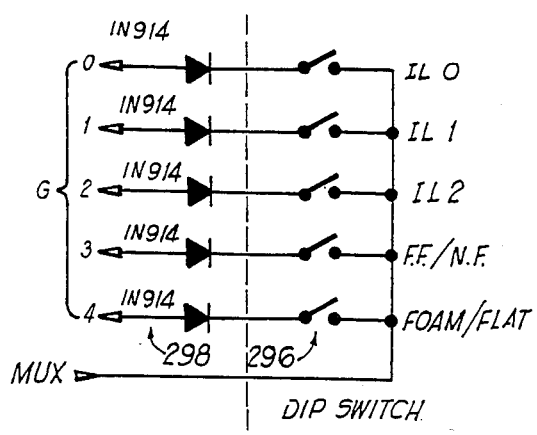
FIG 38A  FIG 38B
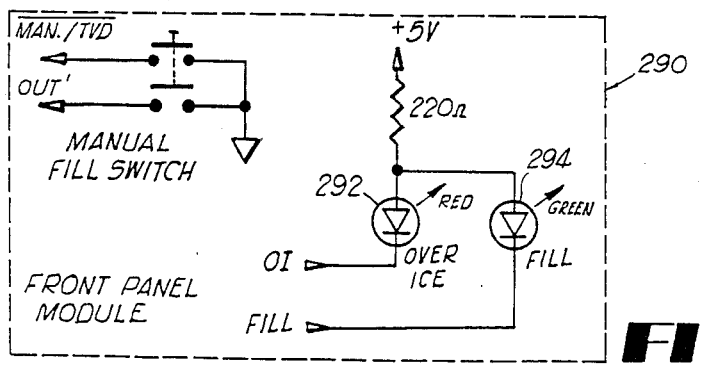
FIG 39

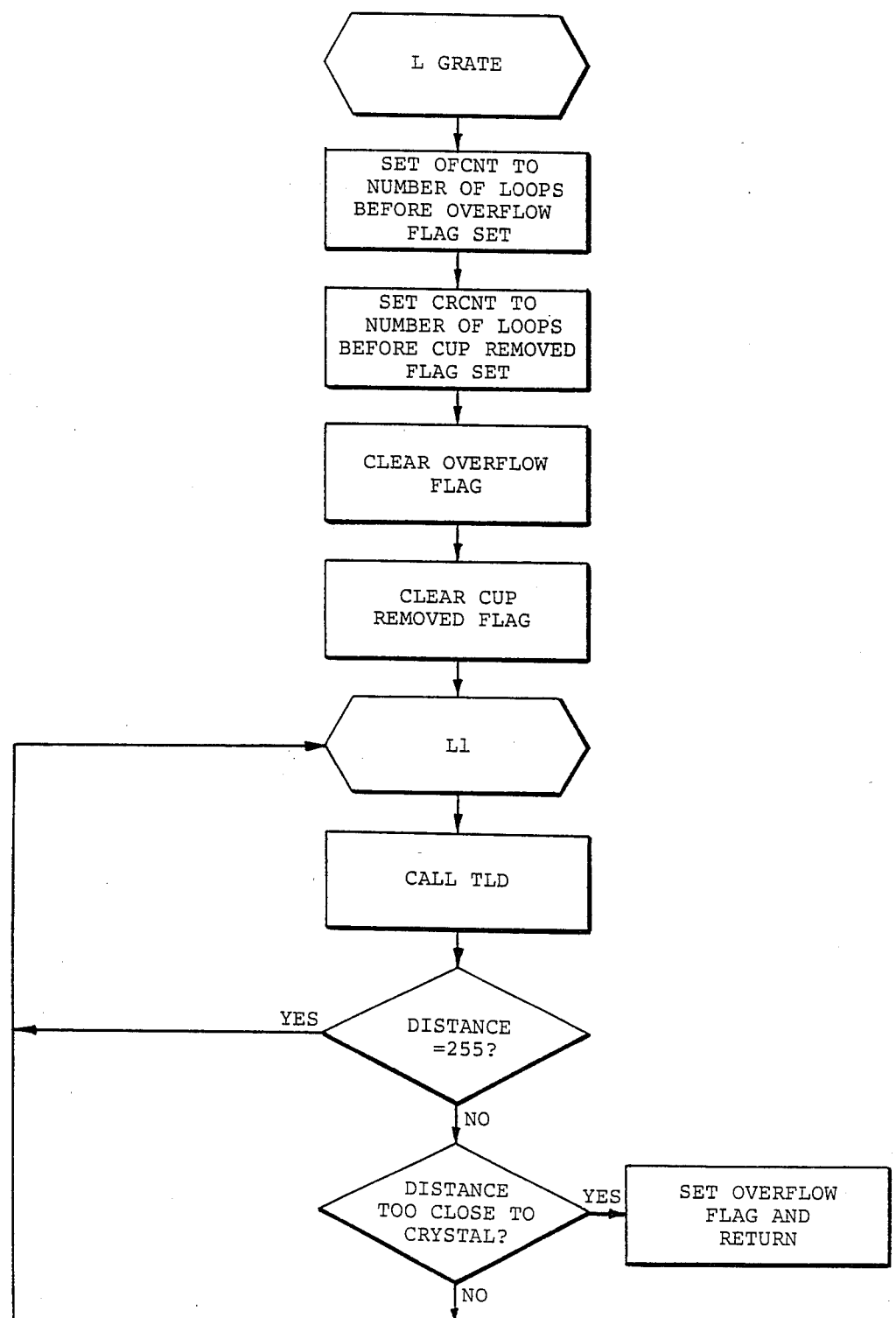
FIG 43A  MATCH LINE TO FIG. 43B

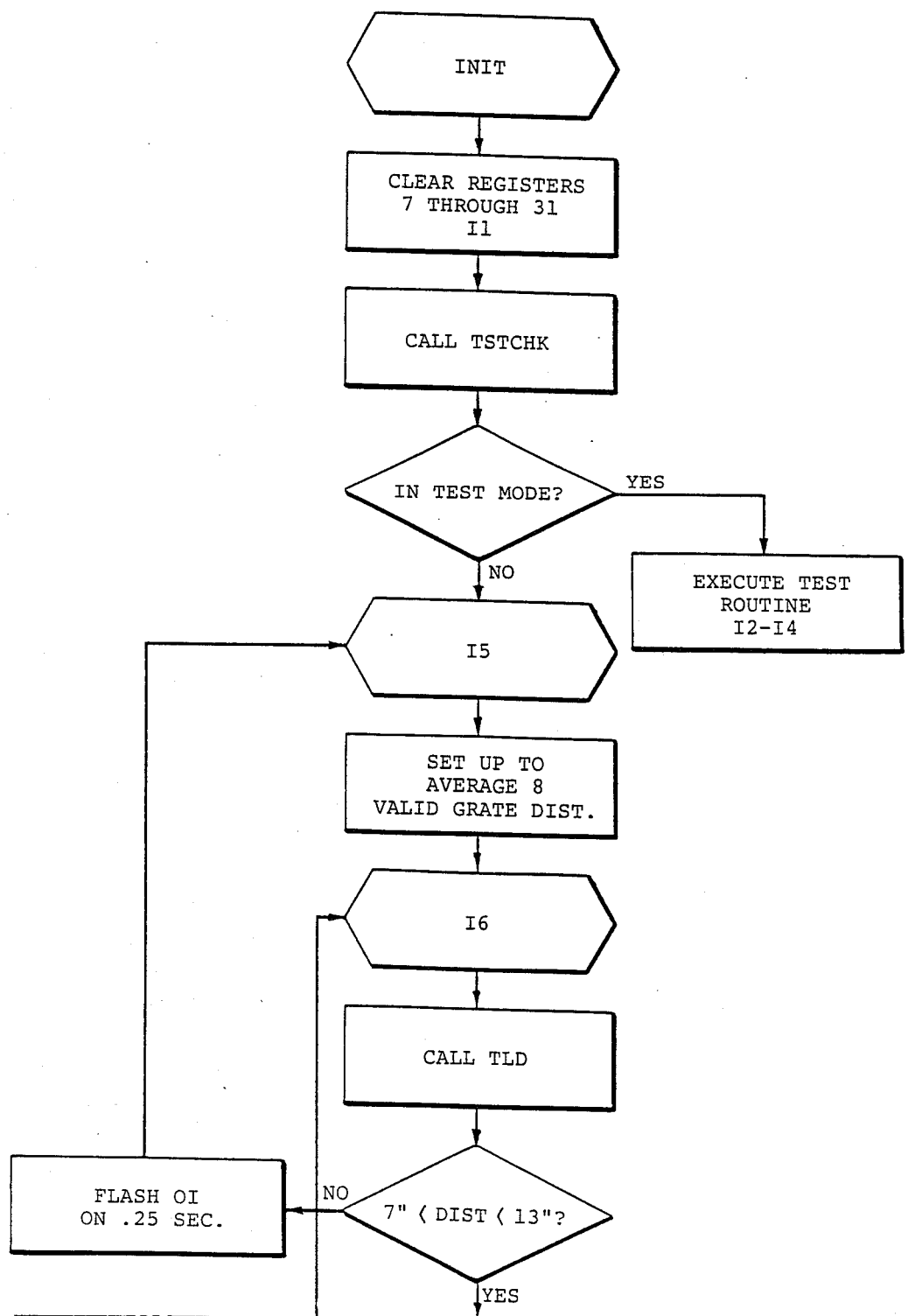
FIG 45A  MATCH LINE TO FIG. 45B

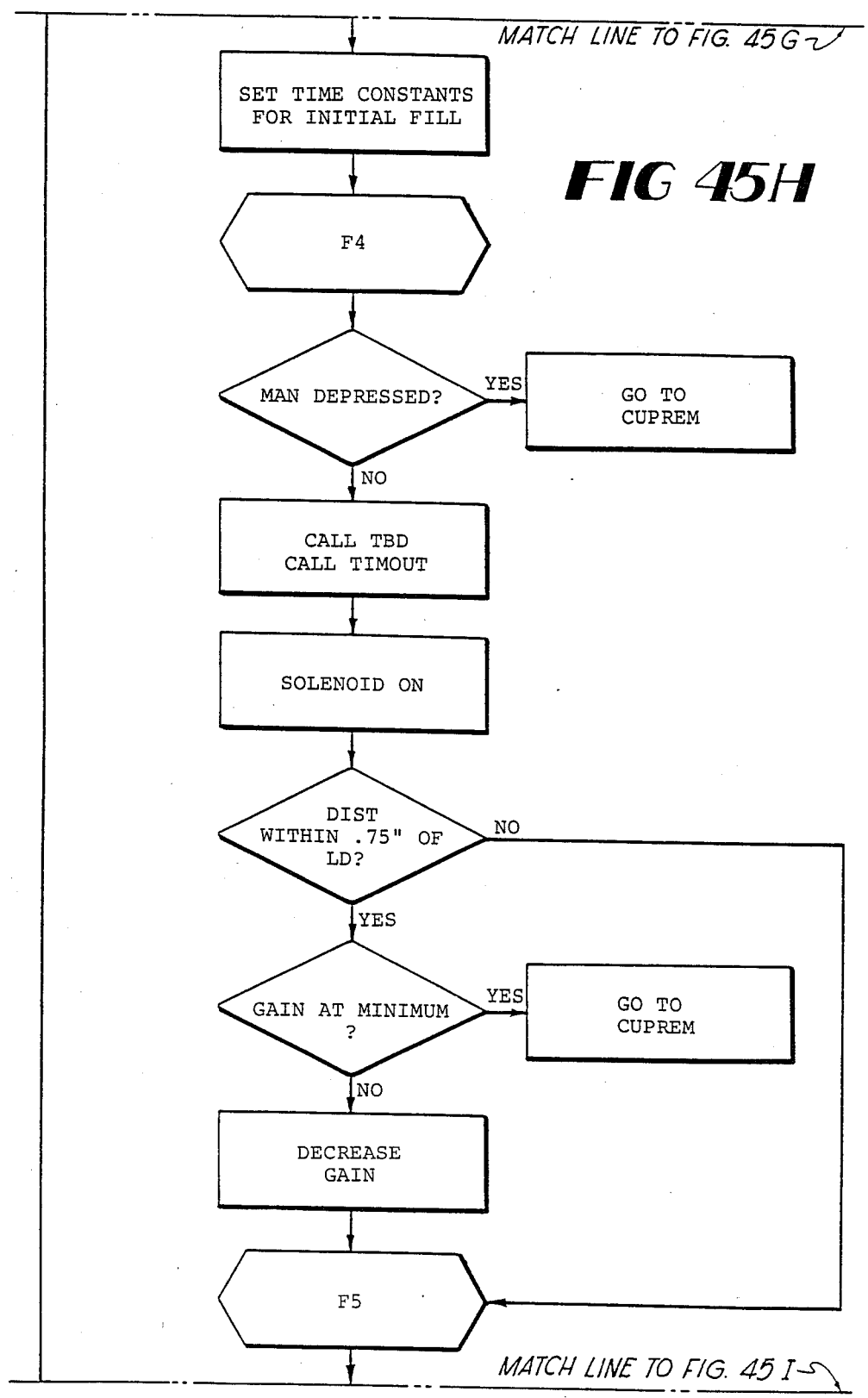

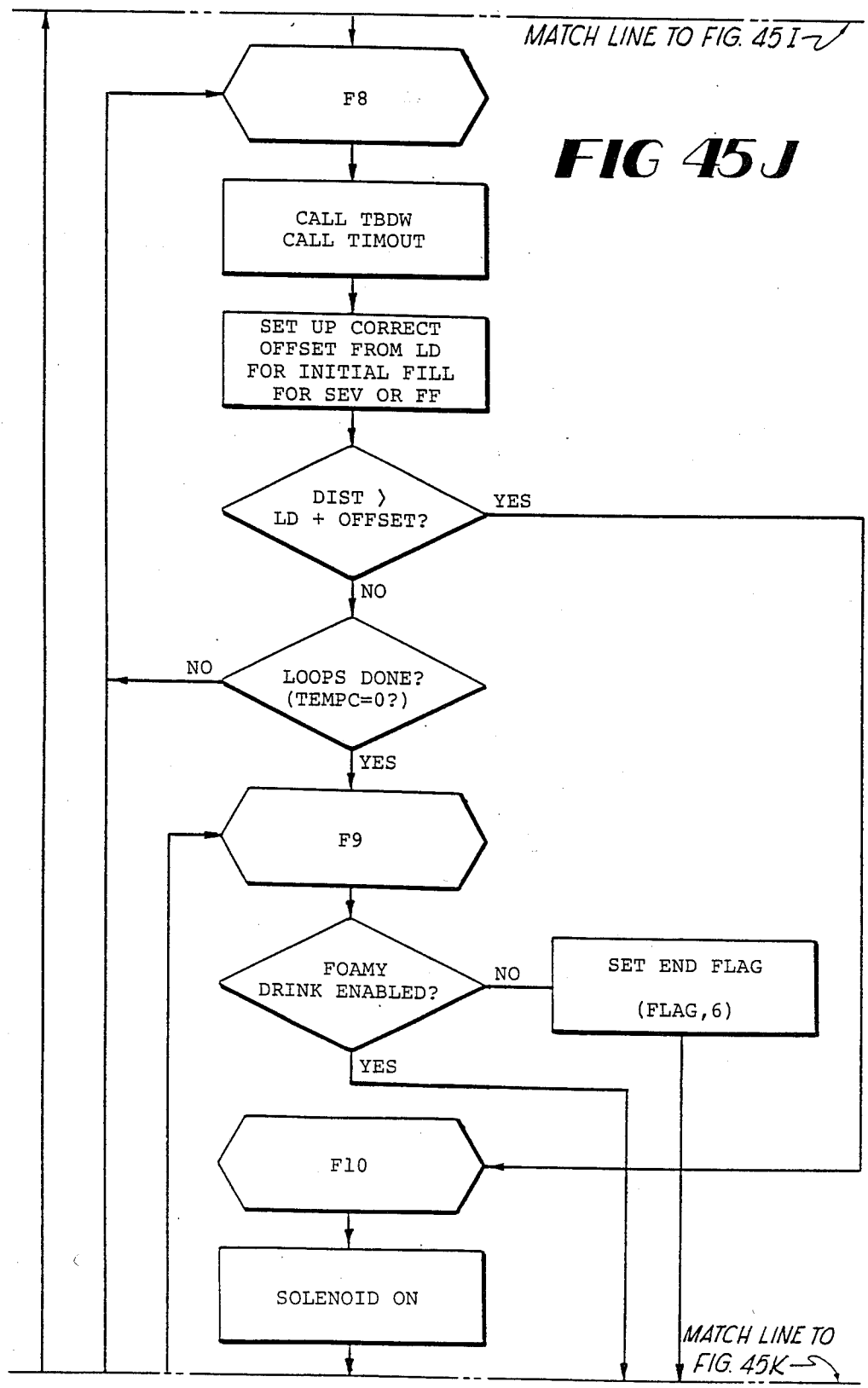

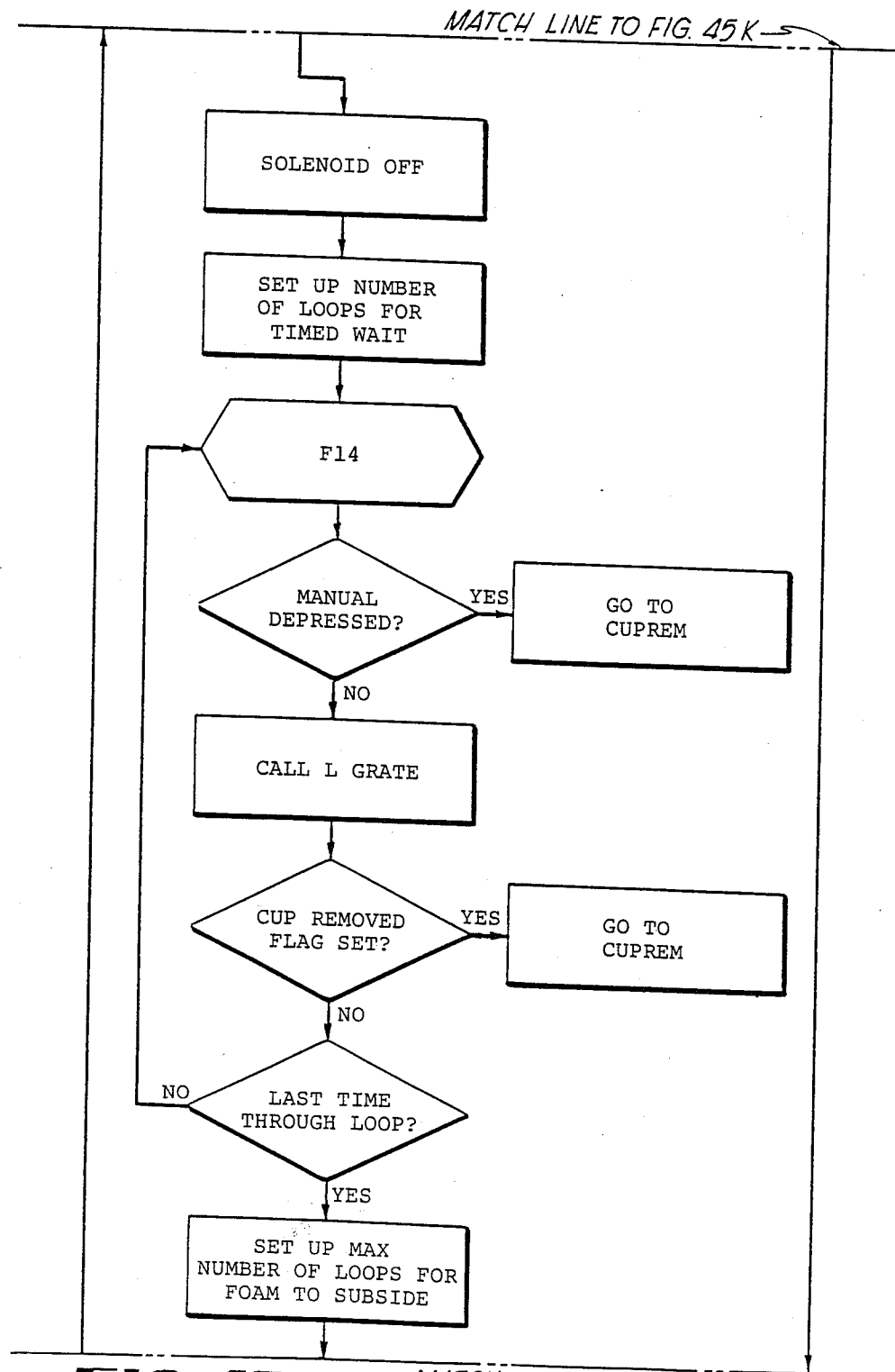

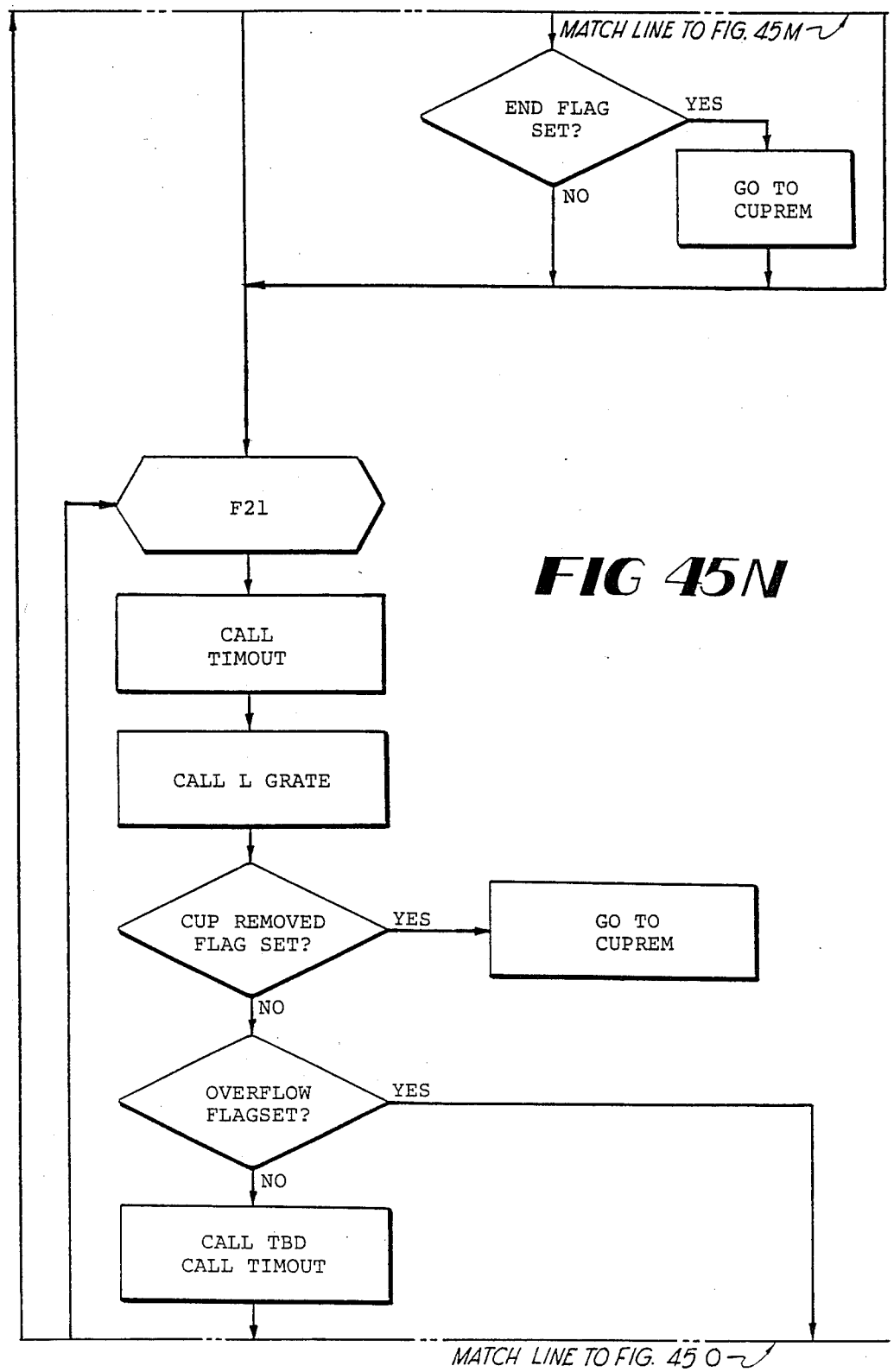

AUTOMATIC CONTROL SYSTEM FOR FILLING BEVERAGE CONTAINERS

CROSS-REFERENCE TO RELATED APPLICATION

This application is a divisional of prior application Ser. No. 684,215, filed Dec. 20, 1984 and entitled Automatic Control System for Filling Beverage Containers which is, in turn, a continuation-in-part of prior application Ser. No. 629,397, filed July 10, 1984 and entitled Ultrasonic System for Automatically Filling Beverage Cups, now abandoned.

BACKGROUND OF THE INVENTION

1. Field of the Invention

This invention relates to beverage dispensing and more particularly to an ultrasonic system for automatically controlling the filling of beverage containers, such as with post-mix carbonated soft drinks.

2. Description of the Prior Art

Heretofore, attempts have been made to provide apparatus to automatically fill beverage containers, such as cups, in response to the proper positioning of a cup under a nozzle of a dispensing valve assembly of a beverage dispenser. Such apparatus used, for example, liquid level detectors such as either conductive or capacitive electrical probes to measure the liquid level.

It is also known to measure various liquid levels within containers using ultrasonic energy and associated circuitry.

SUMMARY OF THE INVENTION

An automatic system for controlling the filling of different sizes of beverage containers or cups, which cups may contain various quantities of ice, with a beverage which may or may not foam during filling. The system includes a transducer assembly and a control module, both preferably connected to a beverage dispenser valve assembly. The transducer assembly is mounted adjacent to the nozzle and uses a first crystal to transmit ultrasonic energy (ultrasound wave energy) and a second crystal to receive reflected ultrasonic energy. Both crystals have lenses for providing coupling of the beam between the crystal and the air, and for either producing a shaped beam (the transmitter crystal) or for receiving a beam from a defined area (the receiver crystal). The control module includes a microcomputer and associated circuitry for controlling the filling operation, including determining that a cup is present below the nozzle of the valve assembly, determining that the cup does not have too much ice, filling the cup, waiting for any foaming to subside, topping off the cup to completely fill it, and producing a signal to an operator that the filling is completed.

It is an object of the present invention to provide a system to automatically control the filling of beverage cups.

It is another object to provide a bi-static ultrasonic system to automatically fill beverage cups.

It is a further object to provide such a system that employs signals received from the grate, the cup lip, and the liquid level in the cup.

It is another object to provide a high resolution bi-static ultrasonic filling system in which the container and liquid level are in air and are very close to the crystals.

It is another object to provide such an ultrasonic system in which the receiver gain is maintained at a constant gain during each transmission period for the separate receiver crystal, but the detection level or scheme is changed; in particular the detection scheme is turned down very low until the transmitted beam is about one-half inch below the nozzle, and then the detection scheme is turned on at a constant ramp to compensate for signal loss.

It is still another object to lens the crystals using ABS or polycarbonate plastic.

It is another object of the present invention to provide an ultrasonic system for automatically controlling the filling of a beverage cup, which system: (1) uses a frequency of about 400 KHz, (2) uses a bi-static transducer system, (3) looks at the leading edge of the reflected ultrasonic energy pulses rather than at the trailing edge, (4) makes the cup lip during certain routines, (5) lenses the transducer, (6) uses a lens material that both shapes the ultrasonic beam and also couples it to the air, (7) uses a timed fill for the initial fill because of cup vibration and therefore lip vibration, (8) uses a low gain to see the liquid level (which is a better reflector than the lip) but not the lip during certain parts of the routine, (9) looks above the lip (the LGRATE subroutine) and shut off the filling if a signal above the lip (showing overfilling) is received, and (10) measures the filling time and shuts off the filling if the fill time exceeds a maximum time period (to prevent continued filling of a cup with a hole in it, for example).

It is another object of the present invention to provide a system for use on adjacent beverage dispensing valve assemblies to automatically control the filling of beverage cups from such valve assemblies without interference therebetween.

It is a still further object of the present invention to allow placement of ultrasonically controlled valve assemblies in close proximity to each other without interference therebetween.

It is a further object of this invention to prevent unwanted interference from adjacent ultrasonically controlled valve assemblies by synchronizing the operation of adjacent valve assemblies to different half cycles of the a.c. power supply.

BRIEF DESCRIPTION OF THE DRAWINGS

The present invention will be more fully understood from the detailed description below when read in connection with the accompanying drawings wherein like reference numerals refer to like elements and wherein:

FIGS. 14–26 are flow charts illustrating the main routine and the sub-routines of the software for operating the microcomputer 66 in the block diagram of FIG. 4;

FIGS. 31A and 31B are a master block diagram of the automatic control system of the preferred embodiment of the present invention;

FIG. 37 is a schematic circuit diagram of the frequency divider of FIG. 31;

FIG. 38A is a schematic circuit diagram of the dip switch of FIG. 31 and FIG. 38B is a table showing how to set the switches for a desired ice level;

FIG. 39 is a schematic circuit diagram of the front panel module with the manual fill switch and the over-ice and filling indicator lights.

DETAILED DESCRIPTION OF THE PREFERRED EMBODIMENTS

With reference now to the drawings, a first embodiment of the present invention will first be described with reference to FIGS. 1–26, and then a second embodiment will be described with reference to FIGS. 27–46.

Figure 1:
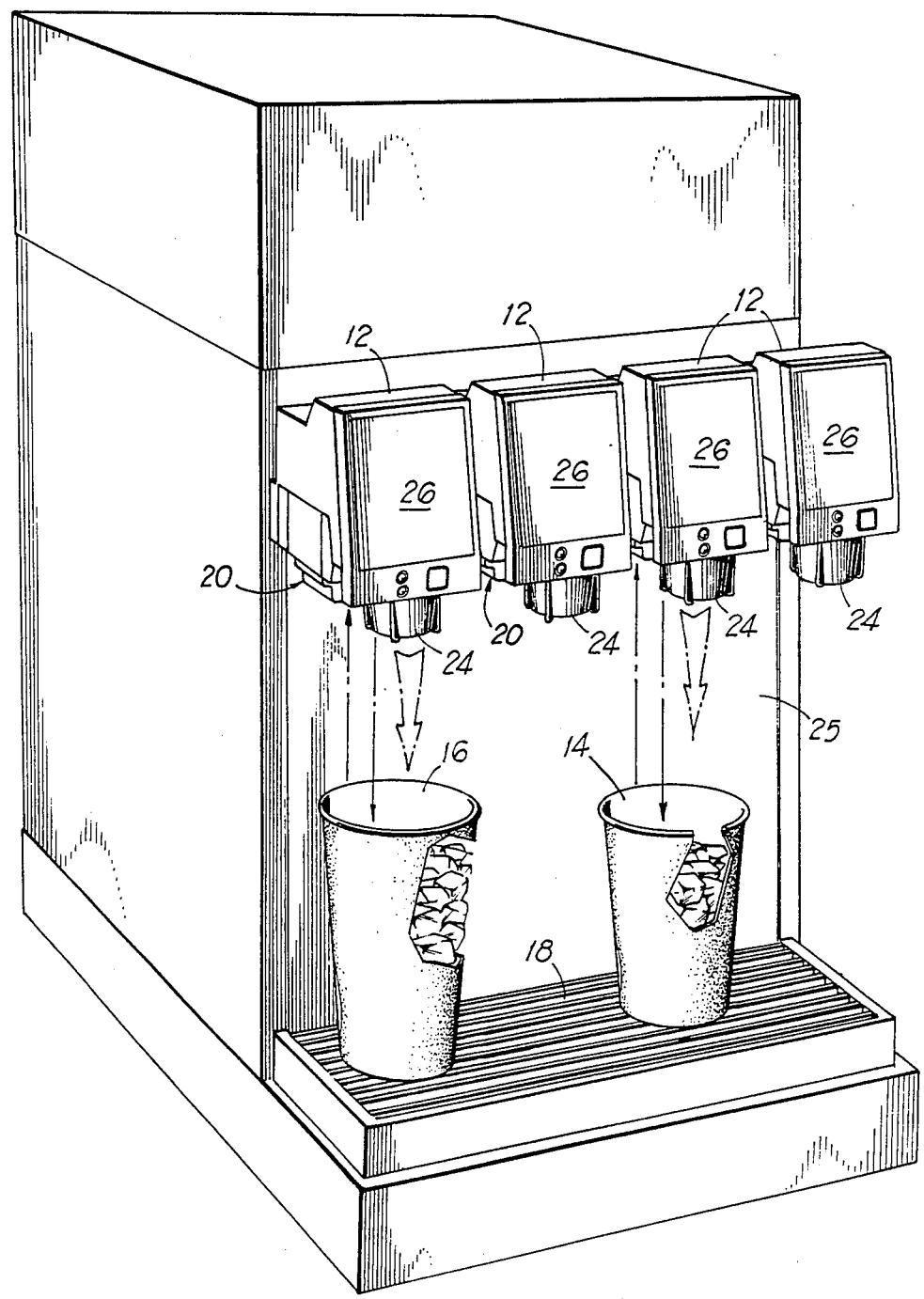
FIG. 1 is a perspective view of a beverage dispenser having four valve assemblies each using the automatic filling system of the present invention.

FIG. 1 shows a post-mix beverage dispenser 10 having four identical beverage dispensing valve assemblies 12, each of which has been modified to include the automatic filling apparatus of one embodiment of the present invention in place of the usual cup actuated mechanical lever that normally extends below each valve assembly 12 for operating the two solenoids of the valve assembly (one being for syrup and one for carbonated water). Each of the valve assemblies 12 is used for dispensing soft drink beverages (usually a different beverage from each valve assembly) into various sizes of cups 14 and 16, supported on a cup supporting surface or grate 18. One particular beverage dispenser 10 and one particular valve assembly 12 is shown, however, any valve assemblies and any beverage dispenser can be used. Beverage dispensers and beverage dispensing valve assemblies, such as those shown at 10 and 12 respectively in FIG. 1, are well-known and thus no detailed description thereof is needed.

Figure 2:
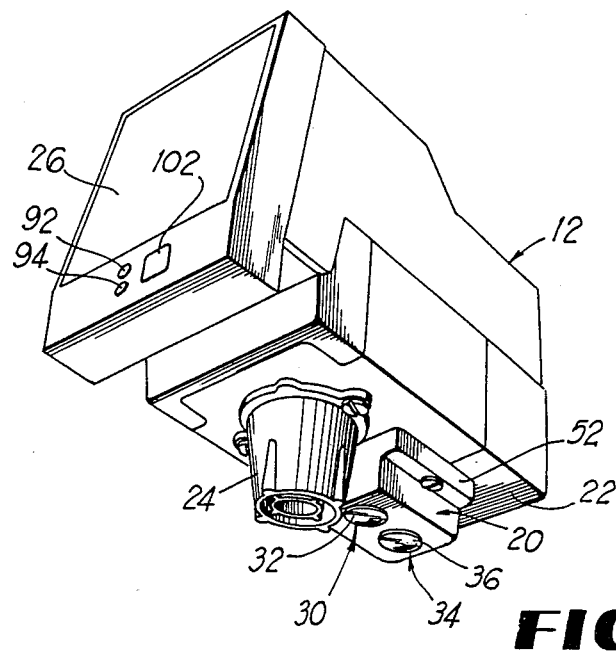
FIG. 2 is a perspective view of one of the valve assemblies of FIG. 1.

With reference to FIGS. 1 and 2, the automatic filling apparatus of the first embodiment of the present invention includes a transducer assembly 20 located on the bottom surface 22 of the valve assembly 12 and behind the nozzle 24, and a control module 26 attached to the front of the valve assembly 12.

Figure 3:
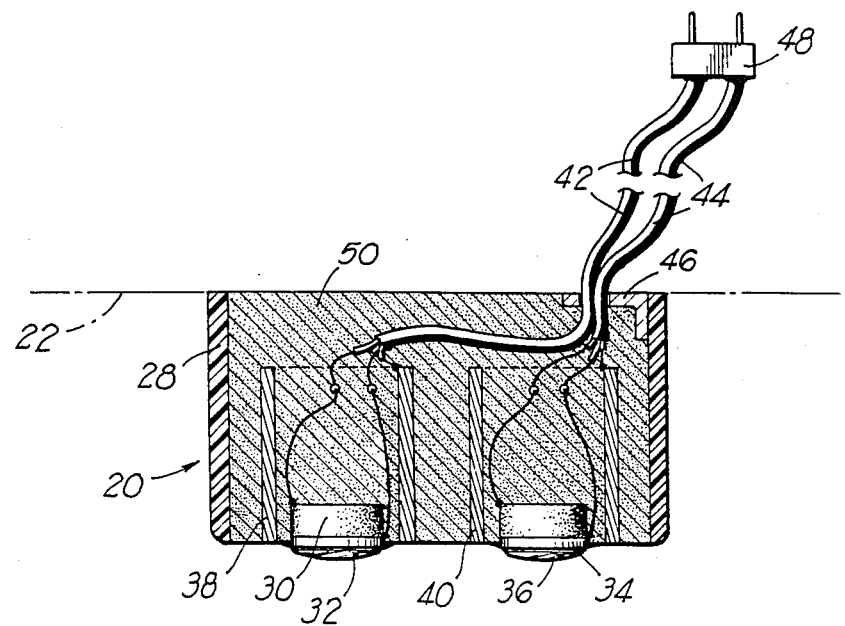
FIG. 3 is a cross-sectional side view of the transducer assembly shown in FIG. 2.

The transducer assembly 20 is best shown in FIG. 3 and includes a plastic housing 28 in which is contained a transmitter crystal 30 having a plastic lens 32, and a receiver crystal 34 having a plastic lens 36. The transmitter and receiver crystals are located inside of brass tubes 38 and 40, respectively. A pair of shielded cables 42 and 44 are connected by a clamp 46 to the housing 28. Each cable has a shield wire connected to a respective one of the brass tubes and also a pair of wires connected to a respective one of the crystals at opposite locations thereon, as shown in FIG. 3. Each of the crystals has a metal plating on each of its upper and lower surfaces. The wire connections to the crystals include a pair of 34 gauge wires soldered one each to one of the metal platings on the crystal and then in turn soldered to two 22 gauge wires in the cables 42 and 44. The cables 42 and 44 are about six inches long and terminate in a single MTA connector 48, for connection to the control module 26. All of the space within the housing 28 is filled with urethane foam 50.

The crystals 30 and 34 are preferably PZT-4 ceramic crystals (a generic trade designation for a particular crystal material), which are a combination of lead titanate and lead zirconate. Each of the crystals 30 and 34 is attached to its respective lens 32 and 36 preferably by using about ½ drop of glue such as that sold under the trademark Eastman 910. The plastic lens is preferably made of ABS, polycarbonate, acrylic or polystyrene plastic.

The plastic housing 28 has a pair of flanges (flange 52 is shown in FIG. 2) each having a screw hole for attaching the transducer assembly 20 to the valve assembly 12.

The brass tubes 38 and 40 have the functions of electrically shielding or isolating the crystals, of sound isolating the crystals, and of mechanically holding the crystals (along with the urethane foam which is poured into a mold or fixture used to hold all of the elements of the assembly 20 in place, and which is then allowed to harden).

The selection of the most desirable frequency to use was made as follows. Regarding the upper limit, the attenuation of ultrasonic sound in the air becomes too great to use for more than a few inches at above approximately 600 KHz. In addition, it was desired to avoid the 455 KHz broadcast band IF frequency, and the 550 KHz to 1.65 MHz AM broadcast band. By staying away from FCC assigned frequencies, and by using a transmission that is not too strong in relation to radio stations, interference on radio receivers that are operated in close proximity to the automatic control system of the present invention is precluded.

Regarding the lower limit, because the beam pattern is constricted by the close proximity of other valve assemblies, a 2 inch spread at 14 inches at the 3 db point was assumed for the beam pattern. This 2 inch spread yields an angle of approximately 8 degrees total. Due to the spacing considerations, a ½ inch diameter crystal was selected. A 400 KHz frequency was selected as the preferred frequency. Other frequencies in the range of 200 KHz to 450 KHz could alternatively be used.

Regarding the beam shape, at 14 inches the total maximum beam pattern needs to be less than 3 inches wide at the limits of detectability (−40 db) in the side to side direction, and approximately 3 inches front to back at the −3 db points. The gain at these points would need to be as flat as reasonable. The crystal pattern was chosen empirically as the one giving the best level gain from front to back with the crystals 30 and 34 aligned from front to back between the nozzle 24 and the splash plate 25. The resulting overall gain pattern with a 3 db gain at 12 inches had a resulting spread sideways of 3.5 degrees, and a resulting spread front to rear of 12 degrees.

To achieve the desired beam pattern, it was necessary to lens the crystals. A 2 inch concave radius produced the 8 degrees narrowing from side to side, and a 4 inch convex radius produced the 8 degrees to 12 degrees spreading from front to rear which formed a fan shaped beam pattern with an elongated footprint having a width of approximately ¾ inch and having a length of about 2½ inches at 3 db gain and 12 inches away from the transducer assembly 20. This beam shape footprint has its long dimension extending front to back relative to the dispenser.

Coupling from the crystals 30 and 34 to the air was calculated as follows:

Characteristic impedance of PZT-4 is equal to 66×10E6 rayls (E=exponent throughout the following description).

Transmitted powder is (Tp)

$$Tp = \frac{(N2/N1)}{(N2/N1) + 1} \times Pc$$

N2=The characteristic impedance of air.
N1=The chararacteristic impedance of PZT-4.
Pc=Power output of crystal.
Tp=12.6×10E-6 for 1 watt in, or 0.00126% goes to the air.

If a third material is introduced between the air and the material we get the following equation:

$$Tp = \frac{4(N3/N1)}{((N3/N1) + 1)} \times \frac{(N2/N3)}{((N2/N3) + 1)} \times Pc =$$

$$\frac{4(N2/N1)}{((N2/N1) + 1) + (N2/N3) + (N3/N1)} \times Pc$$

Most materials of interest for the third material have characteristic impedances between 0.1×10E6 to 10×10E6 rayls.

For a 0.1×10E6, Tp=25×10E-6
For 10×10E6, Tp=22×10E-6.

Thus, for any lossless material used as a coupling to air with a characteristic impedance between 0.1×10E6 to 10×10E6 rayls, the resulting input power is at least doubled and the energy transmitted to the air varies by only 10%. The preferred lens material is one of the plastics such as acrylic or ABS. The lens should:
(1) be a plastic for production,
(2) have a ½" diameter and be approximately 0.08 thick,
(3) have a concave radius of 2" in one axis and a convex radius of 4" in the other axis, and
(4) be cemented to the crystal face with about ½ drop of glue (preferably that sold under the trademark Eastman 910, or equivalent).

Regarding the lens mount, to diminish acoustic coupling between the receiver and transmitter, the lenses are mounted in polyurethane foam. A brass tube surrounds each crystal and its inner foam mount which provides electrical shielding and is soldered to the shield of the cable wiring to the crystals. The crystals are left floating, i.e., both electrodes are at a potential not referenced to ground. This gives greater electrical isolation in the receiver since it does not pick up ground referenced noise. The brass tubes are held in place by the polyurethane foam to the desired package shape. The lenses protrude from the bottom surface foam package.

Regarding the crystal shape and material, the transmitter crystal is preferably ½" OD×0.200" for a series resonance of 400 KHz. PZT-4 material was chosen for the crystals 30 and 34 as the best compromise in strength, efficiency, and ease of workability. The receiver crystal is preferably ½" OD×0.190" for a parallel resonance of 400 KHz, and is also made of PZT-4 material.

Regarding the electrical wiring, a twisted shielded pair of 22 gauge stranded wire is used. The wire shielding is soldered to the brass tubes 38 and 40. The brass tubes are isolated from each other electrically. A pair of 34 gauge solid wires is soldered across the metal plated crystal faces and is then soldered to the 22 gauge lead wires. All wiring is foamed in place. The black wire of the twisted pair is attached to the outside crystal face which is marked with a small dot.

Figure 4A:
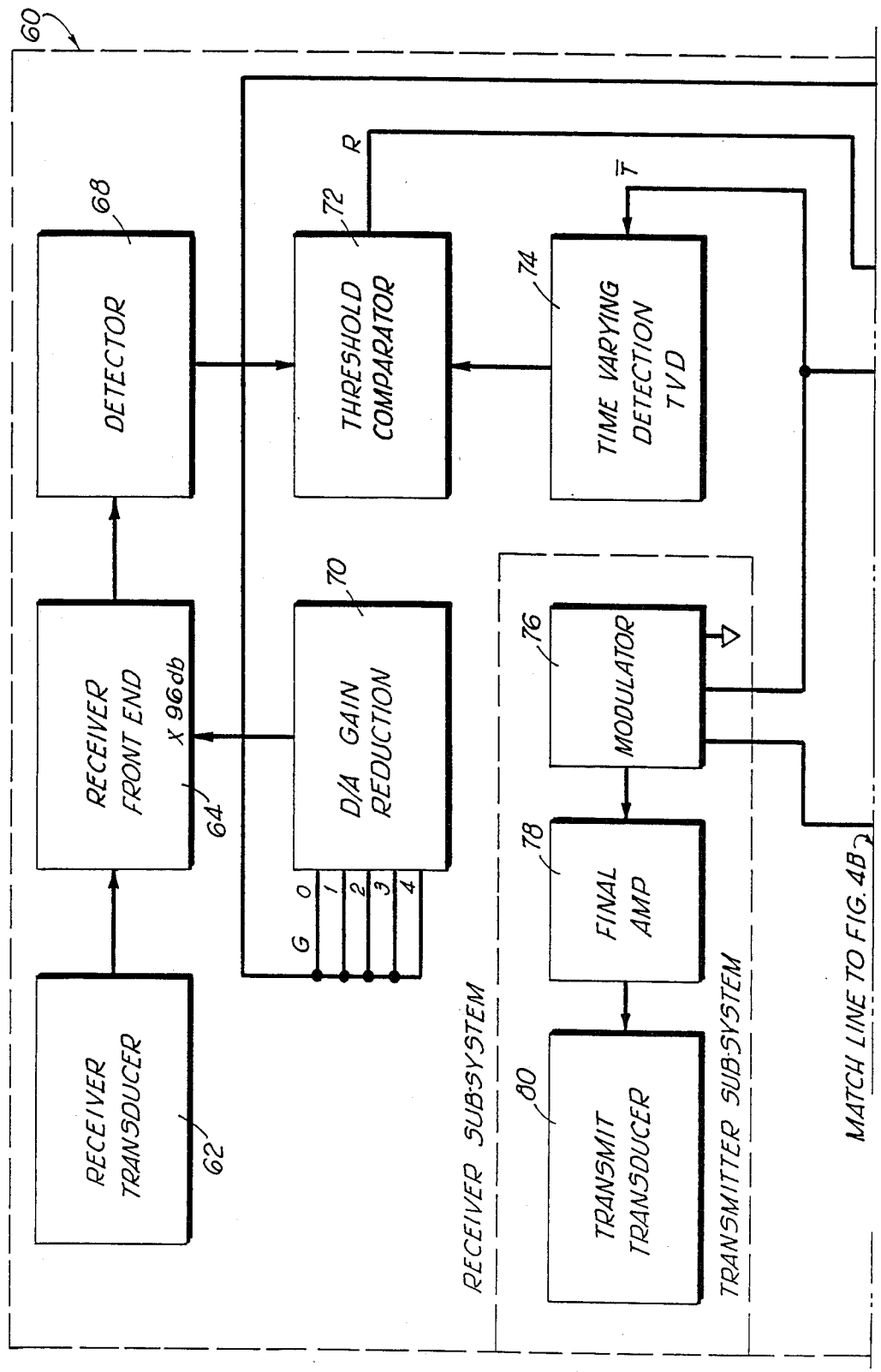
FIGS. 4A and 4B are a master block diagram of the automatic control system of one embodiment of the present invention.
Figure 4B:
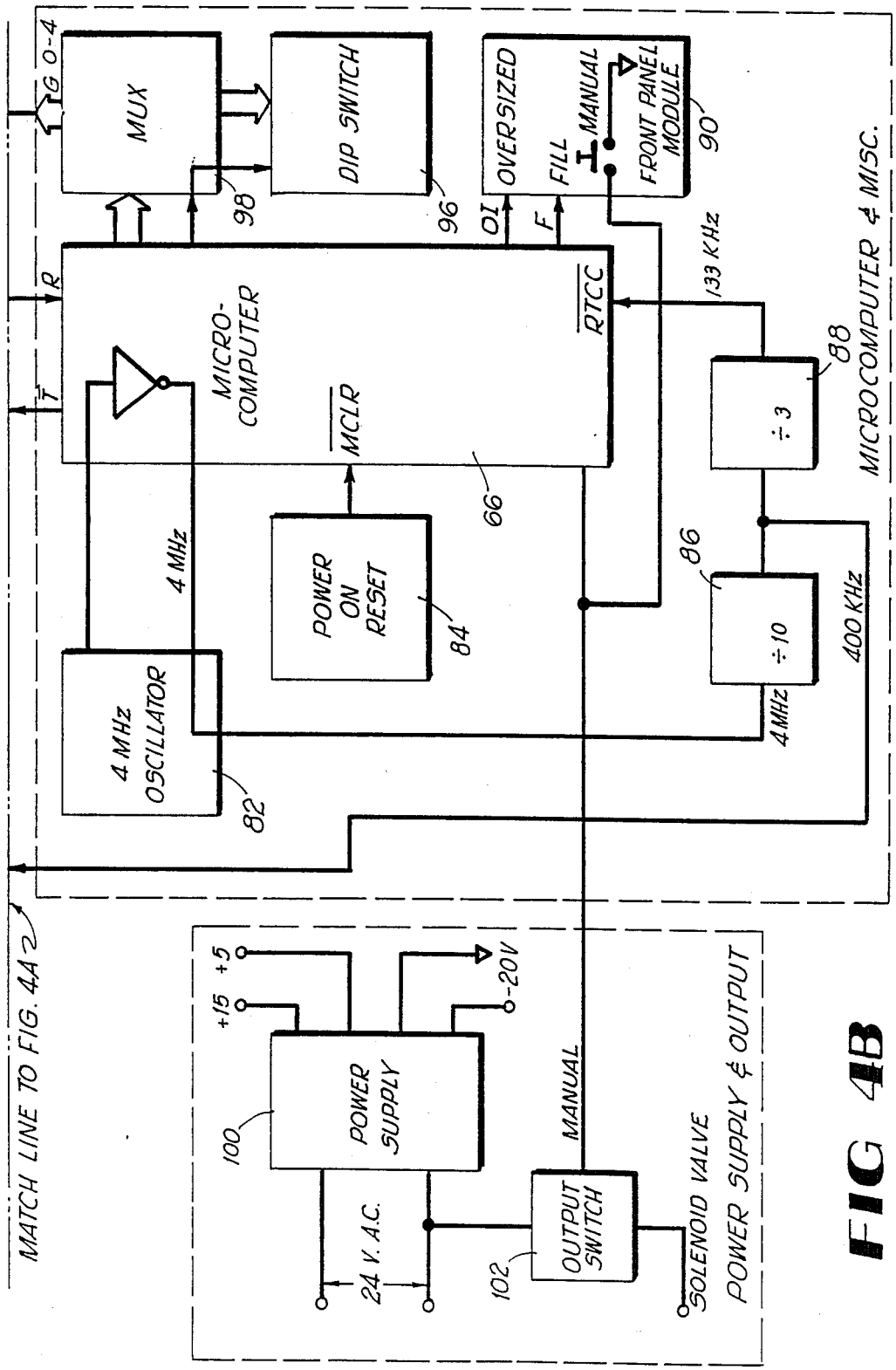
Figure 5:
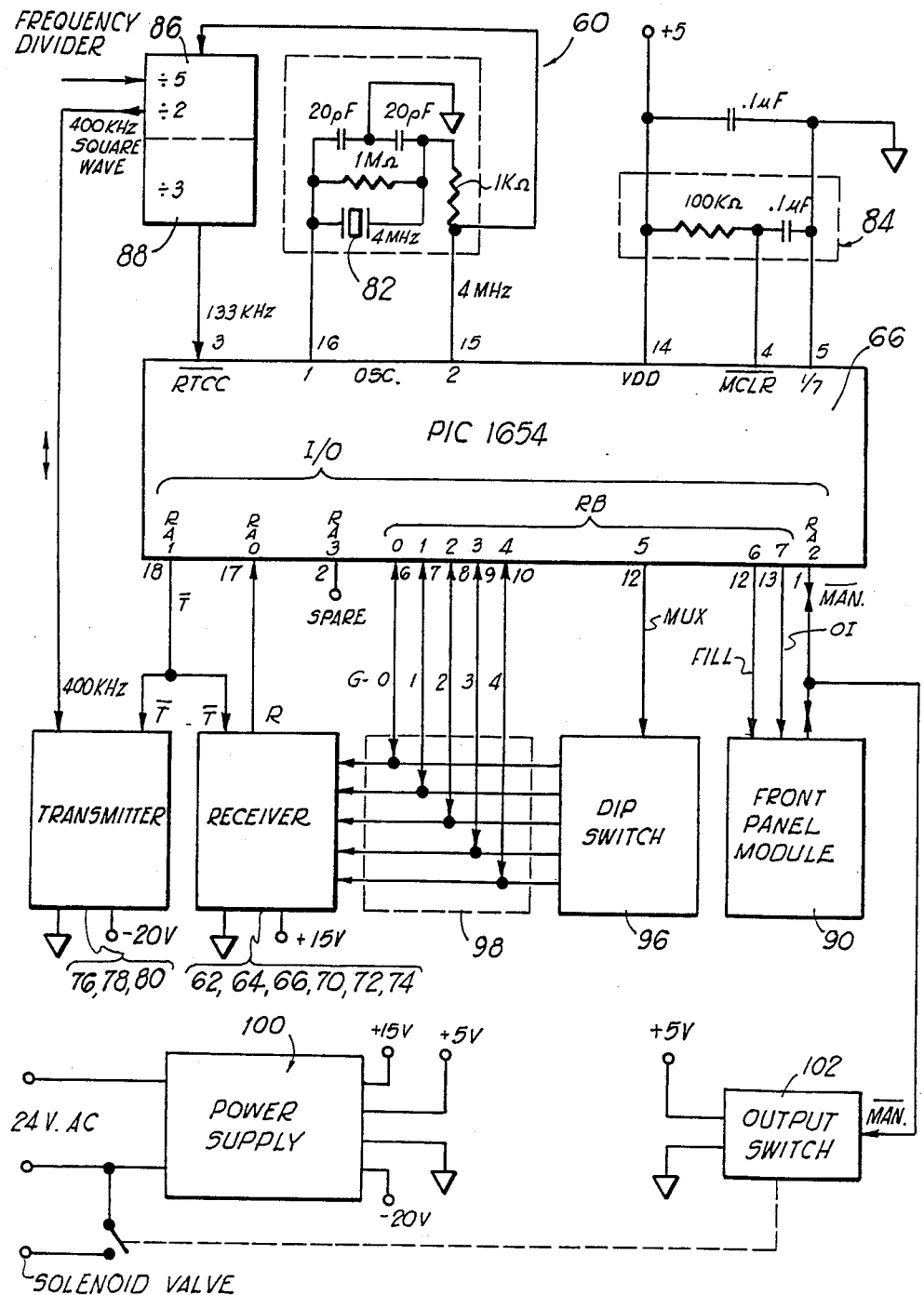
FIG. 5 is a microprocessor block diagram.
Figure 6:
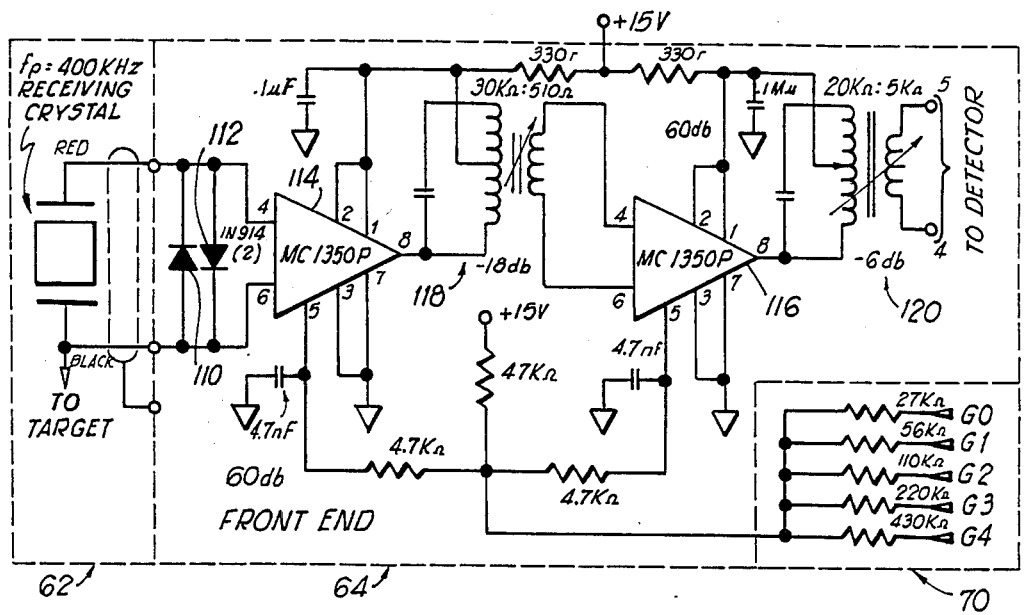
FIG. 6 is a schematic circuit diagram of part of the receiver subassembly including the receiver, the receiver front end, and the D/A gain reduction of FIG. 4.
Figure 7:
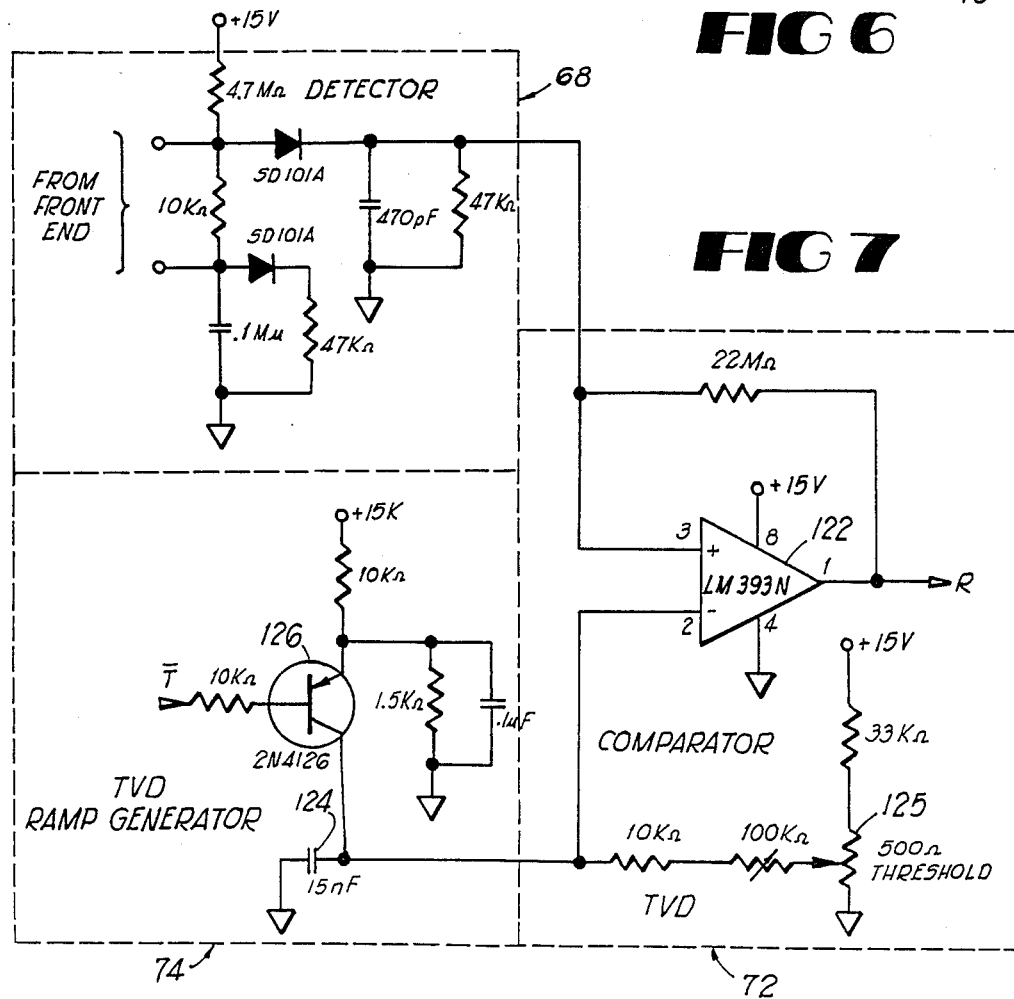
FIG. 7 is a schematic circuit diagram of another part of the receiver subassembly including the detector threshold comparator and the time varying detection generator of FIG. 4.
Figure 8:
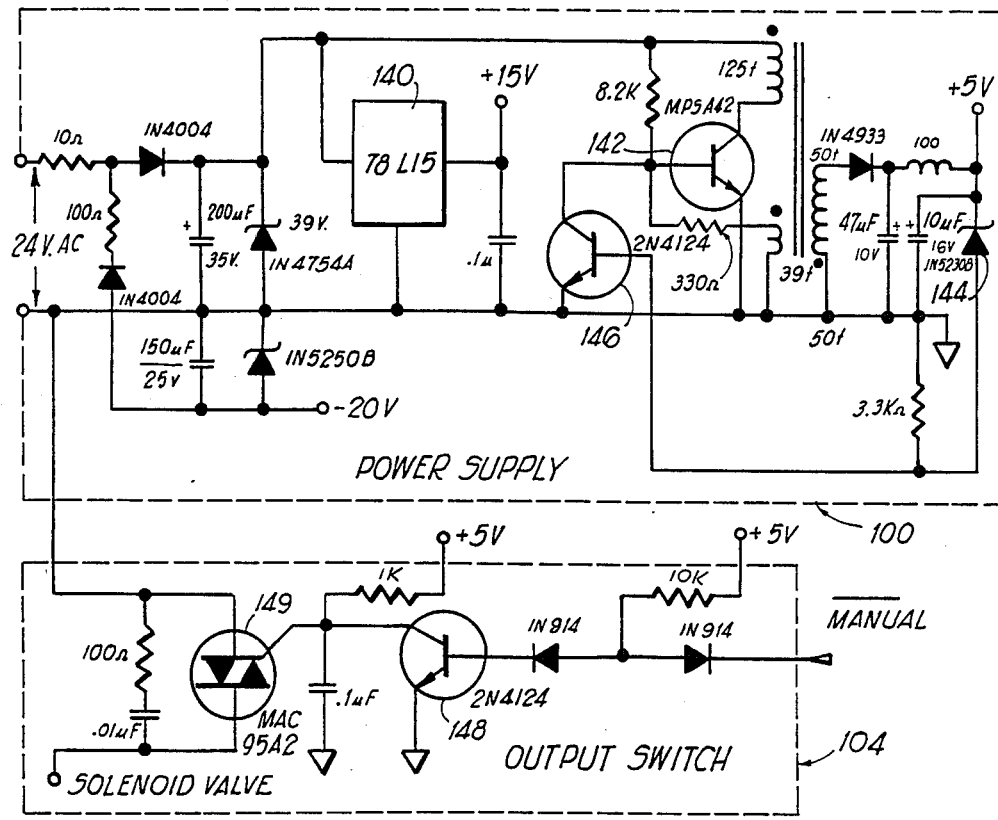
FIG. 8 is a schematic circuit diagram of the power supply and output switch of FIG. 4.
Figure 9:
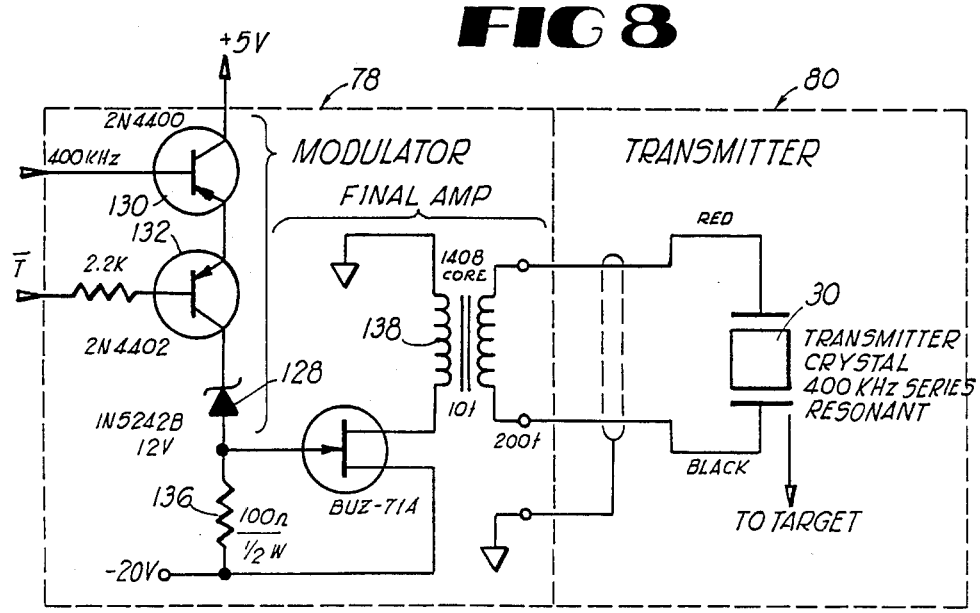
FIG. 9 is a schematic circuit diagram of the transmitter subsystem of FIG. 4.
Figure 10:
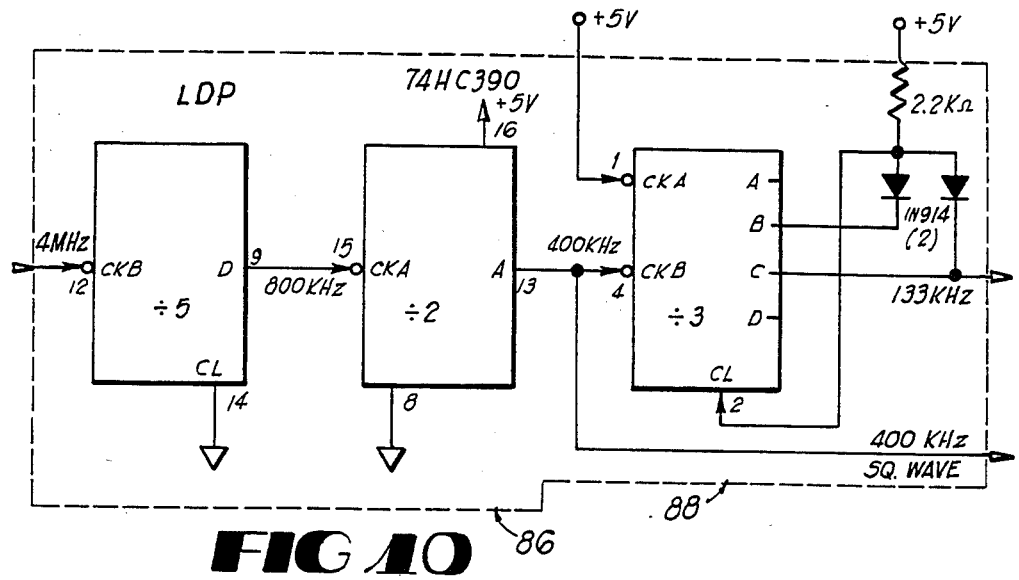
FIG. 10 is a schematic circuit diagram of the frequency divider of FIG. 4.

The control module 26 houses the control circuit board to which the crystals 30 and 34 are connected by the cables 42 and 44 and the connector 48. FIGS. 4A and 4B together provide a master block diagram of the control circuit 60. The control circuit will now be described with reference to FIGS. 4–12.

The receiver transducer 62 (FIGS. 4, 5 and 6) is a 400 Khz, ½ inch diameter parallel resonant piezo-electric crystal 34 made of PZT-4 material. The crystal is coupled to the air by means of a plastic lens 36 which is shaped to receive the beam pattern. The transducer assembly 20 incorporates a brass tube 40 that is ⅝ inch in diameter and is used for electrical isolation. The crystal 34 is mounted such that it is centered in the tube with the lens 36 exposed at one end of the tube. The tube assembly is foamed with polyurethane for acoustic isolation.

The receiver section 64 (FIGS. 4, 5 and 6) has a total gain of 96 db and is comprised of two protective diodes 110 and 112 and two MC1350P IF amplifiers 114 and 116 that are interconnected through a tuned transformer 118 with another tuned transformer 120 to interconnect the second amplifier 116 to the detector 68. These amplifiers 114 and 116 have provisions for gain control fron Pin 5 and are used in this application by the microcomputer 66.

The detector circuit 68 (FIGS. 4, 5 and 7) changes the 400 Khz from the receiver 64 to a DC Analog signal.

This detector is special in that it can not only detect the envelope of the pulse but since it is a DC coupled detector, it has no offset shift due to pulse width variations. By having a balanced detector system, the temperature drift is very low.

The receiver gain reduction 70 (FIGS. 4, 5 and 6) is comprised of five resistors that form a binary weighted current sinking "D to A" converter that is driven by the microcomputer 66, which allows for thirty-two stages of gain level control.

The threshold comparator 72 (FIGS. 4, 5 and 7) is comprised of an LM393N comparator 122 and is used in conjunction with the time varying detection to convert the analog receiver signal to a digital signal which is then fed to the microcomputer 66. Within this circuit is a means for adjusting the slope of the time varying detector using a 100K potentiometer and a means of adjusting the threshold detector using a 500 ohm potentiometer 125.

The time varying detection generator 74 (FIGS. 4, 5, and 7) uses the gate signal that the microcomputer 66 sends to the transmitter, and charges a 15 Nanofarad capacitor 124 to two volts, which sets the peak level of the time varying detector wave form. This circuit is comprised of a 2N4126 switching transistor 126 and the power supply to support that circuit.

The modulator 76 (FIGS. 4, 5, and 9) is comprised of a 12 volt Zener diode 128 and two transistors 130 and 132 that perform an (Anding) function for the transmitter gate signal (T) and the 400 KHz signal from the oscillator. This (Anded) signal is then level shifted through the 12 volt Zener diode 128 and the 2N4402 transistor 132 to the gate of the final amplifier 78.

The final amplifier 78 (FIGS. 4, 5 and 9) is comprised of a BUZ-71A MOS-FET 134, a resistor 136 and a transformer 138. The resistor discharges the gate source capacitor of the MOS-FET 134. The MOS-FET 134 switches the output transformer 138 to the minus 20 volt supply in response to the gate drive signal. The transformer 138 steps the voltage up to the transmitting crystal 30 to approximately 2000 volts.

The transmit transducer 80 (FIGS. 4, 5, and 9) is comprised of a 400 KHz ½ inch diameter series resonant piezo-electric crystal 30 made of PZT-4 material much the same as the receiver crystal 34 with the exception of the thickness. The crystal 30 is coupled to the air by means of a plastic lens 32 which is also shaped to form the beam pattern. The assembly of the transmit transducer 80 is exactly the same as for the receiver as described above.

The microcomputer 66 (FIGS. 4 and 5) is a General Instruments Pic-1654 and contains the intelligence and control functions of the entire system. It communicates to the rest of the system through twelve I/O pins. It also contains the oscillator circuit, the master clear circuit, and the real time clock counter input.

The crystal 82 (FIGS. 4 and 5) and components of the 4 MHz crystal comprises passive components that form the feedback network for the oscillator in the Pic-1654.

The power-on reset circuit 84 (FIGS. 4 and 5) form a 10 millisecond reset pulse to the microcomputer 66 at POWER-ON that allows the 4 MHz oscillator crystal 82 to start and the microcomputer 66 to become initialized.

A divide by ten counter 86 (FIGS. 4, 5 and 10) converts the 4 MHz computer clock to a 400 KHz square wave signal to operate the transmitter.

The divide by three counter 88 (FIGS. 4, 5 and 10) converts the 400 KHz signal to a 133 KHz signal that is applied to the microcomputer 66 as the real time clock counter input. Number thirteen and number fourteen are encompassed within the same IC (74HC390) divider chip which has a divide by ten and a divide by three circuit.

The front panel module 90 (FIGS. 4, 5, and 12) consists of two LED indicators 92 and 94. One is an "Over-Ice/Cup Remove" (FIGS. 4, 5 and 12) red indicator 92 and the other is a green "Fill" LED 94, indicating that the cup can be filled or is being filled. This indicator 94 remains "on" steady when a cup is ok until filling starts. In the event that there is too much ice in the cup, or that the cup is not recognized as a cup, the red indicator light 92 will flash on and off.

Figures 11A, 11B:
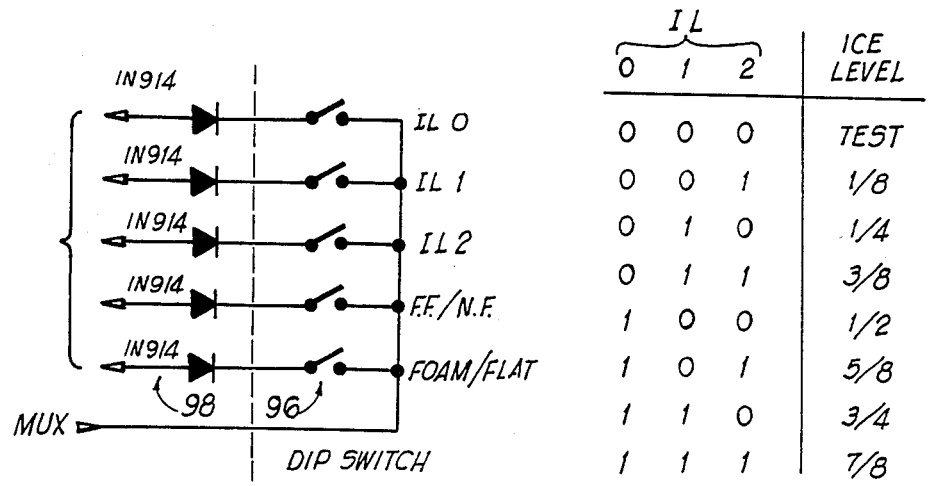
FIG. 11A is a schematic circuit diagram of the dip switch of FIG. 4.
FIG. 11B is a table showing how to set the switches for a desired ice level.
Figure 12:
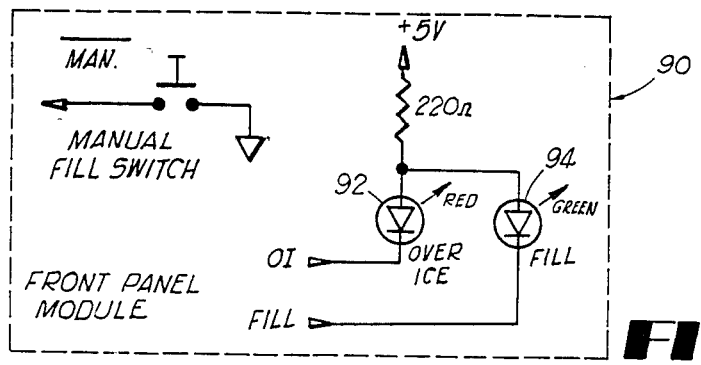
FIG. 12 is a schematic circuit diagram of the front panel module with the manual fill switch and the over-ice and filling indicator lights.

There is a programming dip switch 96 (FIGS. 4, 5, and 11A) comprising five individual switches accessible by removing a cover (not shown) on the lower rear surface of the control module 26. One switch is used to select between a normal flow or a fast flow valve assembly, depending upon which type of valve assembly the automatic control system is being attached to. Another switch is used for selecting a foamy or flat product such as water. The other three switches are used for selecting ice level or test position. The test position is used for alignment of the receiver during manufacturing and has no field use. The binary output of the three ice level switches allows for seven ice level selections from ⅛ cup to ⅞ths cup, as illustrated in FIG. 11B.

The multiplexer circuit 98 (FIGS. 4 and 5) allows the microcomputer 66 to read either the dip switches or to set the gain of the receiver as necessary. It is comprised of five signal diodes.

The power supply 100 (FIGS. 4, 5, and 8) uses 24 volts AC from the 50 VAC transformer (not shown) in the dispenser 10. The present control system consumes less than 2 volt-amps at 24 volts AC. The 24 volts AC is rectified and filtered to form a minus 20 volt DC supply and a plus 25 volt DC supply. The minus 20 volt supply is regulated with a Zener diode and supplies power to the transmitter. The plus 25 volt supply is unregulated but has a 39 volt Zener diode used as surge protection. The 25 volt DC supply is regulated down to 15 volts for the receiver subsystem by a 78L15 three terminal regulator 140. An MPS-A42 transistor 142 is used as a flyback oscillator to provide the plus five volts needed to operate the computer circuitry. The 4.3 volt Zener diode 144 connected between the plus five volt supply and the base of a 2N4124 transistor 146 serve to regulate the fly-back oscillator.

The output switch 104 (FIGS. 4, 5, and 8) for the two solenoids of the valve assembly 12 is operated from either the microcomputer 66 or the manual push button 102 on the front of the control module 26. The resistor diode network couples the microcomputer 66 and the manual switch 102 to the base of a 2N4124 transistor 148 which then turns the output triac 149 on or off, which then turns the two solenoids in the valve assembly 12 on or off.

Figure 13:
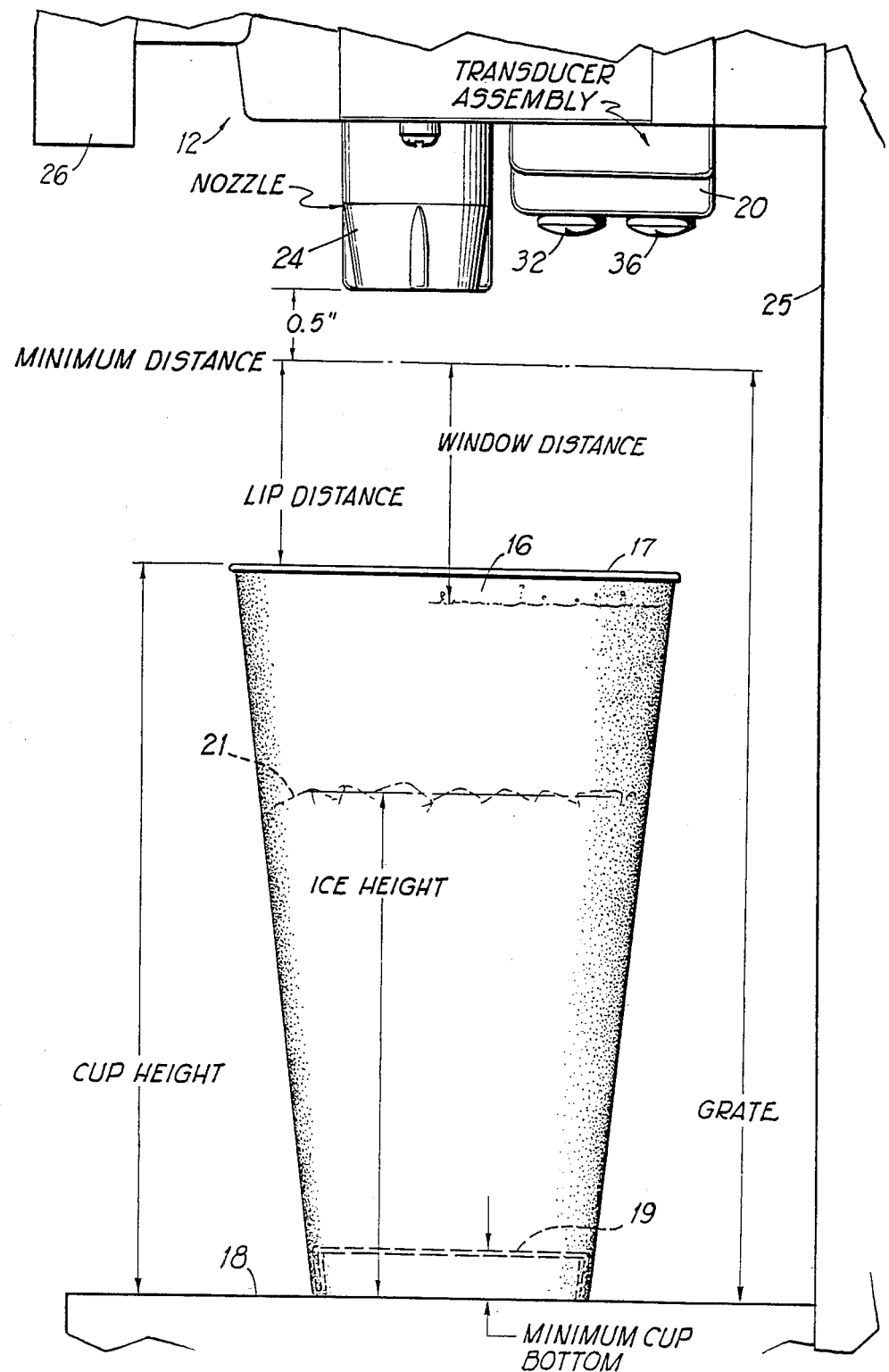
FIG. 13 is an elevational view showing a nozzle, the transducer assembly, the grate, and a cup.
Figure 14:
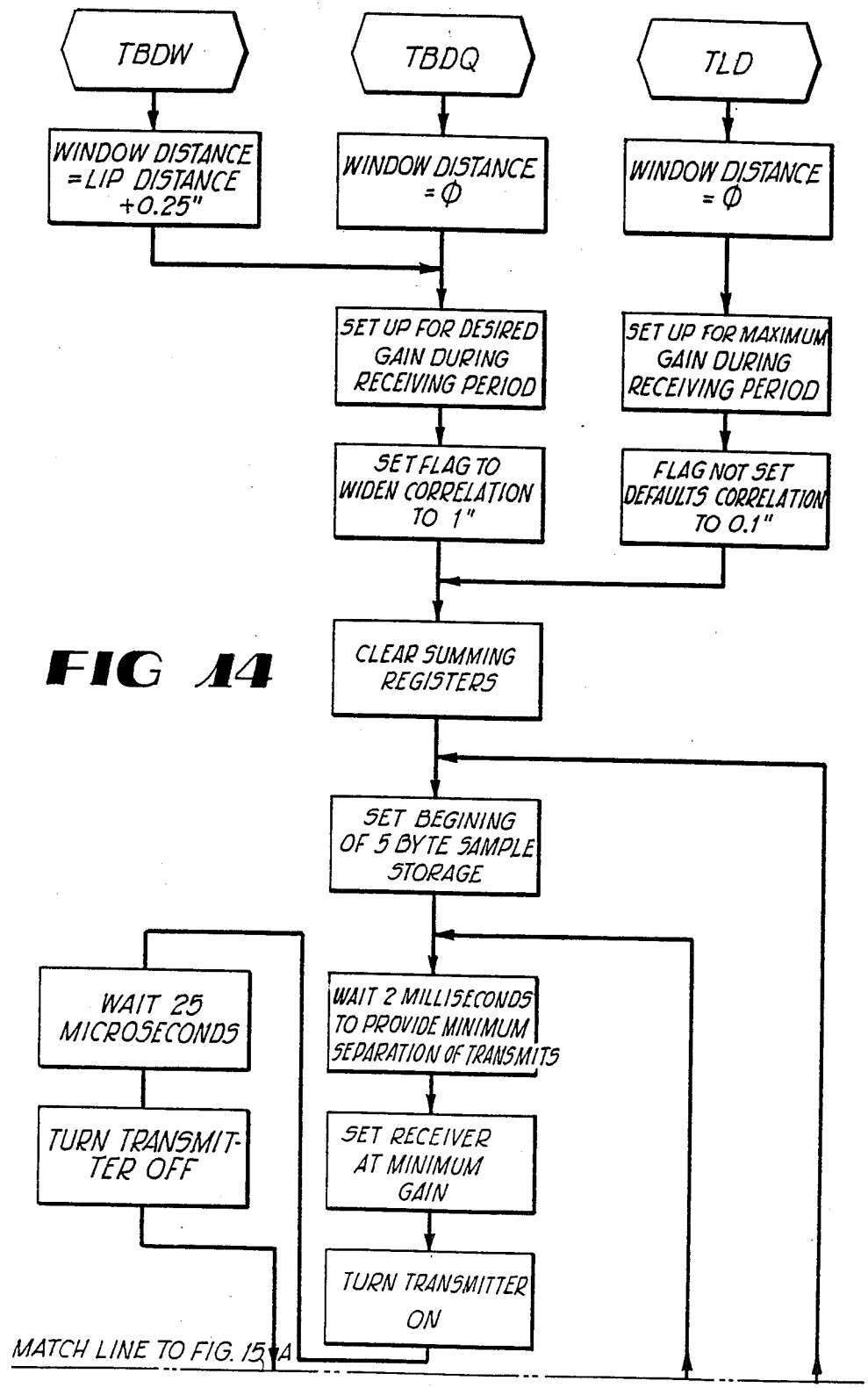
Figure 15:
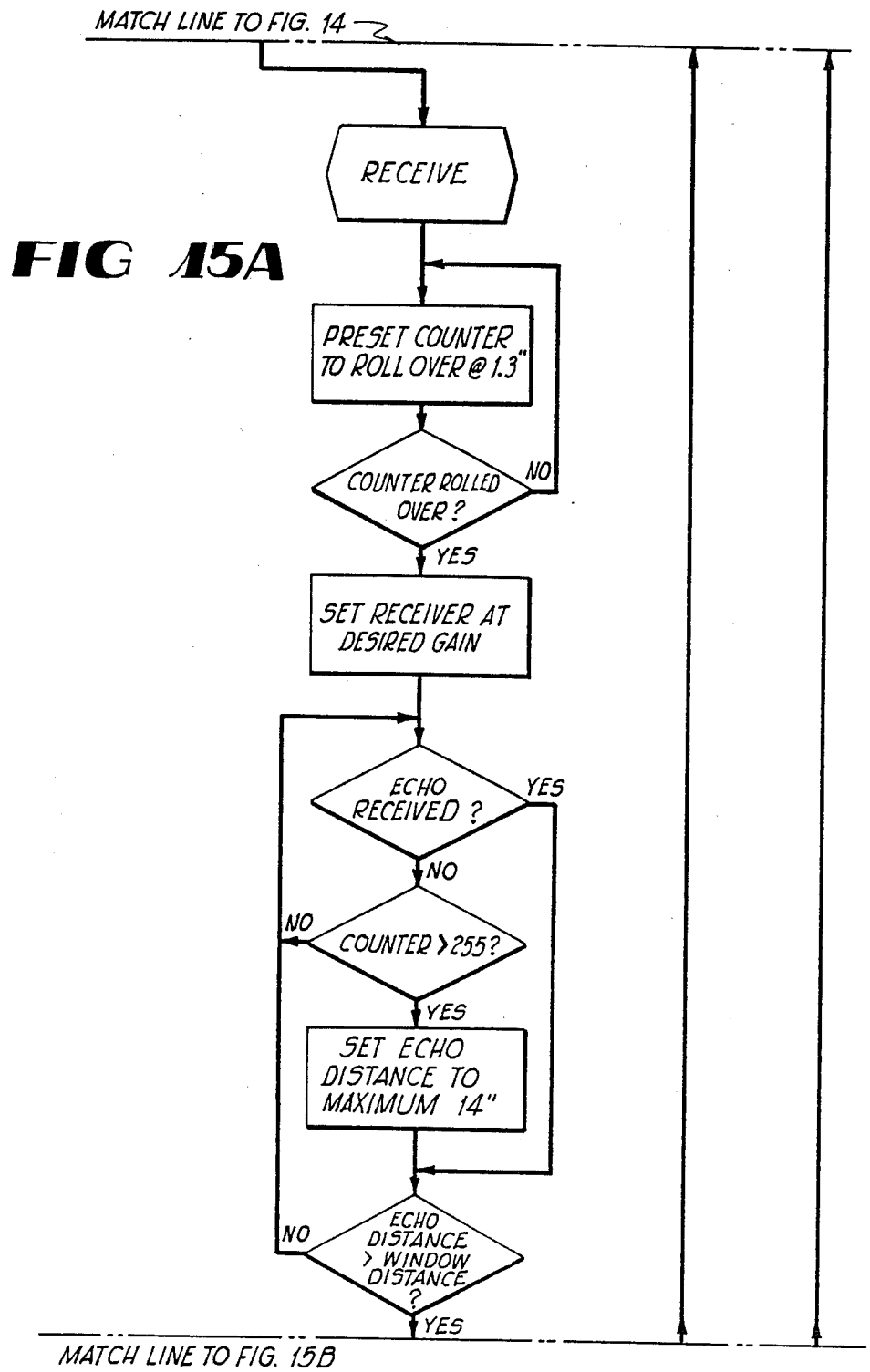
Figure 16:
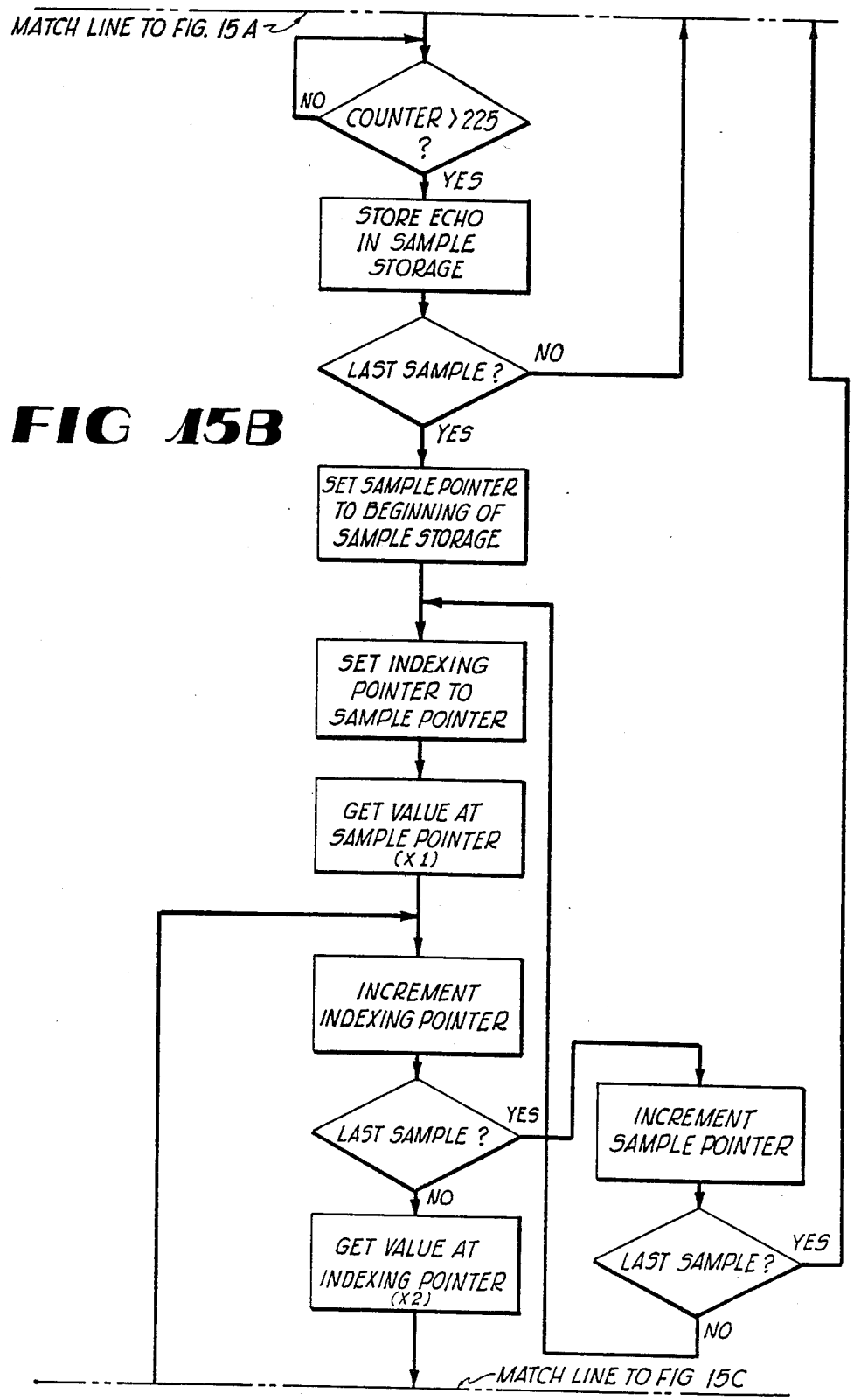
Figure 17:
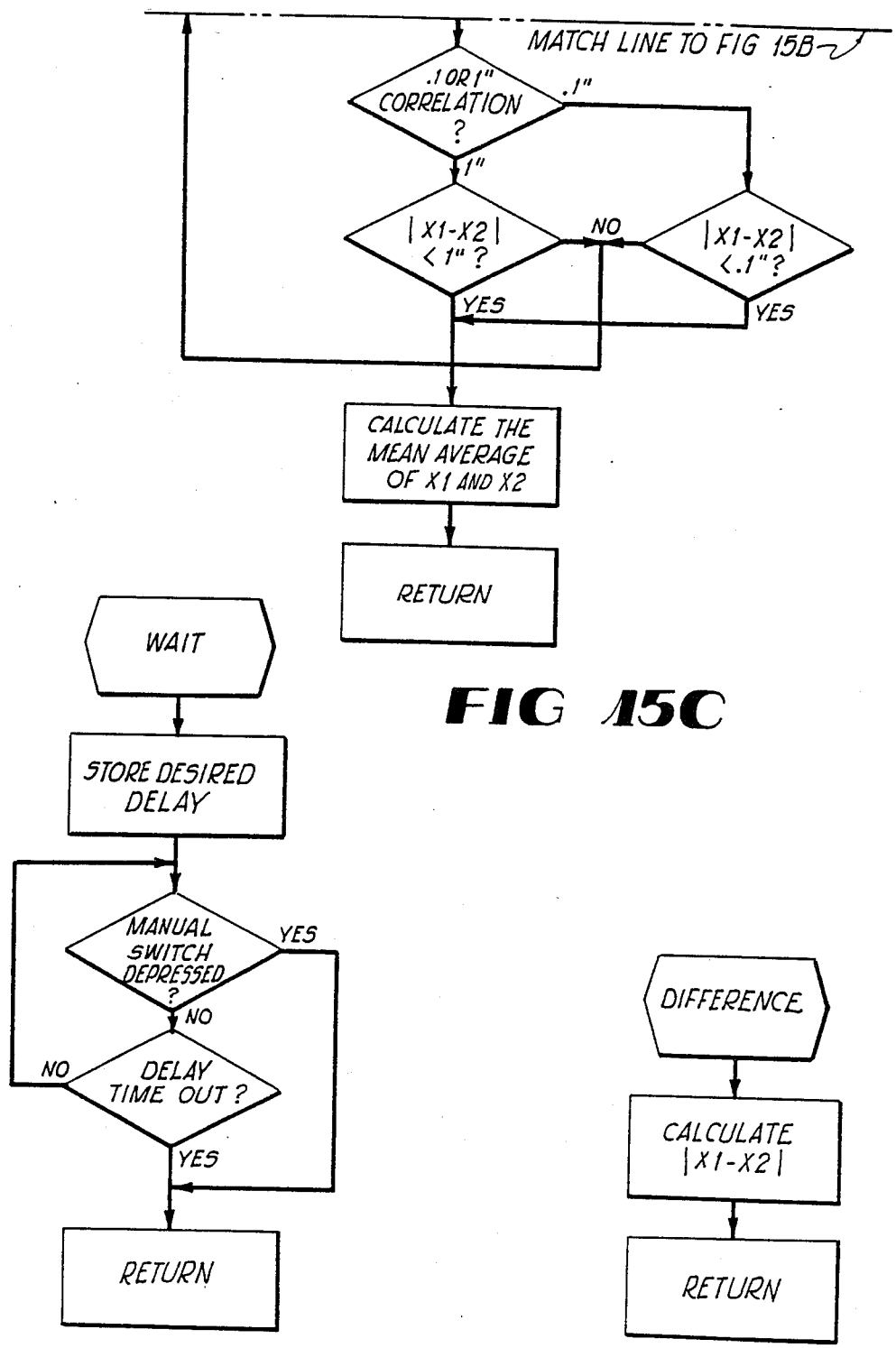
Figure 18:
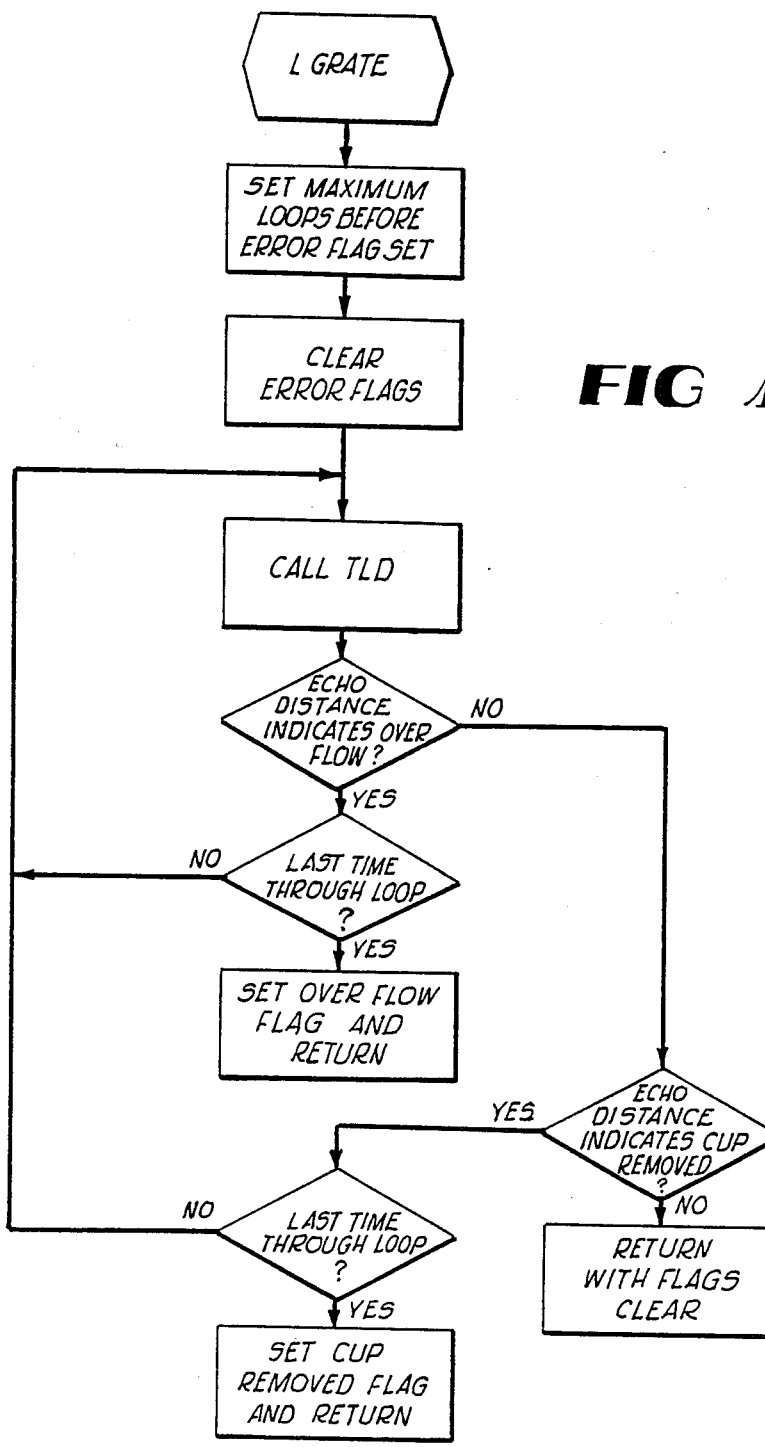
Figure 19:
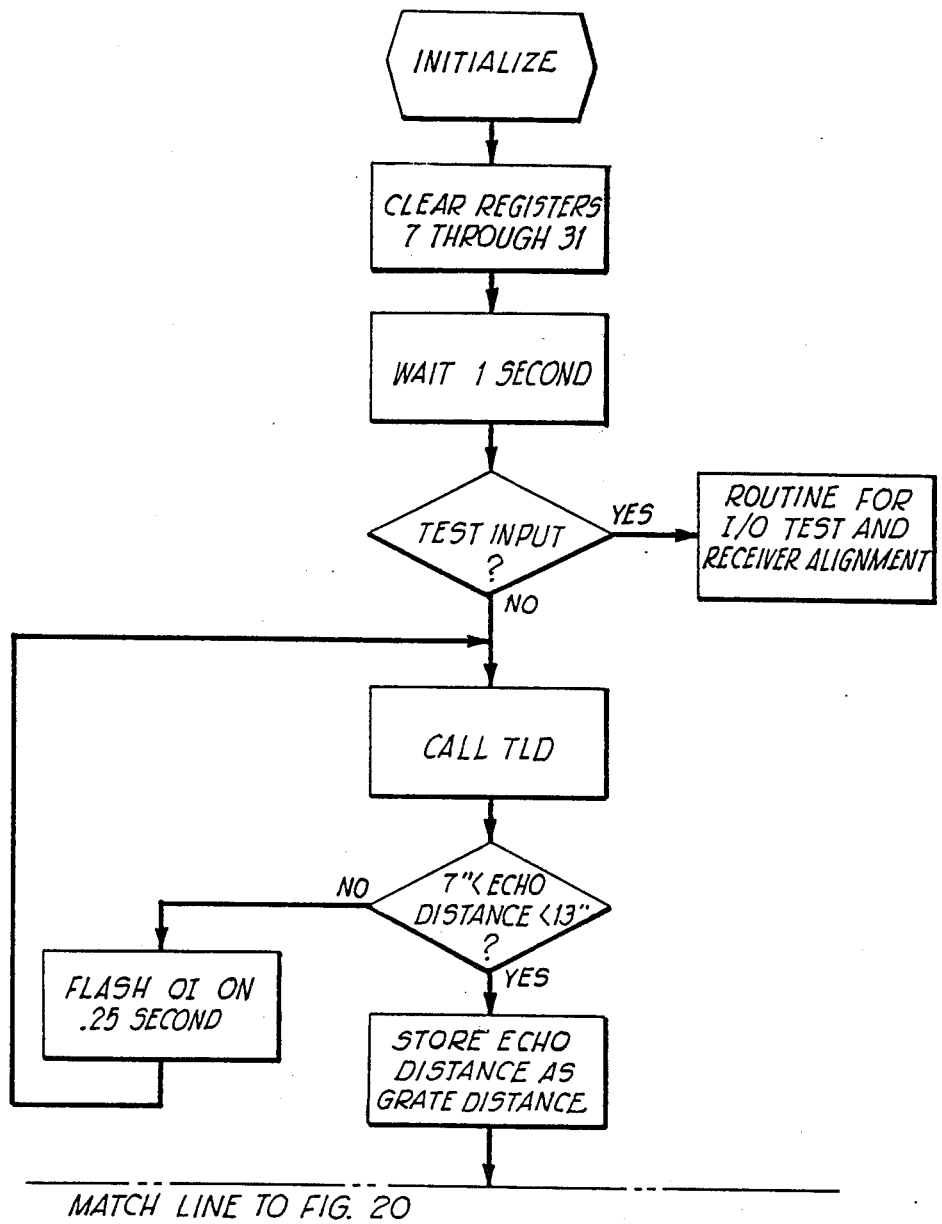
Figure 20A:
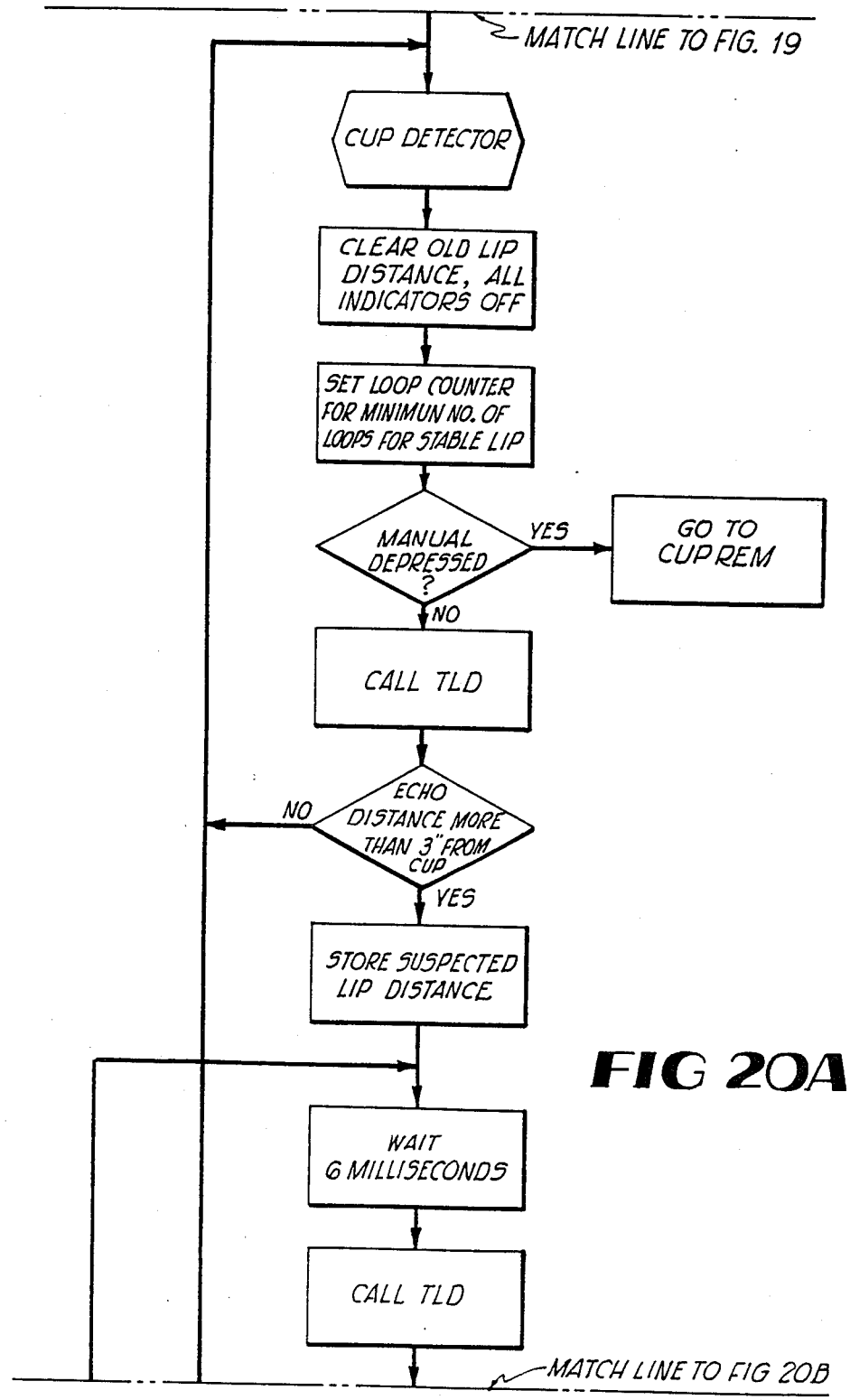
Figure 20B:
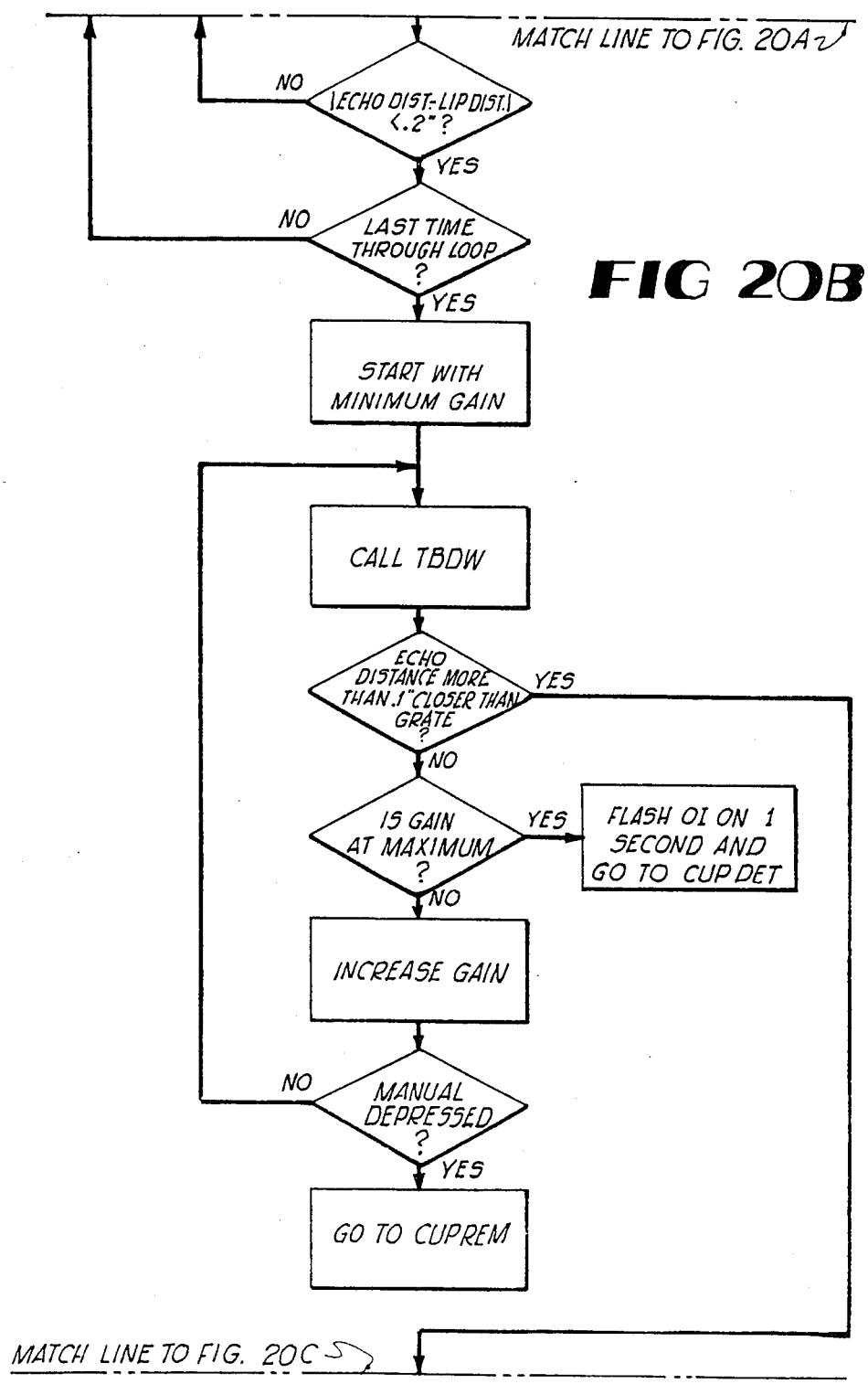
Figure 20C:
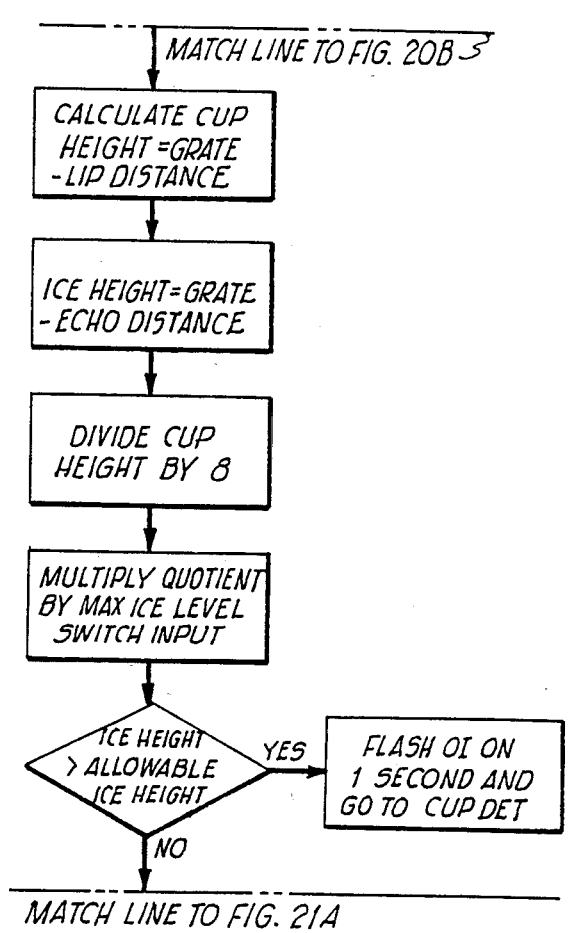
Figure 21A:
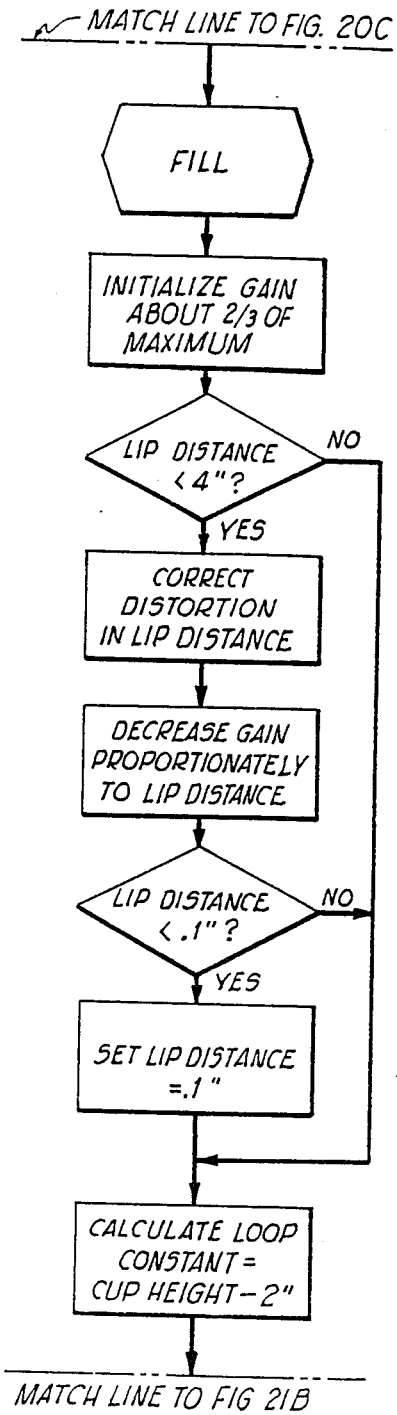
Figure 21B:
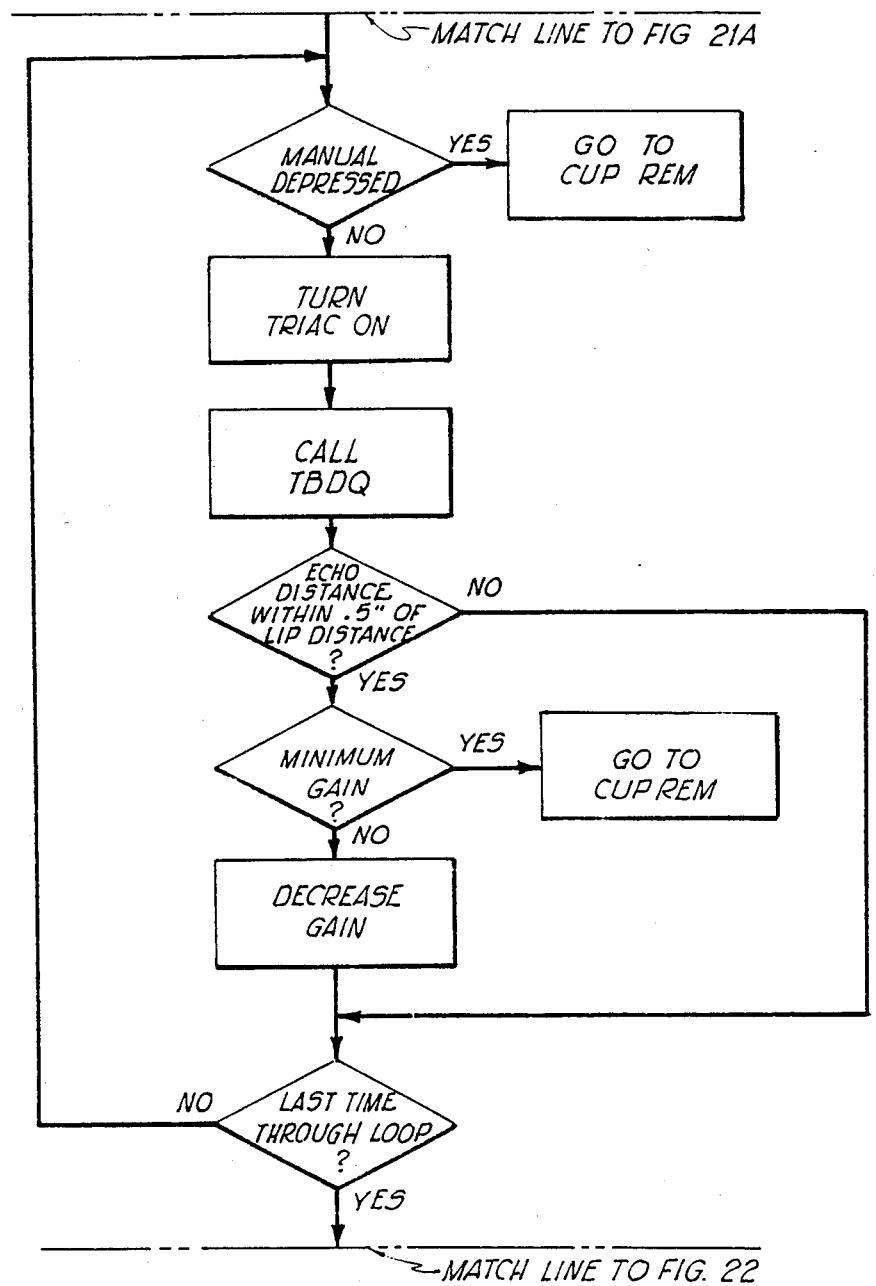
Figure 23:
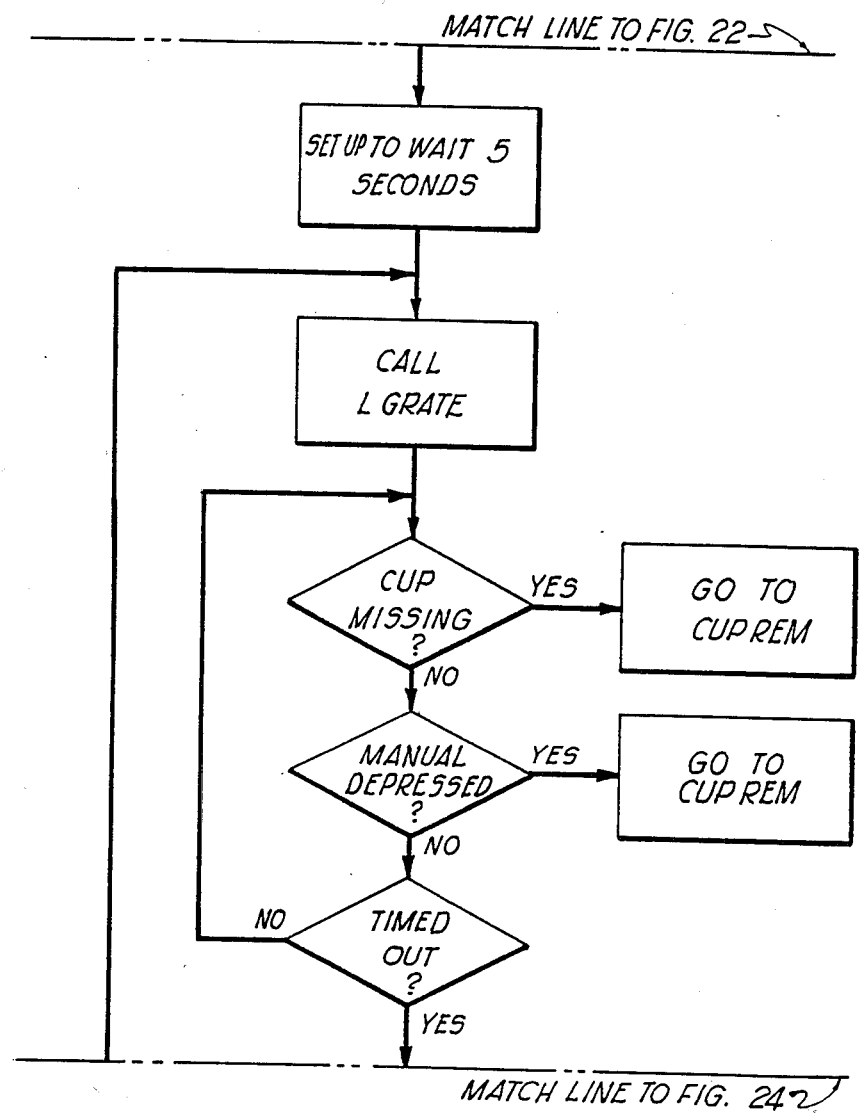
Figure 24:
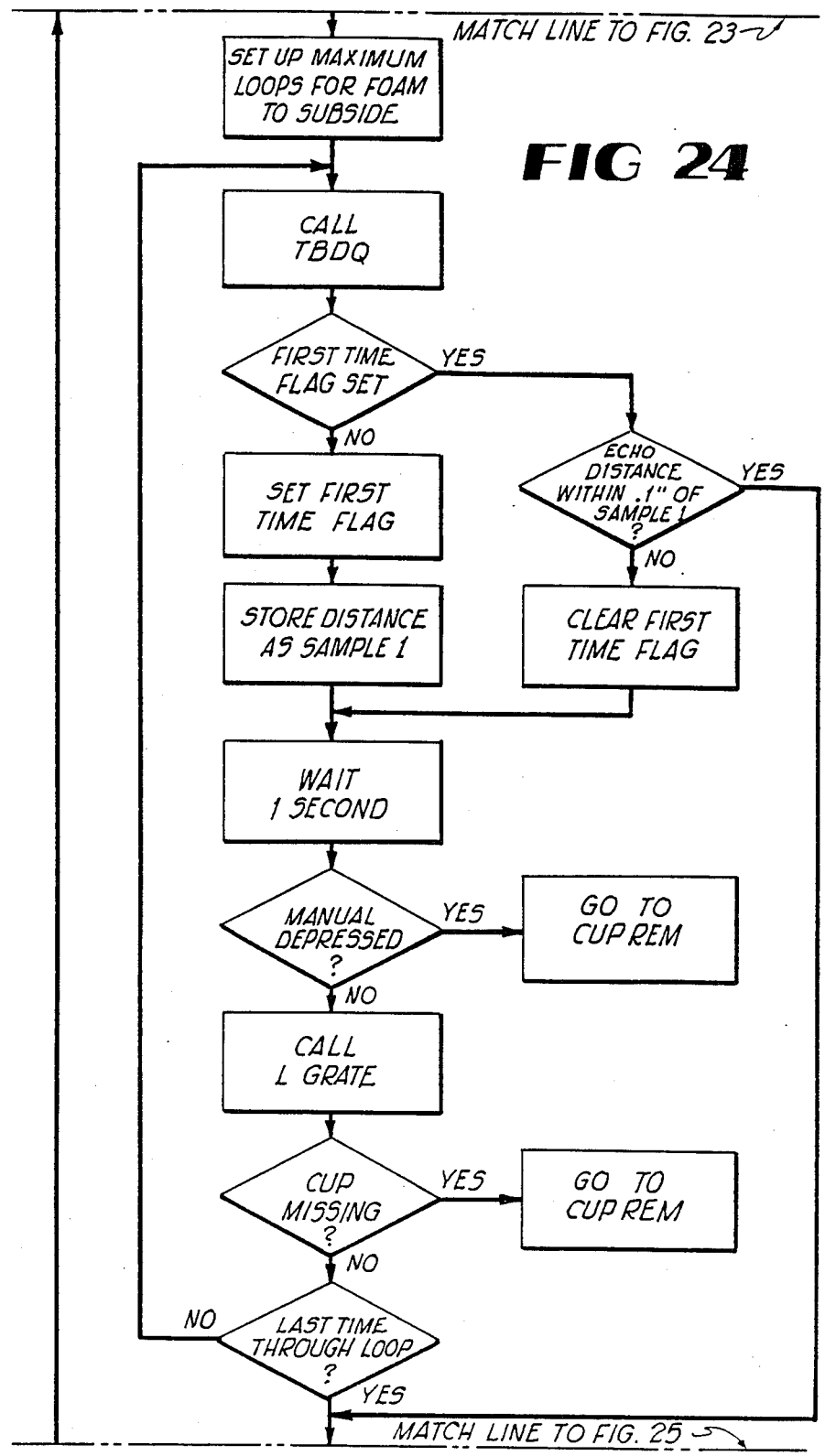
Figure 25:
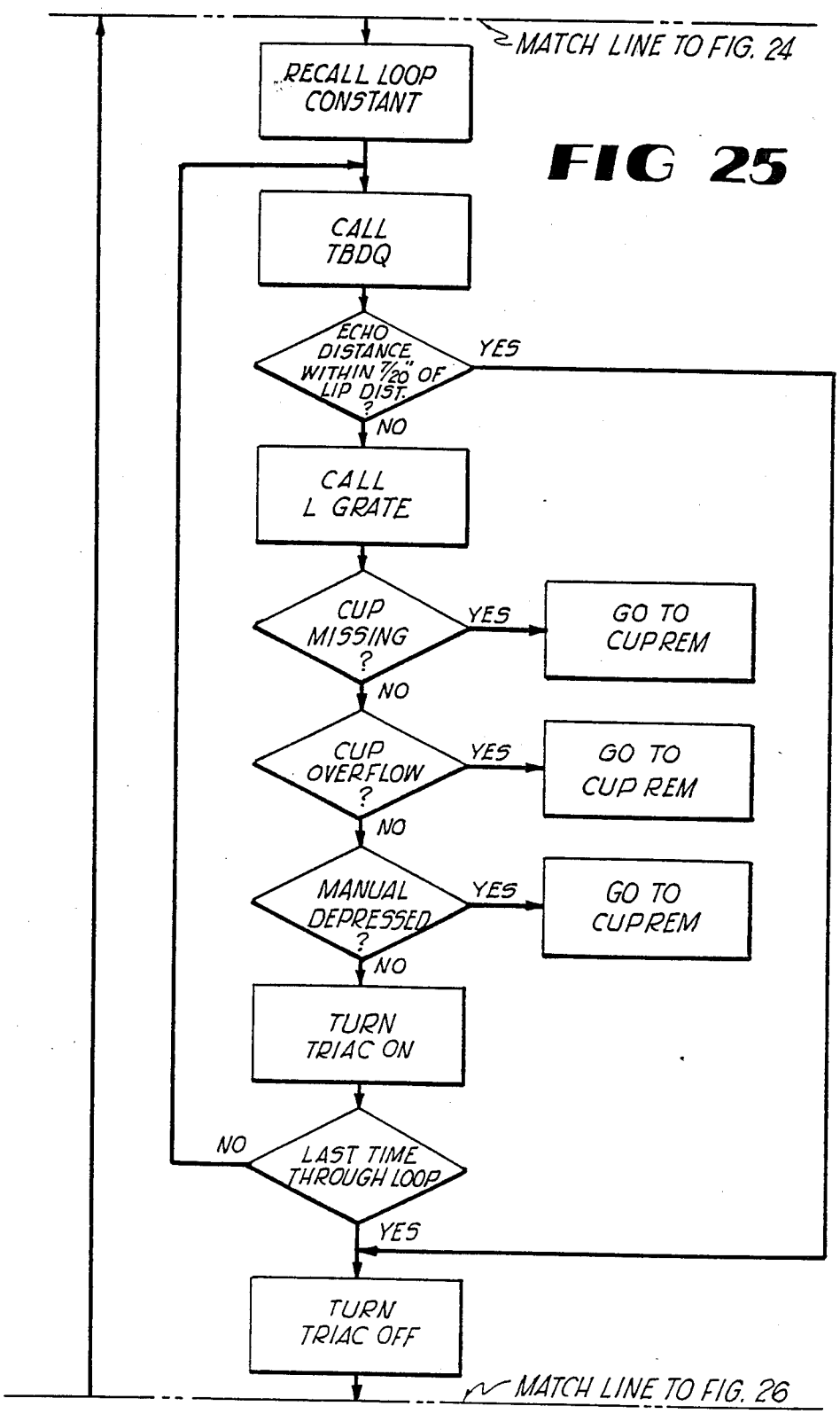
Figure 26:
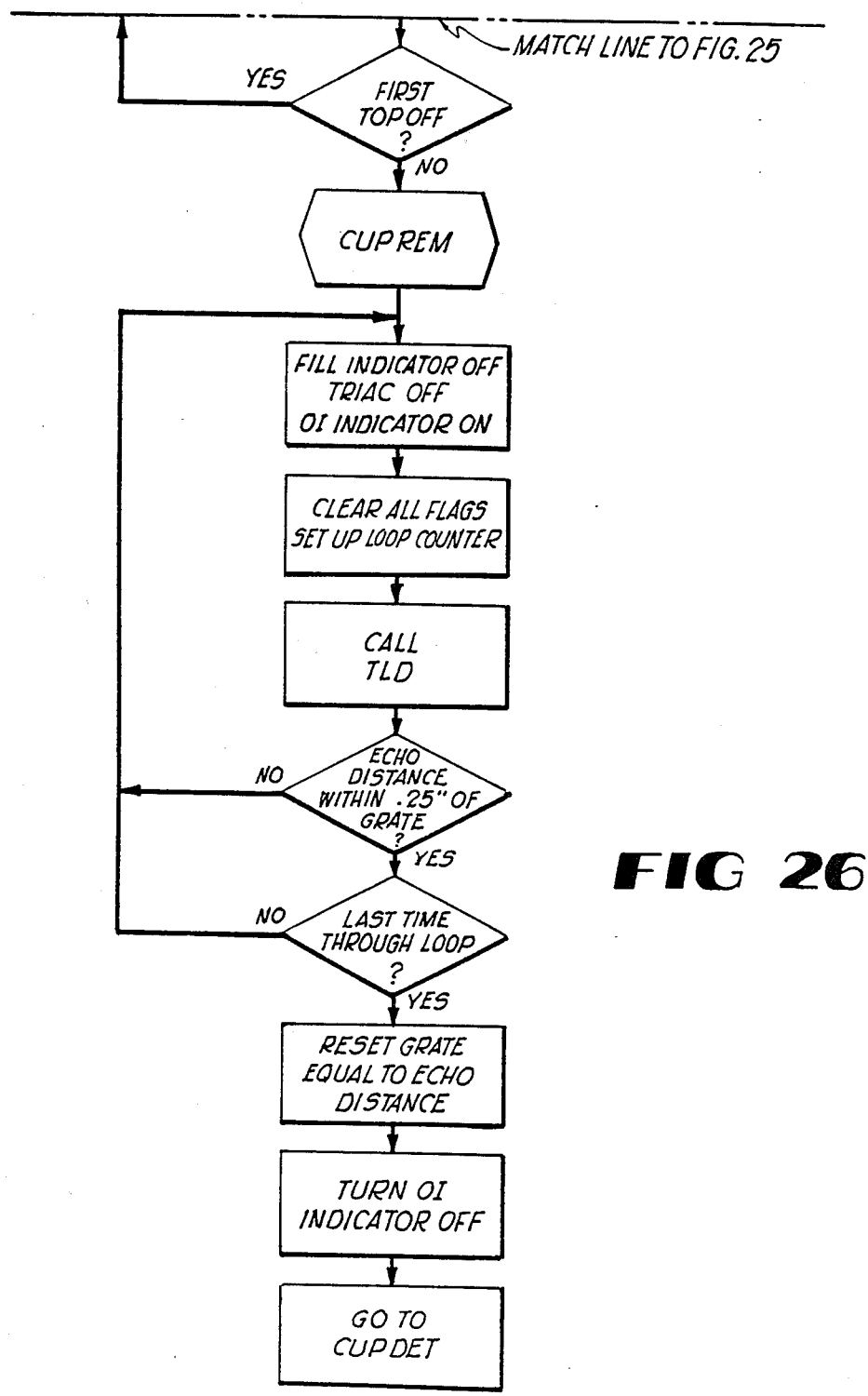

The software will now be described with reference to FIGS. 13 through 26. FIG. 13 is a side elevation view showing the transducer assembly 20, the lenses 32 and 36, the nozzle 24 of the beverage dispenser valve assembly 12, the control module 26, the splash plate 25, the grate 18 and a cup 16 having a cup lip 17, a cup bottom 19, and a top level 21 of ice in the cup.

The software includes four (4) major routines which are labeled Initialization Routine (INIT), Cup Detection (CUPDET), Fill Routine (FILL), and Cup Removal Routine (CUPREM).

The software also includes five (5) subroutines that are defined as Time Delay (WAIT), Absolute Value of the Difference of Two Numbers (DIFF), Grate/Overflow Detector (LGRATE), Transmit (TBDQ, TBDW, and TLD as described below), and Receive (REC).

The Transmitter Subroutine sets the variables for the receiver routine and outputs a 25 microsecond pulse (10 cycles at 400 KHz which occupies 0.1" air space) during which time the transmitter is active. The selection of receiver variables is made through three different entry points (or surfaces off which the transmitted beam reflects): TBDQ (Transmit Bottom Detector), TBDW (Transmit Bottom Detector with window), and TLD (Transmit Lip Detector).

The receiver has 32 steps of gain controlled by the software. The gain is set to minimum from the start of transmit to approximately 1.3" target distance time (180 microseconds). At that time the gain is set equal to the gain variable set up in the entry point routines. For TLD, the gain is always set to maximum. For TBDQ and TBDW, the gain is determined by the calling routine. In TBDQ and TLD, the distance of the first echo detected is captured for processing. In TBDW, a lip masking window is enabled which ignores any echoes closer than the lip distance +0.25". This allows a higher gain to be used to look at liquid level rising inside the cup. Under all entry points, 5 transmissions and receptions are made with the echo distances stored in RAM. The processing algorithm looks for two samples that correlate within 0.1" for TLD, or 1" for TBDQ and TBDW. The average of the two distances is used as the echo distance. A 2 millisecond delay is incorporated before each transmit to allow previous multiple reflections to decay.

WAIT is a programmable delay subroutine that returns to the calling routine immediately if the manual push button is pressed. It has a maximum delay of 1 second.

DIFF is a subroutine that calculates the absolute value of the difference of two numbers.

LGRATE is the Grate/Overflow detector subroutine and is used during the FILL routine. It uses TLD to detect with maximum gain and no window. If the subroutine detects an echo distance less than the lip distance minus 0.1", the overflow flag is set before returning. If the subroutine detects an echo distance within 0.25" of the grate distance, the cup removal flag is set before returning.

INIT is used when the microcomputer is initialized by the "Master Clear" (hardware). During power up, the first instruction processed is at location 777 octal. This instruction "GOTO INIT" commands the computer to begin executing this routine, which comprises the following: (1) the RAM is cleared; (2) wait 1 second for power to stabilize; (3) run the diagnostic routine if enabled; (4) use TLD to look with maximum gain and no window for an echo distance between 7" and 13"; (5) if it does not detect an echo within this range, the "Over Ice" indicator on the front panel flashes; (6) if it does detect an echo distance within 7" to 13", the distance is stored in RAM as the Grate distance and the program continues at CUPDET.

CUPDET is the Cup Detection routine. This routine collects data using TLD and accepts a cup using the following procedure:

A. The manual fill switch on the front panel is monitored continuously to assure proper operation. If the manual switch is pressed, the computer begins the Cup Removal routine immediately.

B. A stable lip distance must be established more than 3" from the grate. A stable lip distance is defined as 5 consecutive echo distances from TLD separated by 6 milliseconds that correlate within 0.2". This corresponds to the cup lip being stable for 130 milliseconds.

C. A cup bottom or ice level must be discerned that is more than 0.1" above the grate and more than 0.25" below the lip. This is accomplished by using TBDW and varying the gain as follows:

With minimum gain, obtain an echo distance using TBDW. If the echo distance is not more than 0.1" closer than the grate, then the gain is increased 1 step and another sample is taken. If the gain reaches the maximum, the Over-Ice indicator flashes and the Cup Detection routine begins again.

D. The ice/bottom height is calculated from the last distance obtained as outlined in (c) above and the grate, and then stored as the actual ice height. The cup height is calculated from the lip distance and the grate. The cup height is divided by 8 and the guotient is multiplied by the 3 bit binary number input as selected on the ice level programming switches. This allowable ice height is compared with the actual ice height. If the actual ice height is greater than allowed by the switch selection, the Over-Ice indicator flashes and the Cup Detection routine begins again. If the actual ice height is less than the amount selected by the switch, the FILL routine begins.

The FILL routine controls the complete filling and top off operation. The routine limits the solenoid operation to a maximum of 3 On/Off cycles. After each of the first 2 cycles, the routine waits for the foam to settle before starting the next cycle. After the foam is settled and the cup is within 7/20" of being full, the Cup Removal routine begins. If the manual switch is pressed at any time furing the FILL routine, the Cup Removal routine begins immediately. Each of the cycles has a maximum solenoid on time which if exceeded causes the Cup Removal routine to being.

A detailed description of the FILL routine follows:

A. Before the valve assembly 12 solenoids are actuated, several checks and corrections are made. The gain is initially set at 11/16 of maximum gain. If the Lip Distance is less than 4" the gain is adjusted with the empirically derived equation:

Gain=Gain−½(4"−lip distance).

If the Lip Distance is less than 4", the Lip Distance is adjusted with the empirically derived equation:

Lip Distance=Lip Distance−½(4"−Lip Distance)

If the Lip Distance is less than 0.1", the Lip Distance is set to 0.1" to allow the cup overflow to function properly.

The Time Constant for this particular cup height is calculated with the equation:

Time Constant=cup height−2".

This time constant is used in each of the three cycles to provide a maximum "Solenoids On" time proportional to the cup height.

B. The gain must be adjusted such that the fluid level is detected and the lip is not during the period when the cup vibrates such as at the beginning of a FILL. To accomplish this a period of time proportional to cup height is programmed to allow filling to start and gain enough weight to minimize cup vibration and adjust gain as necessary. During this time period the routine uses TBDQ to check if the echo distance is within 0.75" of the Lip Distance. If it is, the gain is reduced one step. If the gain reaches minimum, the cup removal routine begins. If the cup is removed during this period, the solenoids will not turn off because the Grate/Overflow detector subroutine is not called during the period due to trying to get as many samples as possible to adjust the gain. At the end of the period, the solenoids stay on.

C. A second maximum time period begins that is also proportional to the cup height. During this time period, the routine uses TBDW to monitor the liquid level and turns the solenoids off when the liquid level is within 0.5" of the Lip Distance. The Grate/Overflow detector subroutine checks to see if the cup has been removed or if TBDW has missed the liquid level rising and an overflow is imminent. If the cup is missing, the cup removal routine begins. If there is an overflow indicated, the solenoids are turned off.

D. A 5 second pause begins at this time to allow the foam to settle 0.25" below the cup lip. The Grate/Overflow subroutine checks once each second to ascertain that a cup is still in place. If the cup is missing, the cup removal routine is started.

E. After the 5 second pause, a minimum number of seconds for the foam to subside is set at 16, and once a second, an echo distance is obtained with TBDQ. If 2 consecutive echo distances are within 0.1" of each other, or if the period times out, the top off cycle begins. The Grate/Overflow detector subroutine checks once a second for a missing cup. Once a cup is found missing, the cup removal routine begins.

F. The top off cycle uses TBDQ to determine if the liquid level is within 7/20" of the lip. If this condition exists, the solenoids are not turned on. If the echo distance is not within 7/20", the solenoids turn on until that condition is met.

G. A repeat of "D," "E," and "F" now occurs to implement the second top off cycle.

The cup removal routine (CUPREM) turns the fill indicator 92 off, the value assembly 12 solenoids off, and the Over-Ice indicator 94 on. It uses TLD and waits for an echo distance within 0.25" of the grate. When this condition exists, a new grate distance is stored, the Over-Ice indicator turns off, and the Cup Detection routine begins again.

As described above, the system of the present invention provides an ultrasonic method and apparatus for controlling the automatic filling of beverage cups. The system can be used with any beverage, such as coffee, tea, milk, fruit juice, and carbonated soft drinks. The beverages can produce foam during filling or not. Different sized cups can be used and they can have ice therein.

The system can be used in conjunction with any known, standard beverage dispenser. In the case of carbonated soft drink dispensers, the transducer assembly and the control module of the present invention are located directly on the valve assembly. The cup actuated arm and the microswitch are removed from the standard valve assembly; the triac 149 in FIG. 8 takes the place of the microswitch and simultaneously turns the syrup solenoid and the carbonated water solenoid on and off.

The system of this invention is on and working whenever the power to the dispenser is on. The power is often left on to the dispenser to maintain the refrigeration system on.

A brief overview will now be provided without reference to the details of the system, which have already been described above.

The system first obtains a grate signal and stores it in the RAM. The way it does this is to transmit five 25 microsecond pulses (having a length in air of about 0.1 inch), each spaced apart about 2 milliseconds. If two signals are not received that are the same within 0.1 inch, then this first set of pulses is discarded and a new set of five pulses is immediately (in about two milliseconds) transmitted. If two signals are received and are within 0.1 inch, and if they are from a distance of from about 7 to 13 inches, then the system decides that it is the grate distance and stores it in the RAM.

The system then goes to the cup detection routine. The same set of pulses is transmitted and is received at maximum sensitivity. To determine that a cup is present, the system has to see 5 consecutive echo distances, each separated by 6 milliseconds, that correlate to within 0.2 inch. That is, 5 sets of pulses are transmitted with 6 milliseconds between each set. If at least two signals are received from the first set of 5 pulses that are within 0.1 inch, then that will be one value (or one echo distance). After receiving 5 of those in a row within 0.2 inch, the system knows that a cup lip (or something other than the grate) is present.

The system then goes to the next routine. In this routine the system looks for something greater than 0.1 inch above the grate and greater than 0.25 inch below the lip, that is, either the cup bottom or ice. If it finds this, it concludes that the something present is a cup (rather than just a hand, for example). When the ice or bottom is obtained, it is stored temporarily. The cup height is then calculated and the ice height is then calculated. It is then calculated whether or not the cup has too much ice. If it does not, the system goes to the FILL routine. This routine is somewhat complex.

In the FILL routine there are four filling periods. A first period or initial fill that is not monitored but which is set as a time function based on cup height. It will fill to about ⅓ cup under certain usual conditions. The system then switches automatically, without stopping the filling, to the second period in which the filling is monitored, and in which the filling is shut off when the liquid level rises to within 0.75 inch of the stored lip distance. The FILL routine then waits 5 seconds to allow foam to subside (if the control module is set for a foamy beverage). The monitoring continues waiting for the foam to quit moving and when two distances are received within 0.1 inch, then it calculates if the level is within 7/20 inch of the lip. If it is not, filling is resumed and monitored until the level is within 7/20 inch of the lip. If it is within 7/20 inch, filling does not resume. The "top off" routine is then repeated after another 5 second pause.

After the end of the FILL routine, the fill indicator light 92 is turned off, the solenoids are turned off, and the over-ice indicator light 94 turns off.

A second (and preferred) embodiment of the present invention will now be described with reference to FIGS. 27-46. An important difference between this preferred embodiment and that described above with reference to FIGS. 1-26 is that the preferred embodiment is designed so that two or more beverage dispensing valves having the ultrasonic control system of the preferred embodiment can be located in close proximity to each other, such as by being adjacent valves on a dispenser, without interference therebetween. However, many other features of the two embodiments are identical.

Figure 27:
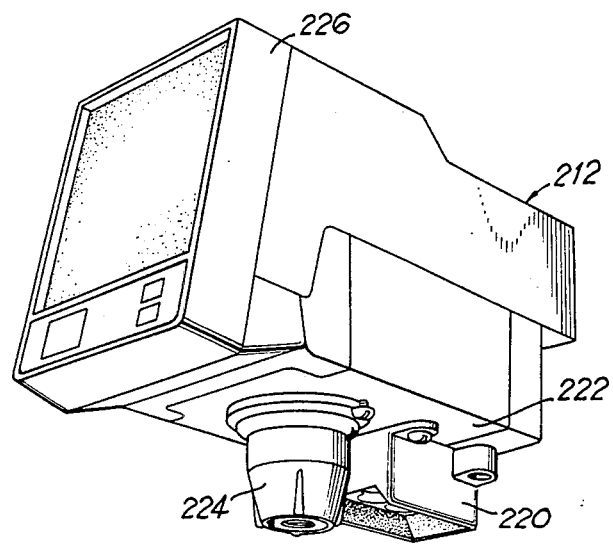
FIG. 27 is a perspective view of another embodiment of a valve assembly useful on the beverage dispenser of FIG. 1.

FIG. 27 shows a valve assembly 212, similar to valve assembly 12, that can be used as one or more of the valve assemblies on the dispenser 10 of FIG. 1. The automatic filling apparatus of this embodiment of the present invention includes a transducer assembly 220 located on the bottom surface 222 of the valve assembly 212 and behind the nozzle 224, and a control module 226 attached to the front of the valve assembly 212.

Figure 28:
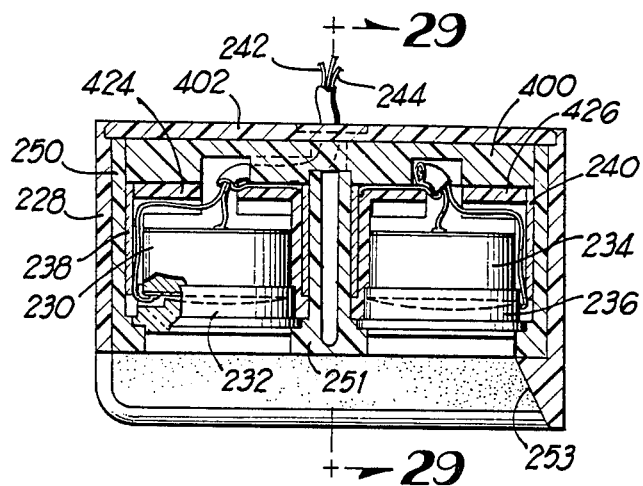
FIG. 28 is a cross-sectional side view of the transducer assembly shown in FIG. 27.
Figure 29:
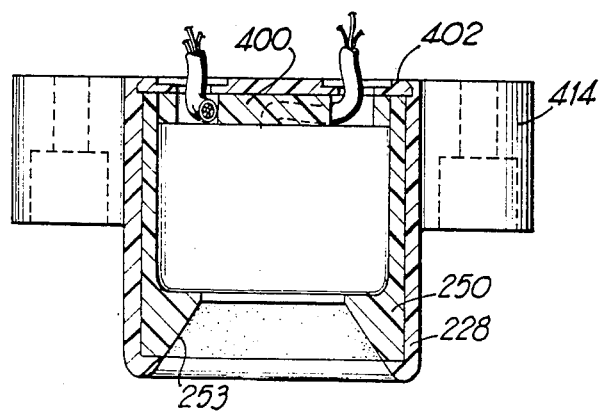
FIG. 29 is a cross-sectional end view of the transducer assembly of FIG. 28.
Figure 30:
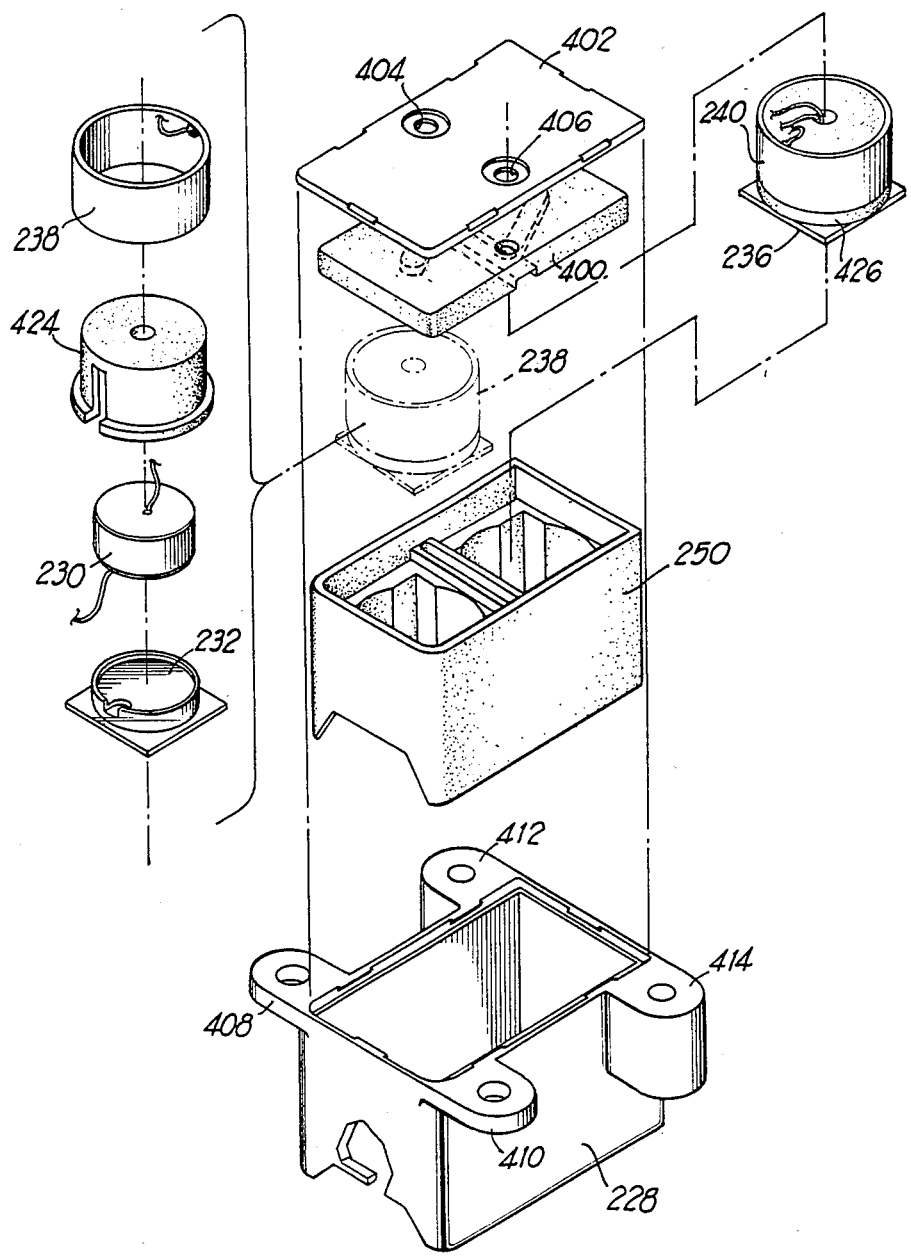
FIG. 30 is an exploded perspective view of the transducer assembly of FIG. 28.

The transducer assembly 220 is best shown in FIGS. 28-30 and includes a plastic housing 228 in which is contained a transmitter crystal 230 having a plastic lens 232, and a separate receiver crystal 234 having a plastic lens 236. The transmitter and receiver crystals are located inside of brass tubes 238 and 240, respectively.

A pair of shielded cables 242 and 244 each consist of a shield wire connected to a respective one of the brass tubes 238 and 240 and also a pair of wires connected to a respective one of the crystals at opposite locations thereon, as shown in FIG. 28. Each of the crystals has a metal plating on each of its upper and lower surfaces. The wire connections to the crystals are 28 gauge wire soldered directly to the crystal plating.

The cables 242 and 244 are about nine inches long and terminate in a single MTA connection (such as 48 in FIG. 3), for connection to the control module 226. Substantially all of the space within the housing 228 is filled with urethane foam 250.

The transmitter crystal 230 and the receiver crystal 234 are preferable PZT-5a ceramic crystals (a generic trade designation for a particular crystal material), which are a combination of lead titanate and lead zirconate. Each of the crystals is attached to its respective lens preferably by using about ½ drop of glue such as that sold under the trademark Eastman 910. The plastic lens is preferably made of ABS or polycarbonate plastic.

The plastic housing 228 has a pair of flanges on each side thereof, each flange having a screw hole for attaching the transducer assembly 220 to the valve assembly 212.

The brass tubes 238 and 240 have the same function as described above with reference to brass tubes 38 and 40. As shown in FIGS. 28-30, the transducer assembly 220 includes the plastic housing 228, a urethane foam filler 250, a urethane foam lid 400, a plastic cover 402, and the transmitter and receiver subassemblies 420 and 422, respectively, slid into a pair of spaced-apart cylindrical cavities in the foam filler 250.

The transmitter subassembly 420 includes the transmitter crystal 230, the lens 232, a urethane foam thimble 424 and the brass tube 238. The receiver subassembly similarly includes the receiver crystal 234, the lens 236, a urethane foam thimble 426 and the brass tube 240.

The lenses 232 and 234 are shaped as shown in FIGS. 28 and 30 with a square flange and a circular lip to receive the crystal. The crystal is glued to the lens as described above. The crystal-lens unit is then pushed inside the thimble and the tube is pushed over the thimble. The lens has a recess for the wire connection to the lower face of the crystal and the thimbles have two grooves as shown in FIG. 28 for the two wires connected to the crystal. No groove is provided for the wire connected to the brass tube.

The housing 228 has a pair of thin flanges 408 and 410 and a pair of thick flanges 412 and 414 with screw holes for use in connecting the transducer assembly 220 to the dispensing valve 212. The thick flanges 412 and 414 are used to adjust the position of the housing 220 and thus, the location of the transmitted beam.

As shown in FIG. 28, the lenses 232 and 236 are recessed into the bottom of the foam filler 250 to provide a baffle 251 there between. Also, the lower sidewalls 253 of the filler 250 extend downwardly below the lenses 232 and 234. The baffle 251 helps prevent ultrasonic energy passing directly from the transmitter to the receiver. The sidewalls 253 help prevent ultrasonic energy from being transmitted sideways to an adjacent valve. The foam absorbs the ultrasonic energy.

The selection of the most desirable frequency to use is also the same as described above with reference to the first embodiment.

Regarding the beam shape, at 14 inches, the total maximum beam pattern needs to be less than 3 inches wide at the limits of detectability ($-40$ db) in the side to side direction and approximately 3 inches front to back with $-3$ db point in the front followed closely by the 0 db point and then tapering off to $-6$ db at the rear. The gain at a point near the front of the pattern (toward the nozzle) needs to be a maximum with the gain falling off smoothly by about 6 db as the pattern reaches the back point. The crystal pattern was chosen empirically as the one giving the best cup lip to ice (front) ratio with the crystals aligned from front to back between the nozzle 224 and the splash plate 25.

The resulting overall gain pattern at 12 inches had a spread sideways of 3.5 degrees, and a resulting spread front to rear of 12 degrees.

To achieve the desired beam pattern, it was necessary to lens the crystals. A 2 inch concave radius produced the 8 degrees to 3.5 degrees narrowing from side to side for both transmit and receiving crystals, a 4 inch convex radius produced the 8° to 12° spreading from front to rear for the receiver crystal and a flat lens toward the front for ½ the crystal followed by a 3 inch convex radius to the rear for the transmitter crystal which formed a fan-shaped beam pattern with an elongated footprint having a width of approximately ¾ inch at $-3$ db and having a length of about 2½ inches with a bright spot about 1 inch in from the front with $-3$ db at the front and $-6$ db at the rear and 12 inches away from the transducer assembly 220. This beam-shape footprint has its long dimension extending front to back relative to the the dispenser.

Coupling from the crystals to the air was calculated in the same manner described above for the first embodiment.

One change in this second embodiment is that the lenses are inset into the bottom surface of the foam package.

Regarding the crystal shape and material, the transmitter crystal is preferably ½" OD×0.200" for a series resonance of 400 KHz. PZT-5a material was chosen for the crystals 230 and 234 as the best compromise in strength, efficiency, low mechanical Q, and ease of workability. The receiver crystal is preferably ½" OD×0.190" for a parallel resonance of 400 KHz, and is also made of PZT-5a material.

Regarding the electrical wiring, a twisted shielded pair of 28 gauge stranded wire is used and soldered directly to the plating on the crystal faces. The wire shielding is soldered to the brass tubes 238 and 240. The brass tubes are isolated from each other electrically. The black wire of the twisted pair is attached to the outside crystal face which is marked with a small dot.

Figure 31B:
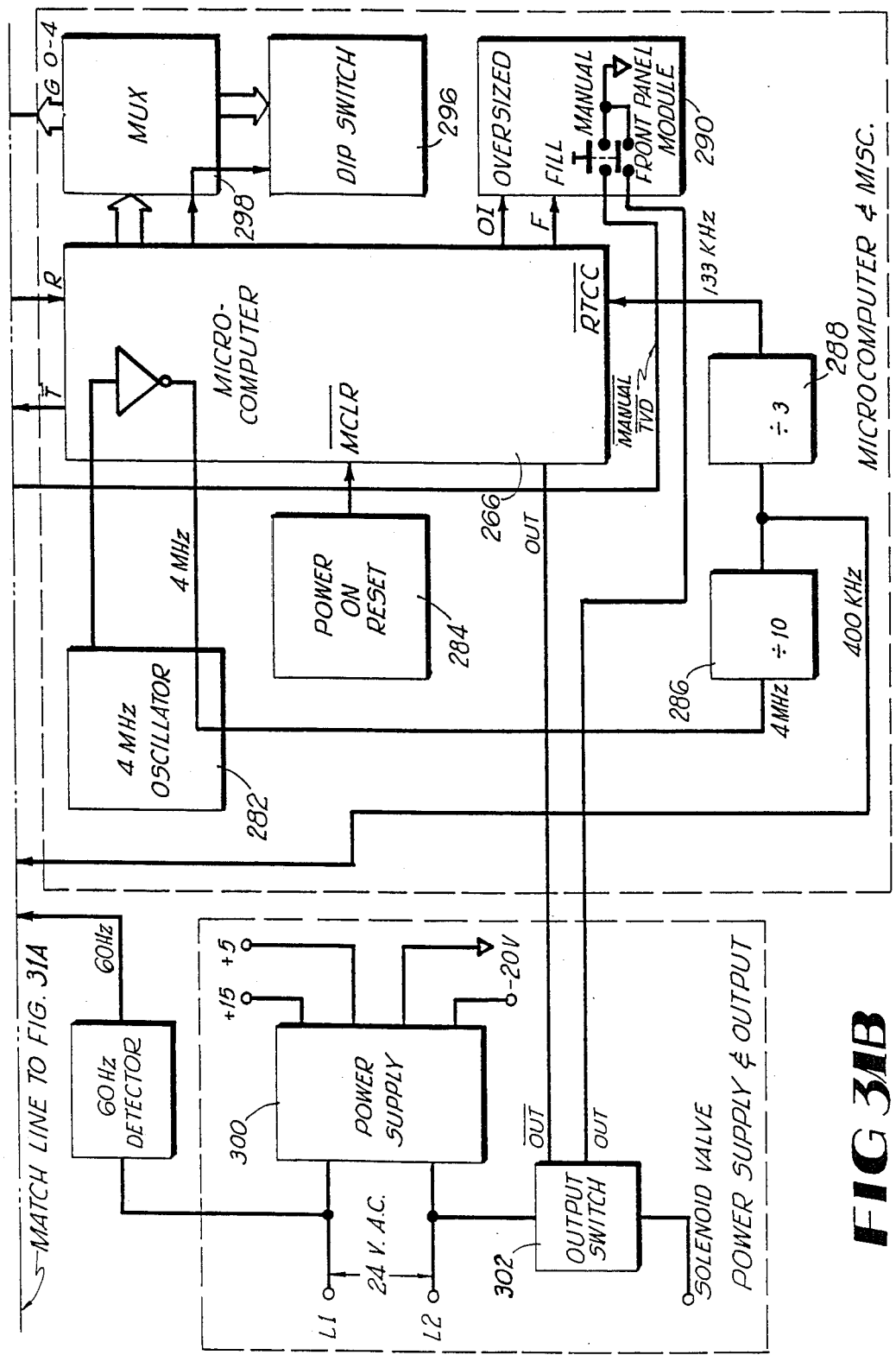
Figure 32:
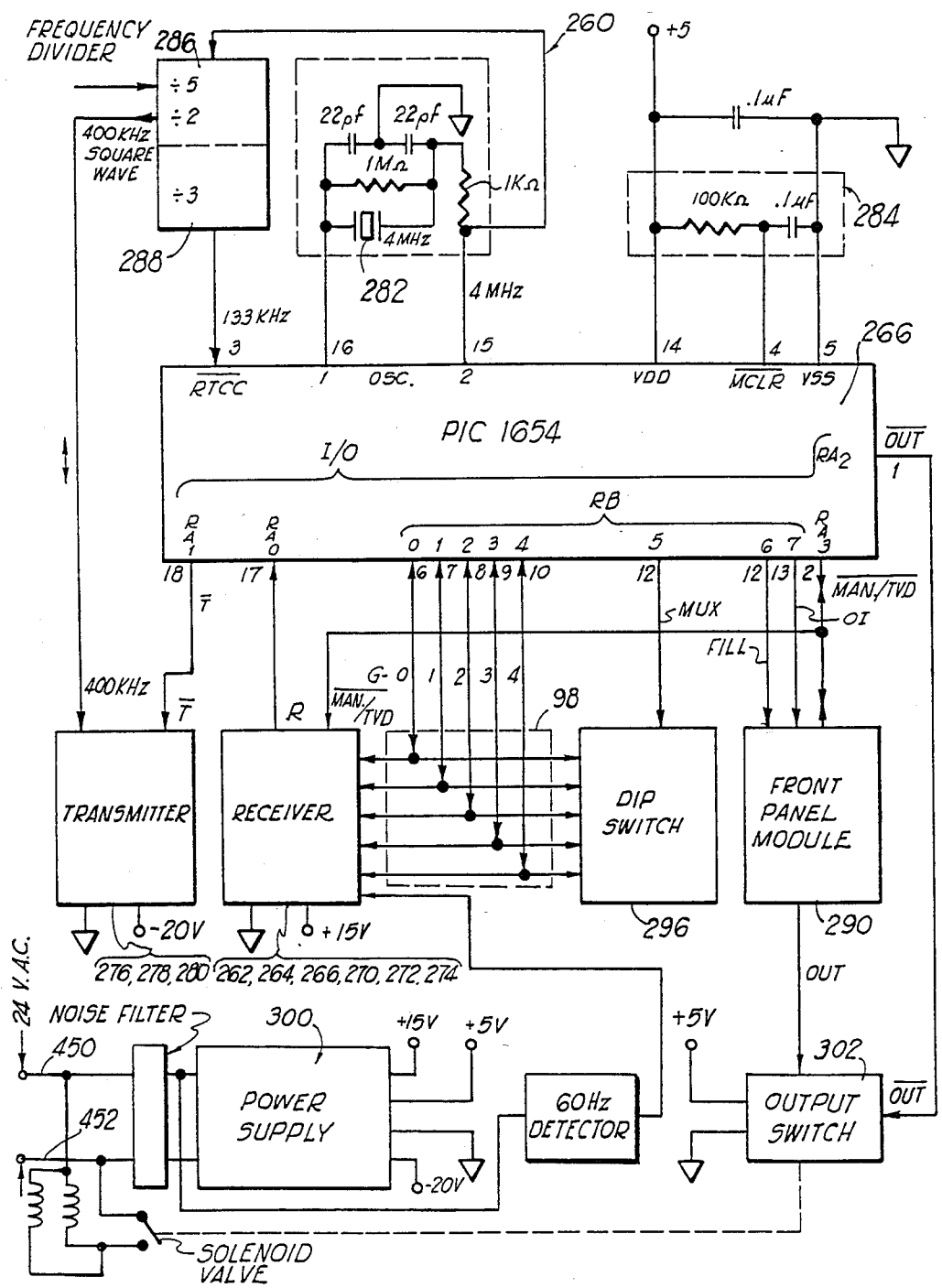
FIG. 32 is a microprocessor block diagram.
Figure 33:
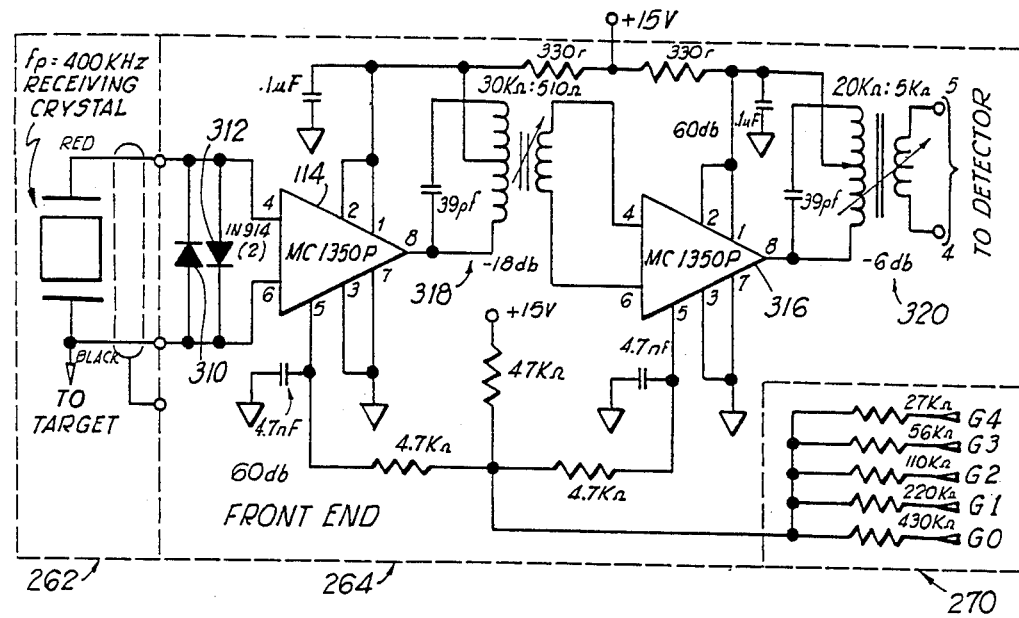
FIG. 33 is a schematic circuit diagram of part of the receiver subassembly including the receiver, the receiver front end, and the D/A gain reduction of FIG. 31.
Figure 34:
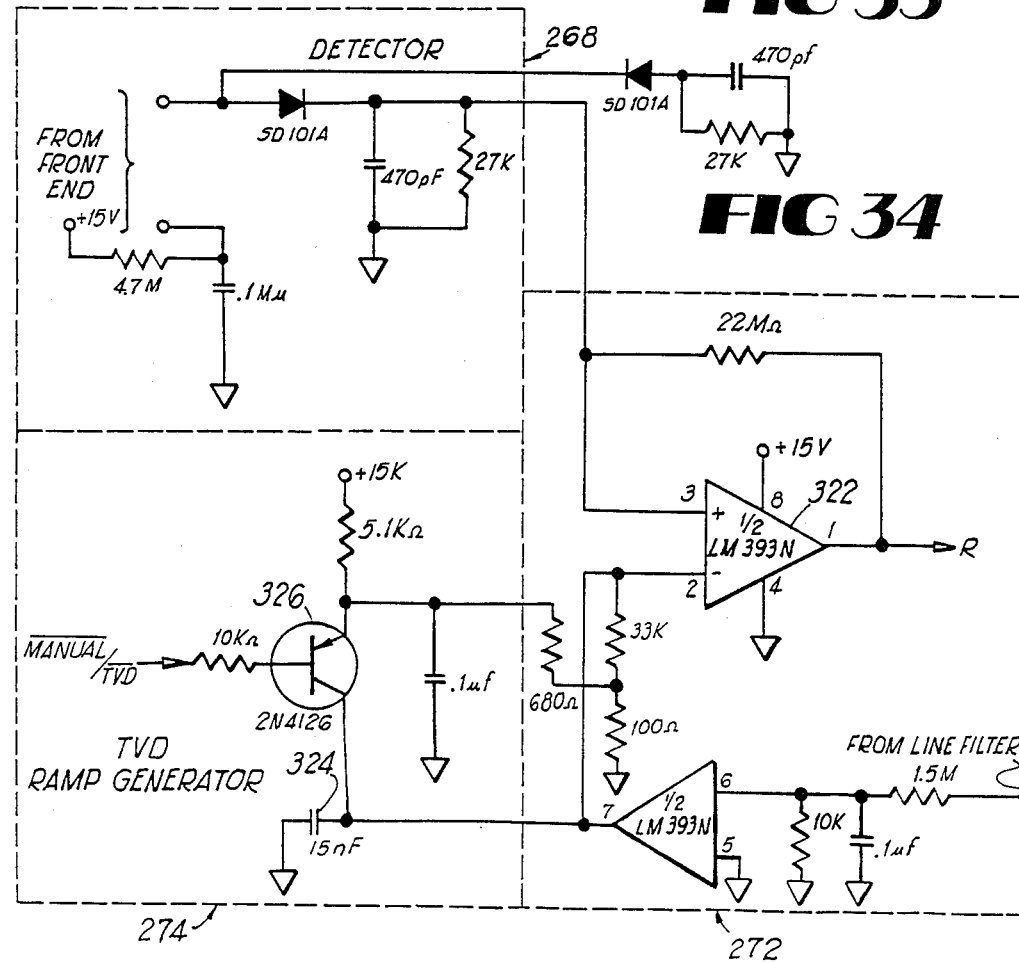
FIG. 34 is a schematic circuit diagram of another part of the receiver subassembly including the detector threshold comparator, the time varying detection generator, and the 60 Hz detector of FIG. 31.
Figure 35:
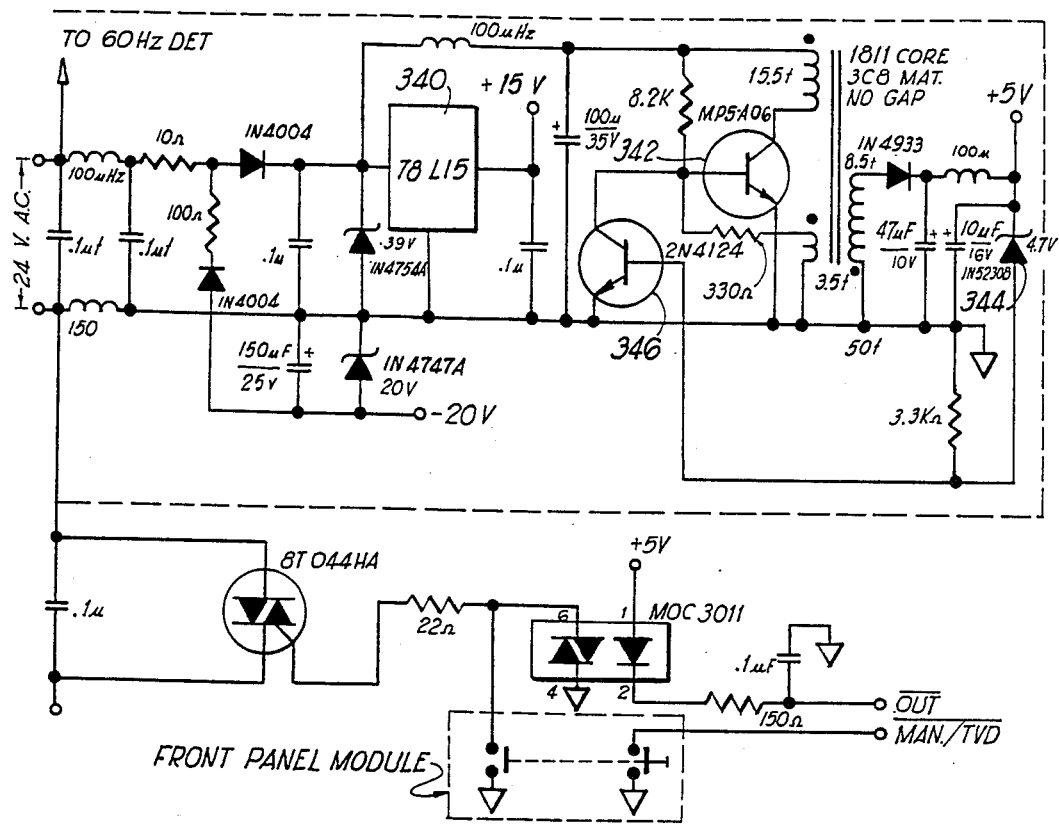
FIG. 35 is a schematic circuit diagram of the power supply and output switch of FIG. 31.
Figure 36:
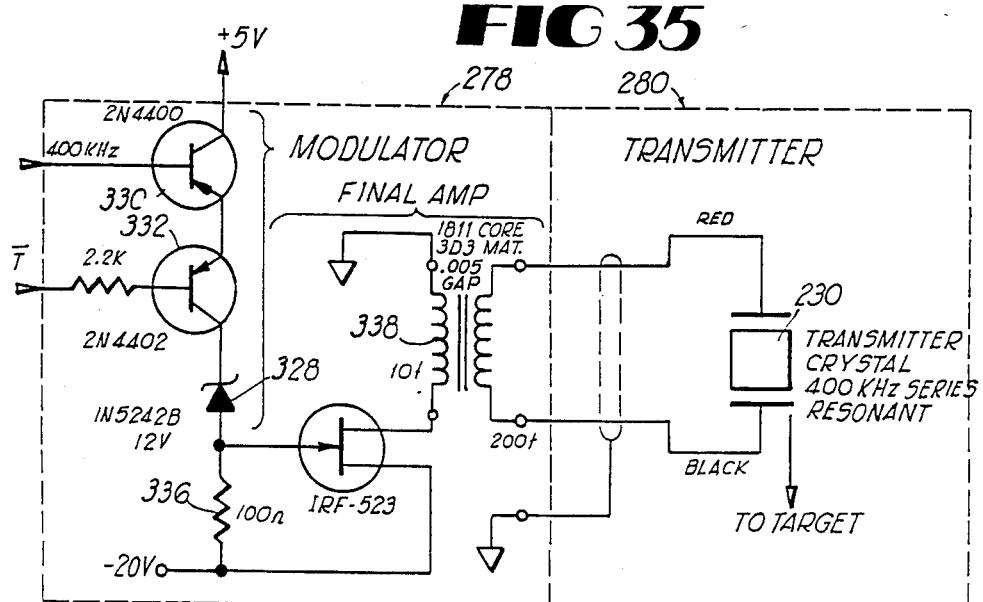
FIG. 36 is a schematic circuit diagram of the transmitter subsystem of FIG. 31.
Figure 40A:
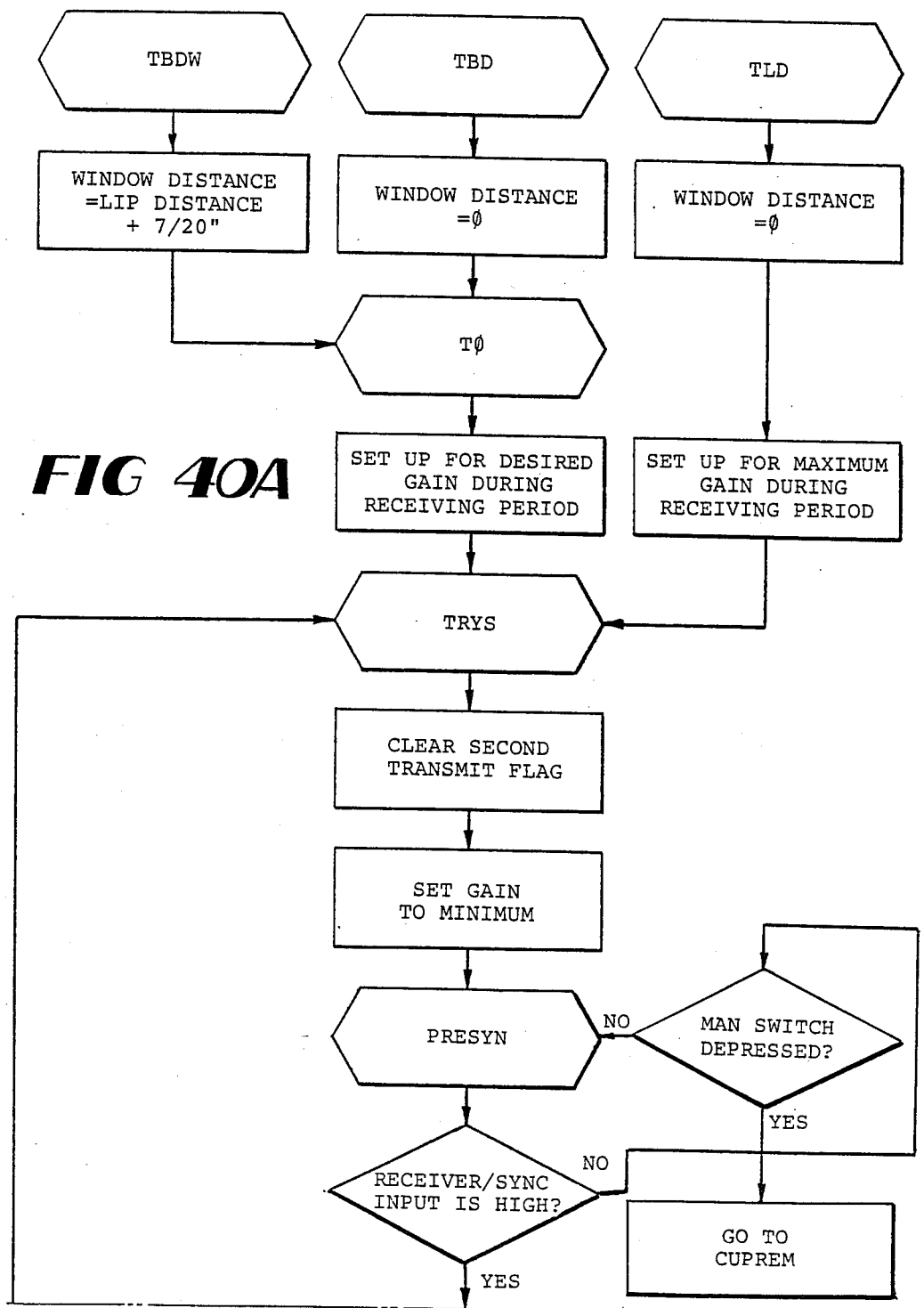
FIGS. 40–46 are flow charts illustrating the main routine and the subroutines of the software for operating the microcomputer in the block diagram of FIG. 31.
Figure 40B:
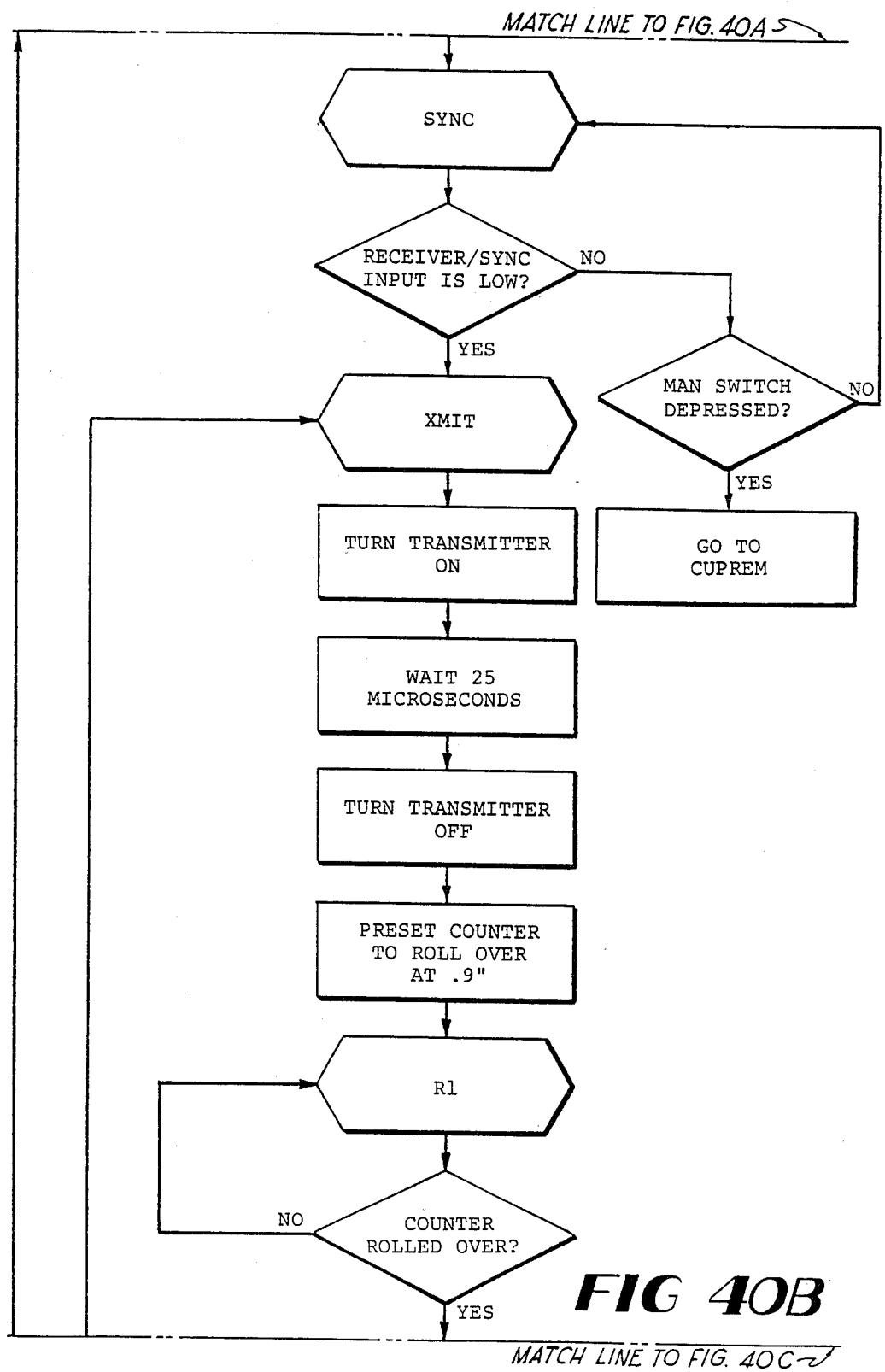
Figure 40C:
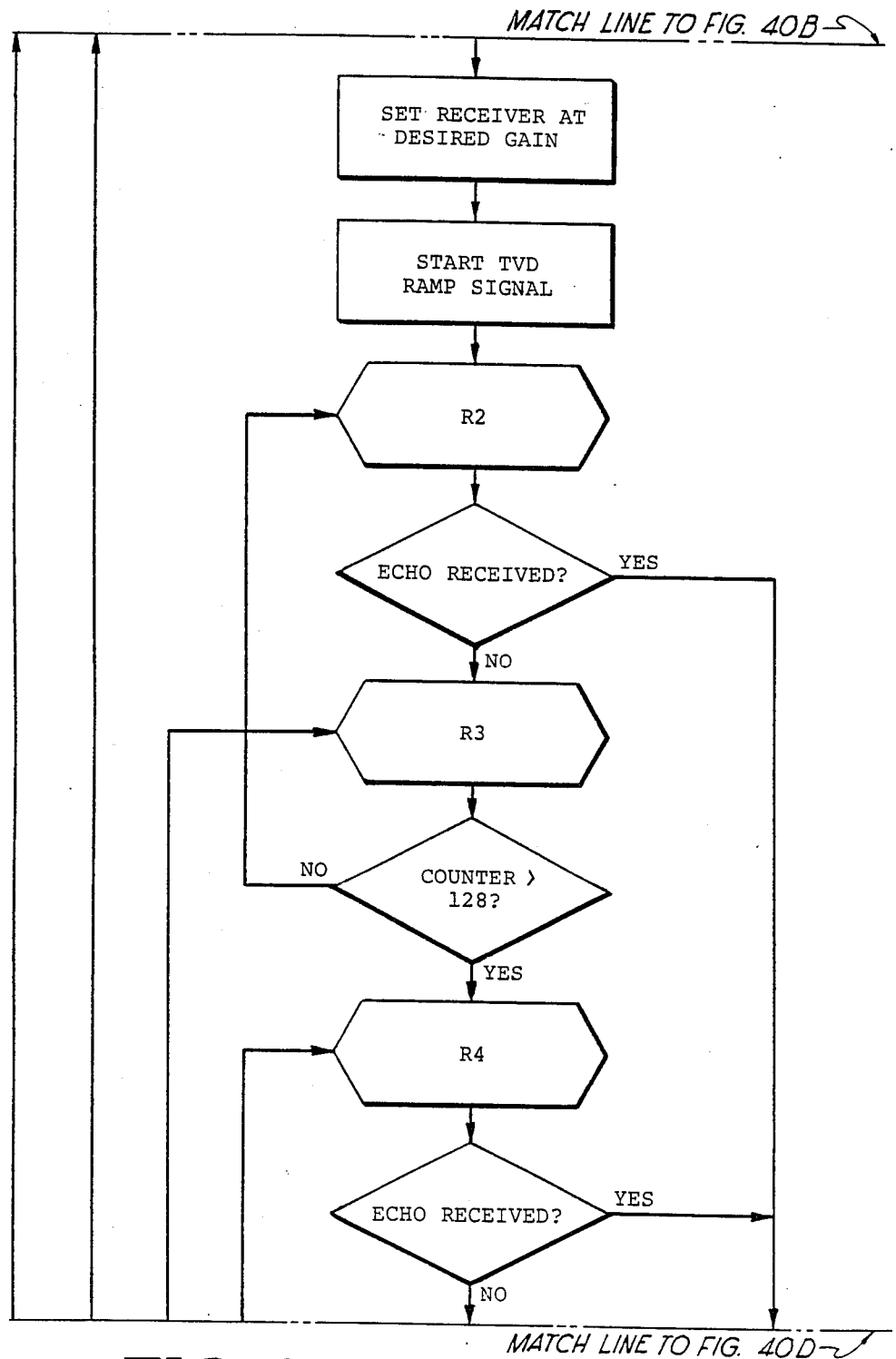
Figure 40D:
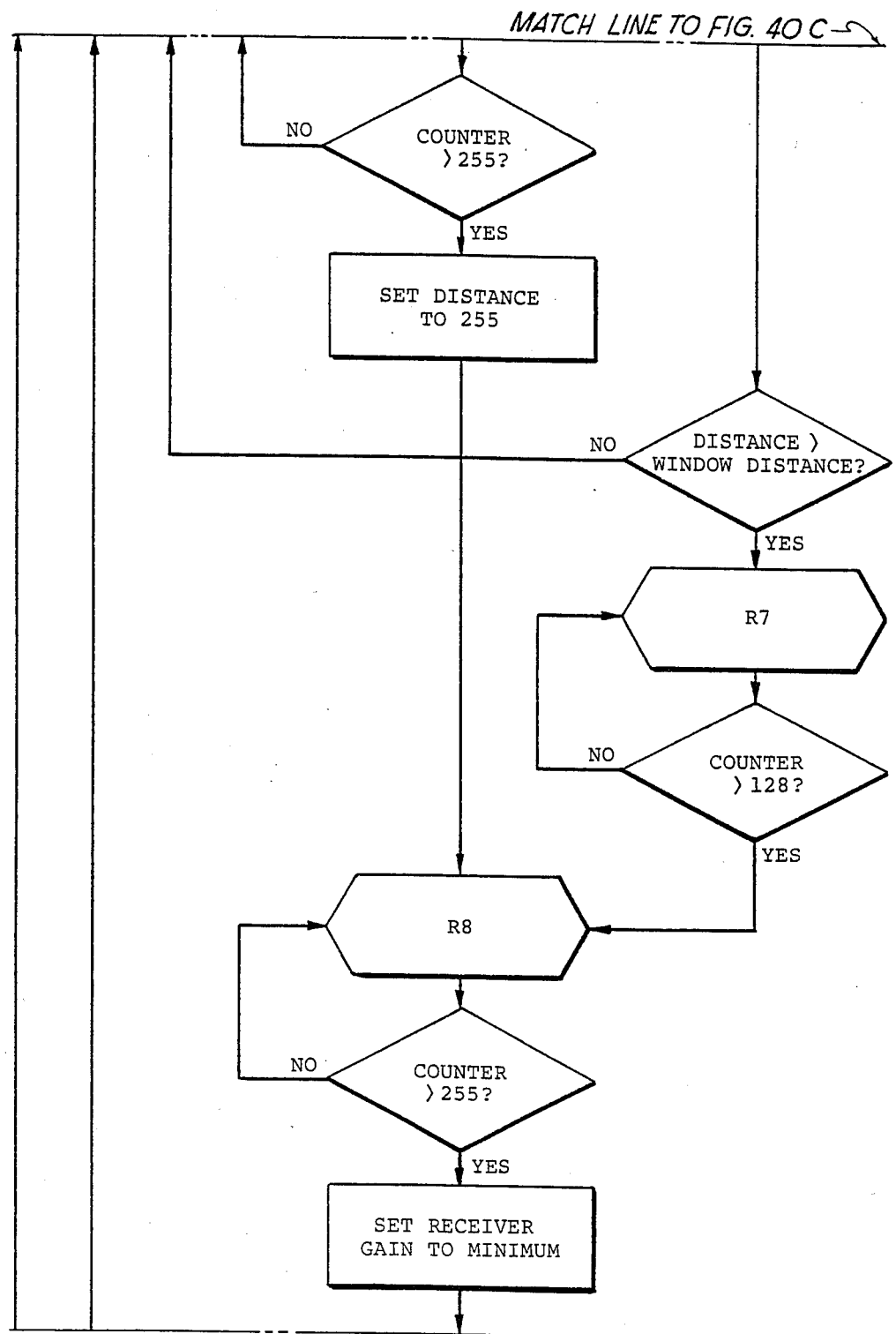
Figure 40E:
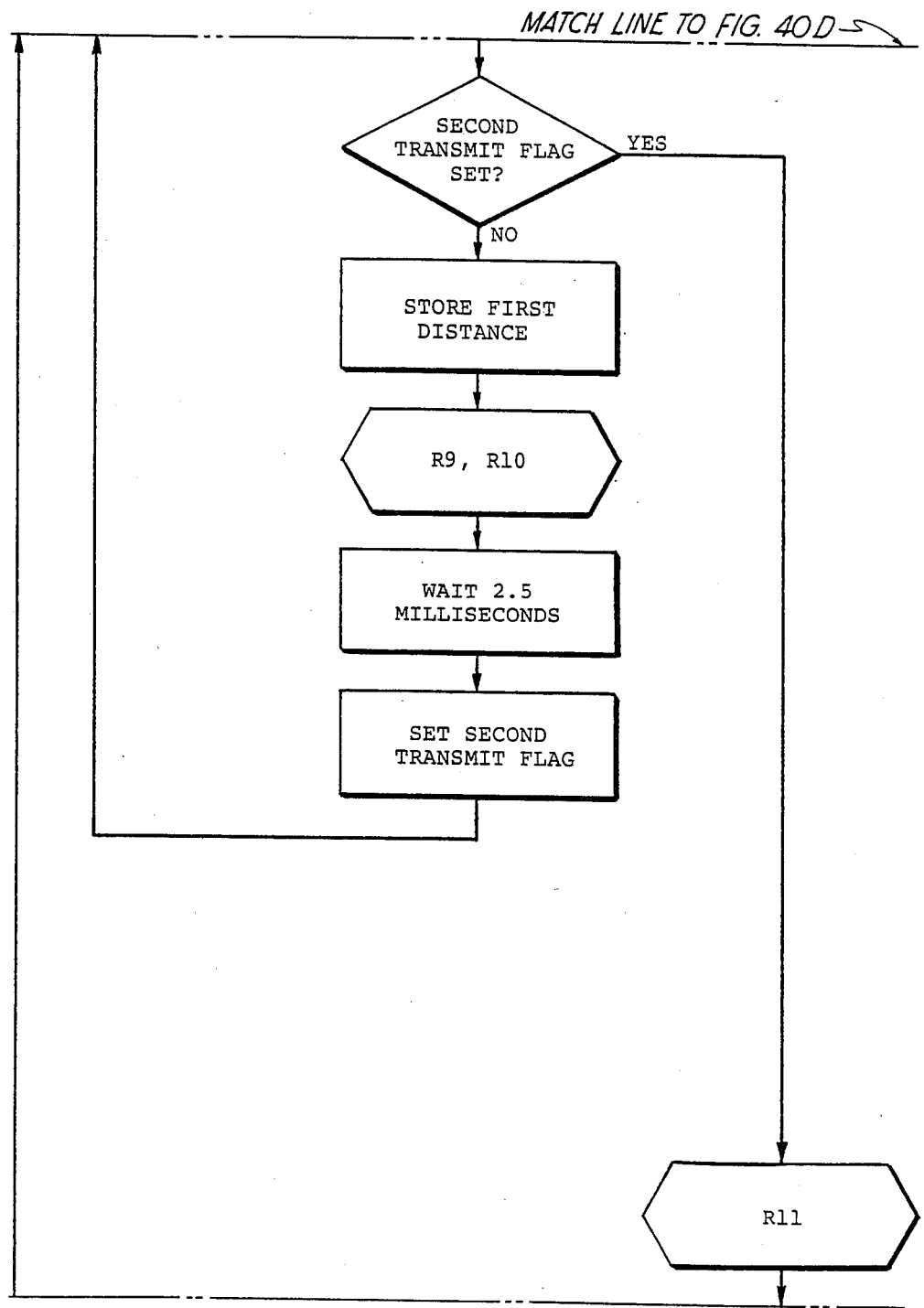
Figure 40F:
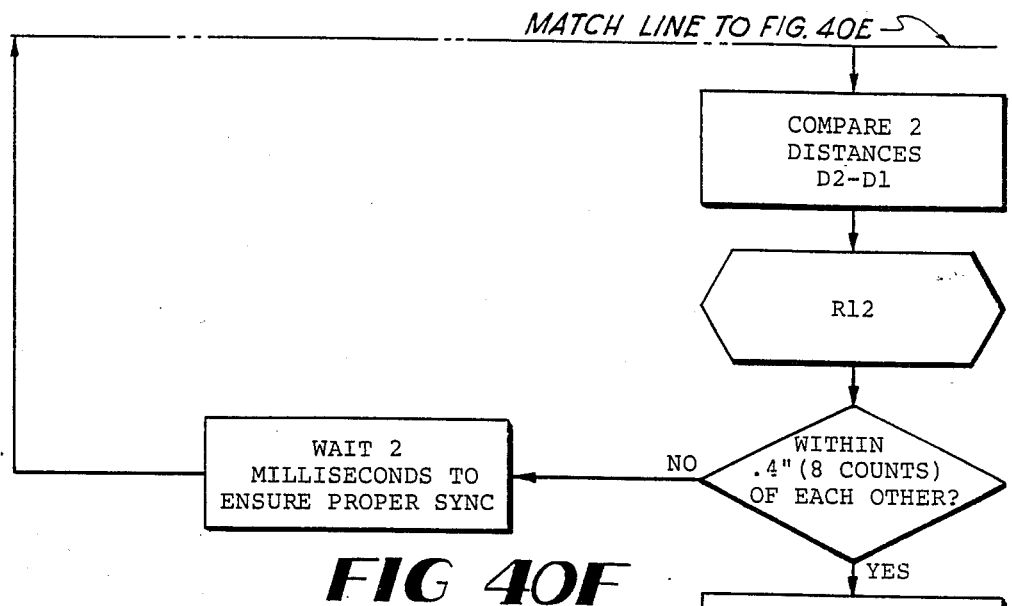
Figure 41:
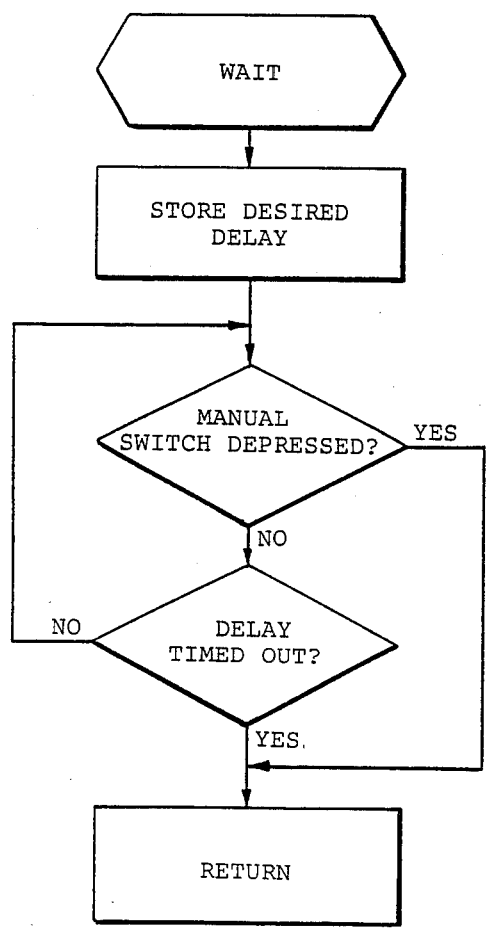
Figure 42:
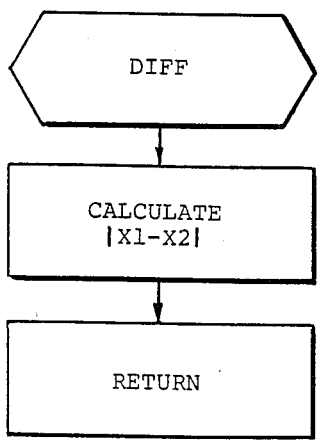
Figure 43B:
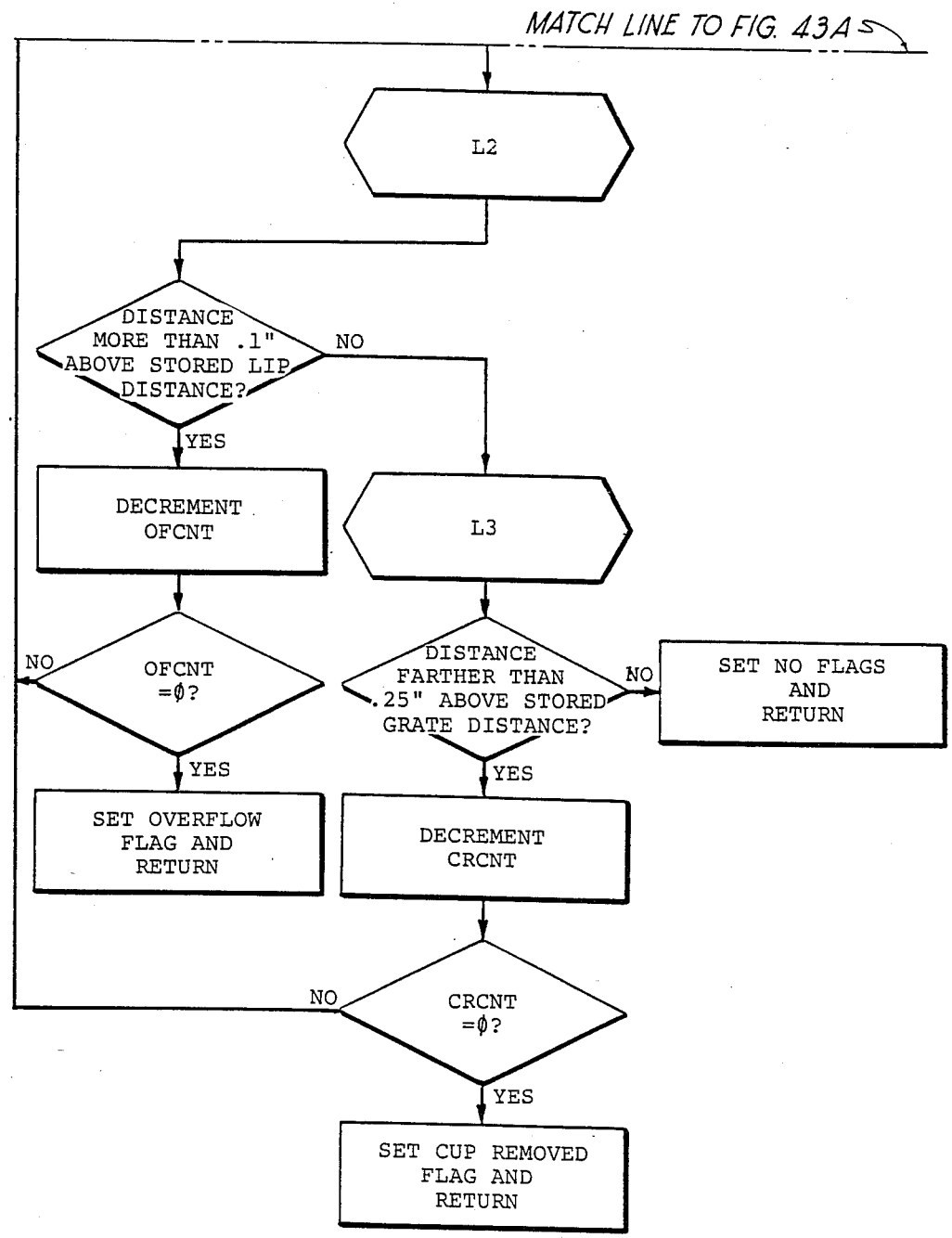
Figure 44A:
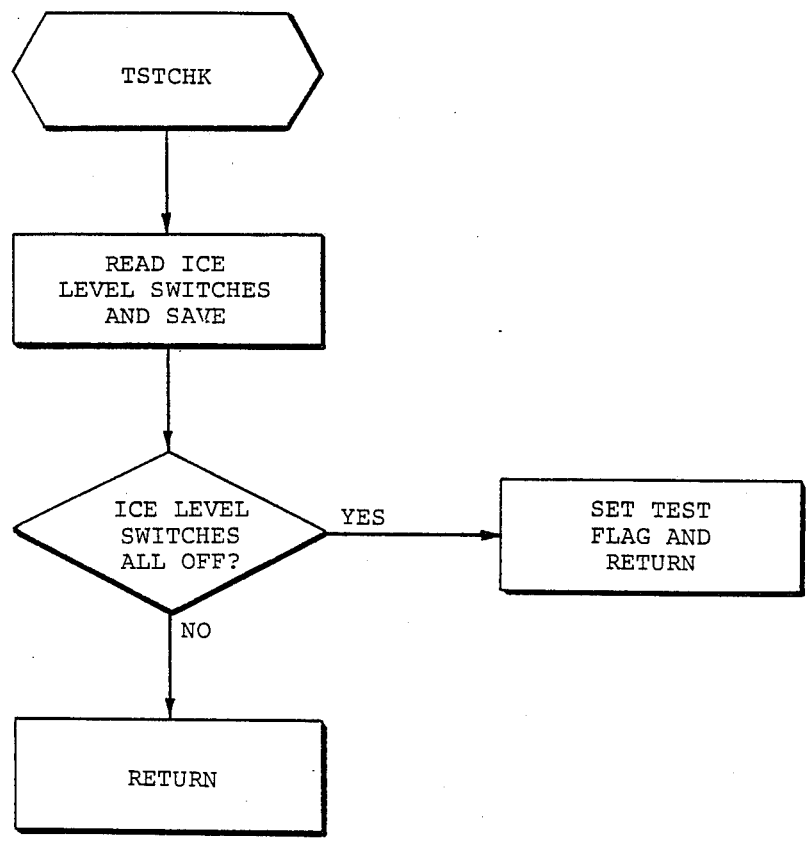
Figure 44B:
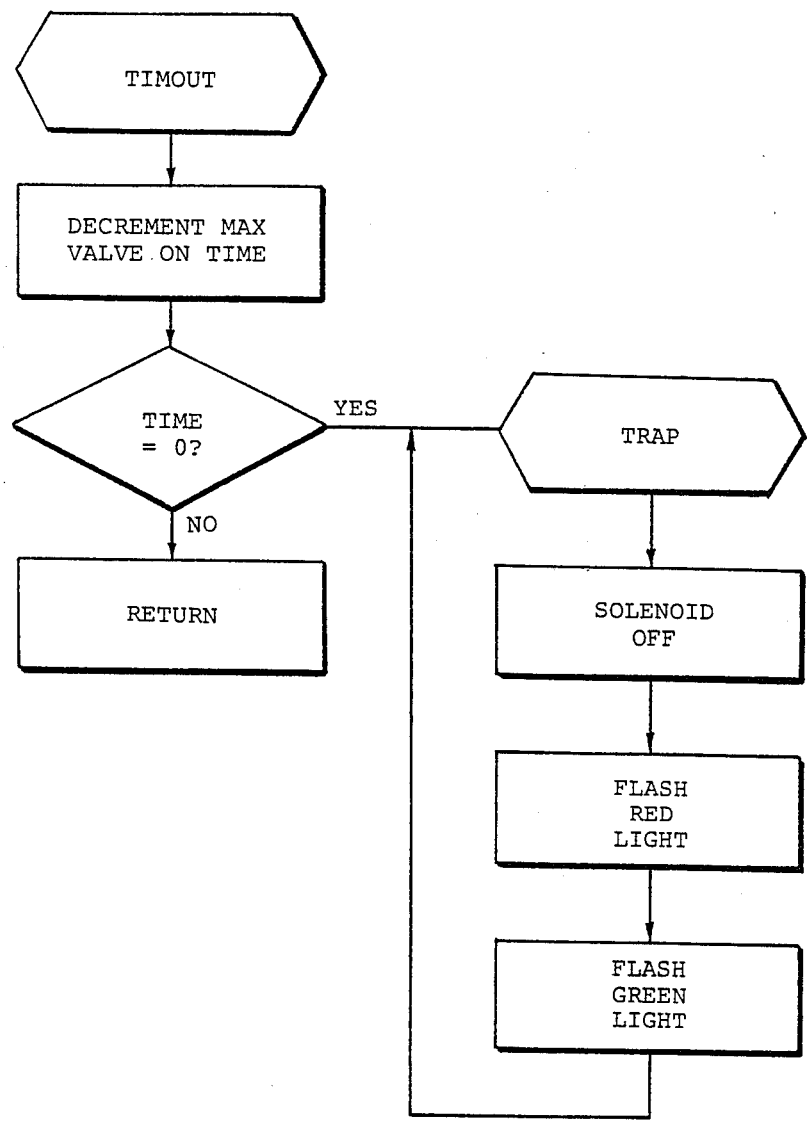

The control module 226 houses the control circuit board to which the crystals are connected by the cables 242 and 244 and the connector 248. FIGS. 31A and 31B together provide a master block diagram of the control circuit 260. The control circuit will now be described with reference to FIGS. 31–39.

The receiver transducer 262 (FIGS. 31, 32, and 33) is a 400 Khz, ½ inch diameter parallel resonant piezo-electric crystal coupled to the air by means of a plastic lens shaped to receive the beam pattern. The transducer assembly 220 incorporates a brass tube 240 that is ⅝ inch in diameter and is used for electrical isolation. The crystal is mounted such that it is centered in the tube with the lens 236 exposed at one end of the tube. The polyurethane foam provides for acoustic isolation.

The receiver section 264 (FIGS. 31, 32 and 33) has a total gain of 96 db and is comprised of two protective diodes 310 and 312 and two MC135OP IF amplifiers 314 and 316 that are interconnected through a tuned transformer 318 with another tuned transformer 320 to interconnect the second amplifier 316 to the detector 268. These amplifiers 314 and 316 have provisions for gain control from Pin 5 and are used in this application by the microcomputer 266.

The detector circuit 268 (FIGS. 31, 32 and 33) changes the 400 Khz from the receiver 264 to a DC Analog signal. This detector is special in that it can not only detect the envelope of the pulse but since it is a DC coupled detector, it has not offset shift due to pulse width variations. By having a balanced detector system, the temperature drift is very low.

The receiver gain reduction circuit 270 (FIGS. 31, 32, and 33) is comprised for five resistors that form a binary weighted current sinking "D to A" converter that is driven by the microcomputer 266, which allows for thirty-two stages of gain level control.

The threshold comparator 272 (FIGS. 31, 32, and 33) is comprised of an LM393N comparator 322 and is used in conjunction with the time varying detection to convert the analog receiver signal to a digital signal which is then fed to the microcomputer 266.

The time varying detection generator 274 (FIGS. 31, 32 and 34) uses the manual/TVD signal from the microcomputer 266 and charges a 15 Nanofarad capacitor 324 to two volts, which sets the peak level of the time varying detector wave form. This circuit is compromised of a 2N4126 switching transistor 326 and the power supply to support that circuit. 60 Hz detection is accomplished in the 60 Hz detector shown in FIGS. 31, 32 and 34. The incoming 60 Hz, 24VAC power is sensed, after filtering, by ½ of the comparator LM393N 322 and the output shunts the TVD signal to ground which, because the detector 268 signal is biased above ground, forces the detector comparator output high for ½ of the 60 Hz wave form. The microcomputer 266 senses this and uses the falling edge of the 60 Hz signal from the detector comparator to start its sequences and is thereby phase locked to the 60 Hz −24VAC power system. Adjacent valve assemblies are separated in time by reversing their 24VAC wires 450 and 452 (see FIG. 32) so that adjacent units synchronize to different ½ cycles of the 60 Hz power supply and thereby do not interfere with each other. Alternatively, a switch can be provided having two positions labeled "A" and "B" to designate the two possible orientations of the wires 450 and 452. Thus, if one valve assembly has an "A" position, each immediately adjacent valve assembly must have the switch on the "B" position. Units spaced more than one valve assembly apart are far enough apart not to interfere with each other.

The modulator 276 (FIGS. 31, 32, and 36) is comprised of a 12 volt Zener diode 328 and two transistors 330 and 332 that perform an (Anding) function for the transmitter gate signal (T) and the 400 KHz signal from the oscillator. This (Anded) signal is then level shifted through the 12 volt Zener diode 328 and the 2N4402 transistor 332 to the gate of the final amplifier 278.

The final amplifier 278 (FIGS. 31, 32, and 36) is comprised of a IRF-523 MOS-FET 334, a resistor 336 and a transformer 338. The resistor discharges the gate-source capacitor of the MOS-FET 334. The MOS-FET 334 switches the output transformer 338 to the minus 20 volt supply in response to the gate drive signal. The transformer 338 steps the voltage up to the transmitting crystal 230 to approximately 2000 volts.

The transmit transducer 280 (FIGS. 31, 32, and 36) is comprised of a 400 KHz ½ inch diameter series resonant piezo-electric crystal 30 made of PZT-5A material much the same as the receiver crystal with the exception of the thickness. The crystal 230 is coupled to the air by means of a plastic lens 232 which is also shaped to form the beam pattern. The assembly of the transmit transducer 280 is exactly the same as for the receiver as described above.

The microcomputer 266 (FIGS. 31 and 32) is a General Instruments Pic-1654 and contains the intelligence and control functions of the entire system. It communicates to the rest of the system through twelve I/O pins. It also contains the oscillator circuit, the master clear circuit, and the real time clock counter input.

The crystal 282 (FIGS. 31 and 32) and components of the 4 MHz crystal comprise passive components that form the feedback network for the oscillator in the Pic-1654.

The power-on reset circuit 284 (FIGS. 31 and 32) forms a 10 millisecond reset pulse to the microcomputer 266 at POWER-ON that allows the 4 MHz oscillator crystal 282 to start and the microcomputer 266 to become initialized.

A divide by ten counter 286 (FIGS. 31, 32, and 37) converts the 4 MHz computer clock to a 400 KHz square wave signal to operate the transmitter.

The divide by three counter 288 (FIGS. 31, 32 and 37) converts the 400 KHz signal to a 333 KHz signal that is applied to the microcomputer 266 as the real time clock counter input. Number thirteen and number fourteen are encompassed within the same IC (74HC390) divider chip which has a divide by ten and a divide by three circuit.

The front panel module 290 (FIGS. 31, 32, and 39) consists of two LED indicators 292 and 294. One is an "Over-Ice/Cup Remove" (FIGS. 31, 32, and 39) red indicator 292 and the other is a green "Fill" LED 294, indicating that the cup can be filled or is being filled. This indicator 294 remains "on" steady when a cup is ok until filling ends. In the event that there is too much ice in the cup, the Over-Ice/Cup Remove red indicator will light and stay lit until the cup is removed. If the cup is not recognized as a cup, due to mispositioning the green indicator light 294 will flash on and off.

There is a programming dip switch 296 (FIGS. 31, 32 and 38A) comprising five individual switches accessible by removing a cover (not shown) on the lower rear surface of the control module 226. One switch is used to select between a normal flow or a fast flow valve assembly, depending upon which type of valve assembly the automatic control system is being attached to. Another switch is used for selecting a foamy or flat product such as water. The other three switches are used for selecting ice level or test position. The test position is used for alignment of the receiver during manufacturing and has no field use. The binary output of the three ice level switches allows for seven ice level selections from ⅛ cup to ⅞ths cup, as illustrated in FIG. 38B.

The multiplexer circuit 298 (FIGS. 31 and 32) allows the microcomputer 266 to read either the dip switches or to set the gain of the receiver as necessary. It is comprised of five signal diodes.

The power supply 30 (FIGS. 31, 32, and 35) uses 24 volts AC from the 24 VAC transformer (not shown) in the dispenser 10. This 24 VAC is filtered to remove any high frequency noise that might interfere with the system operation. The present control system consumes less than 2 volt-amps at 24 volts AC. The 24 volts AC is rectified and filtered to form a minus 20 volt DC supply and a plus 25 volt DC supply. The minus 20 volt supply is regulated with a Zener diode and supplies power to the transmitter. The plus 25 volt supply is unregulated but has a 39 volt Zener diode used as surge protection. The 25 volt DC supply is regulated down to 15 volts for the receiver subsystem by a 78L15 three terminal regulator 340. An MPS-A06 transistor 142 is used as a flyback oscillator to provide the plus five volts needed to operate the computer circuitry. The 4.3 volt Zener diode 344 connected between the plus five volt supply and the base of a 2N4124 transistor 346 serve to regulate the fly-back oscillator.

The output switch 304 (FIGS. 31, 32, and 35) for the two solenoids of the valve assembly 212 is operated from either the microcomputer 266 or the manual push button 302 on the front of the control module 226. The resistor, opto-coupler network couples the microcomputer 266 to the Triac 349 which in turn energizes the valve solenoids in the valve 212 when either the microprocessor 266 or the manual push button 302 so requires.

The software will now be described with reference to FIGS. 40 through 46.

The software includes 4 major routines which are labeled Initialization Routine (INIT), Cup Detection (CUPDET), Fill Routine (FILL), and Cup Removal Routine (CUPREM).

The software also includes six subroutines that are defined as time delay (WAIT), absolute value of the difference of two numbers (DIFF), Grate/Overflow detector (LGRATE), Transmit/Receive, check for test mode (TSTCHK), and check for maximum value on time (TIMOUT).

The Transmitter/Receiver subroutine obtains a distance data by allowing the transmitter to operate for a period of 25 microseconds (10 cycles at 400 kHz which occupies 0.1" air space) and then monitoring the receiver output for reflections. Two Transmit/Receive periods are contained in the time period of a single half cycle of the sinusoidal line input voltage. The synchronization permits transmission only during the positive half cycle which allows two valves to operate side by side without interference by reversing the line input wires on adjacent valves. Three different entry points to the subroutine select receiver options: TBD (Transmit Bottom Detector), TBDW (Transmit Bottom Detector with Window) and TLD (Transmit Lip Detector).

The receiver has 32 steps of gain controlled by the software. The gain is set to minimum from the start of transmit to approximately 0.9" target distance time (180 microseconds). At that time, the gain is set equal to the gain variable set up in the entry point routines. For TLD, the gain is always set to maximum. For TBD and TBDW, the gain is determined by the calling routine. In TBD and TLD, the distance of the first echo detected is captured for processing. In TBDW, a lip masking window is enabled which ignores any echoes closer than the lip distance +0.35". This allows a higher gain to be used to look at liquid level rising inside the cup. Under all entry points, 2 transmissions, each separated by two milliseconds of receive time and two milliseconds of waiting for all reflections to cease, are made and the received distances stored in RAM. The processing algorithm accepts the distances if they correlate within a 0.4" and returns with the mean value as the correct distance. If the two distances do not correlate, then the routine waits on the synchronization signal and takes two new samples to correlate.

WAIT is a programmable delay subroutine that returns to the calling routine immediately if the manual push button is pressed. It has a minimum delay of 3.5 msec, and a maximum delay of 0.9 seconds.

DIFF is a subroutine that calculates the absolute value of the difference of two numbers.

LGRATE is Grate/Overflow detector subroutine used during the FILL routine to determine whether a cup has been removed or if foam or liquid has risen above the lip. The subroutine uses TLD to detect with maximum gain and no window. If TLD returns with a distance of exactly 13.7", the distance is rejected and TLD is called again. 13.7" is the maximum distance allowed by the receiver software and indicates no reflection was detected. If TLD returns with a distance less than 0.25", the overflow flag is immediately set. If TLD returns with a distance more than 0.1" closer than the stored Lip Distance for three consecutive calls to TLD, the overflow flag is set. If TLD returns a distance farther than 0.25" above the stored GRATE value for twelve consecutive calls to TLD, the cup removed flag is set. If TLD at any time returns a distance that does not meet any conditions above, the subroutine ends with no flags set.

TSTCHK (FIG. 44A) is a subroutine that reads the five position DIP (Dual Inline Package) switch. The switch positions are stored in the location in RAM labeled SWITCH. If the switches in positions 1, 2 and 3 are all off, the Test flag is set.

TIMOUT (FIG. 44B) is used whenever the solenoid valve is turned on. The subroutine decrements the "Valve on Time" register and checks to see if the value of the Register is Zero. If it is greater than zero the subroutine ends. If the value of the register is zero, the routine enters a trap loop from which there is no exit except through a hardware reset. The trap loop turns the solendid off and alternately flashes the red and green indicators.

Figure 45B:
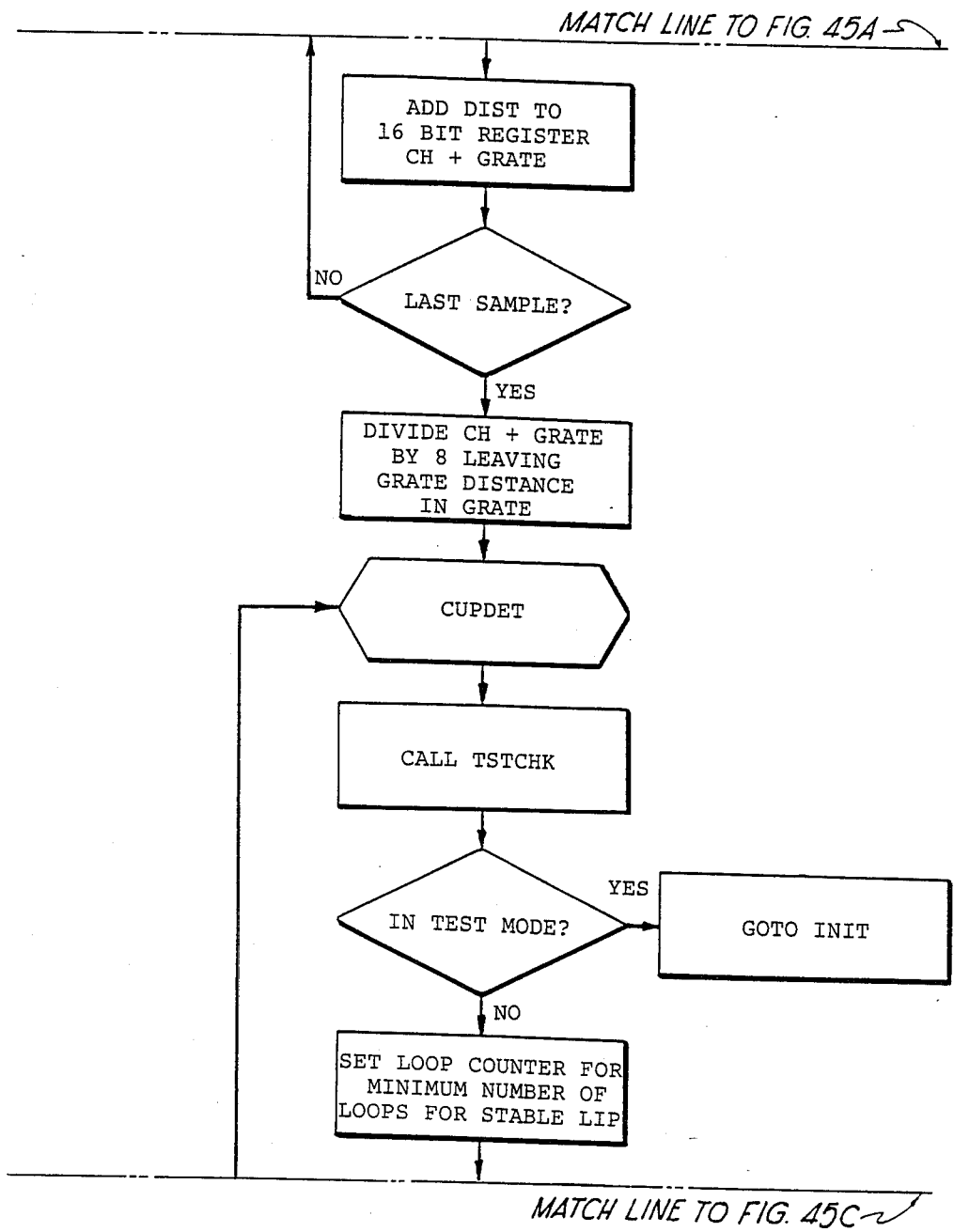
Figure 45C:
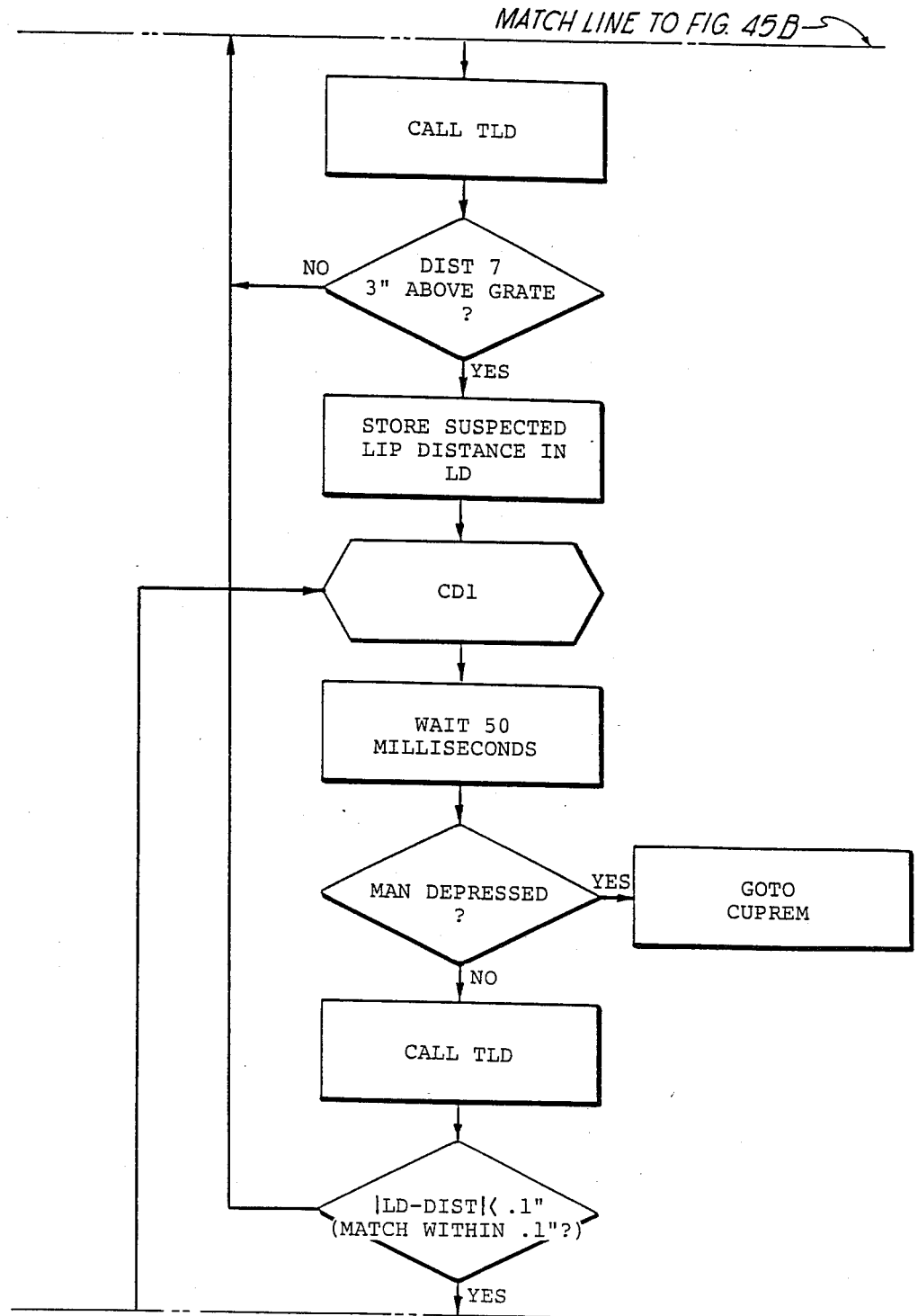
Figure 45D:
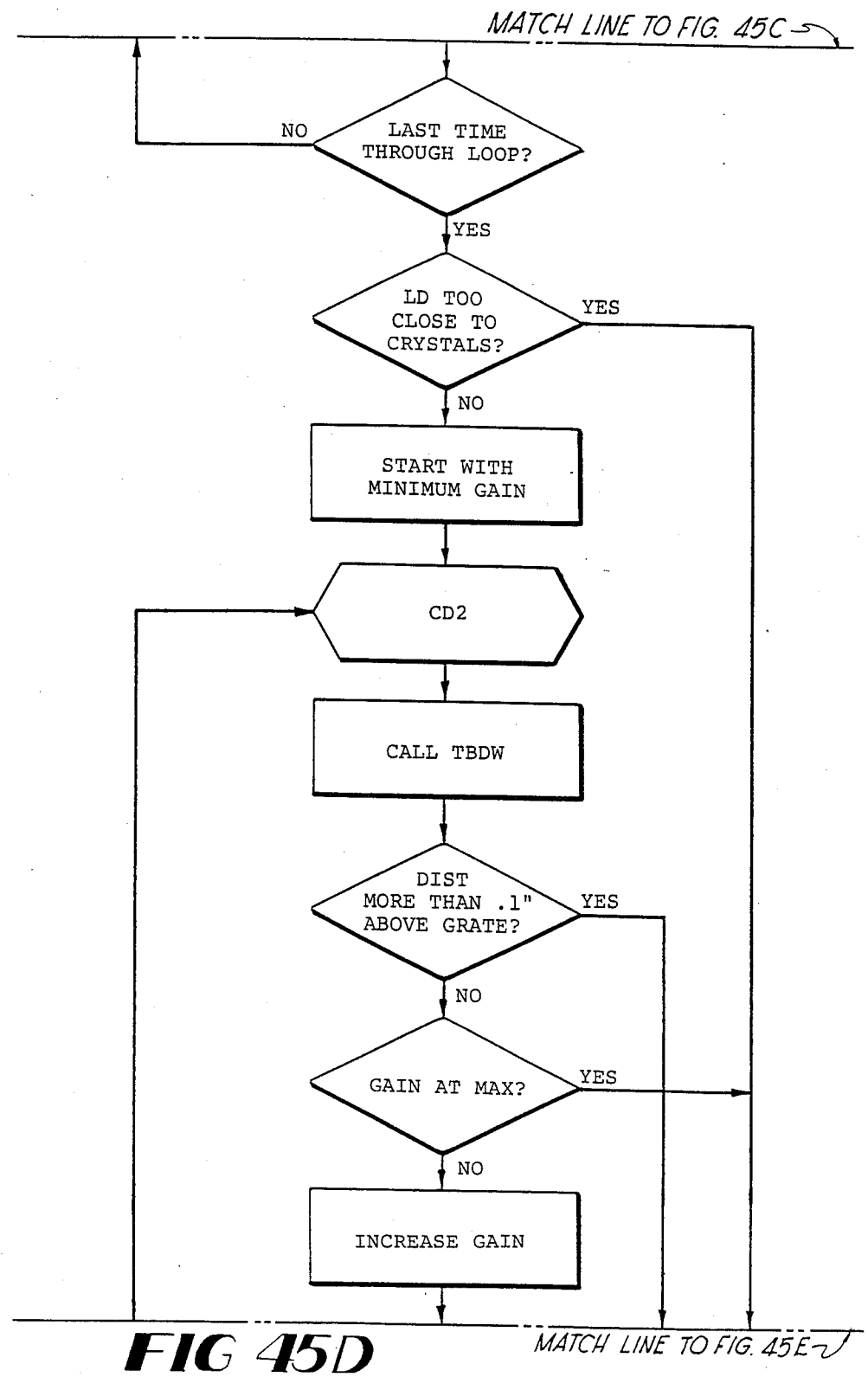
Figure 45E:
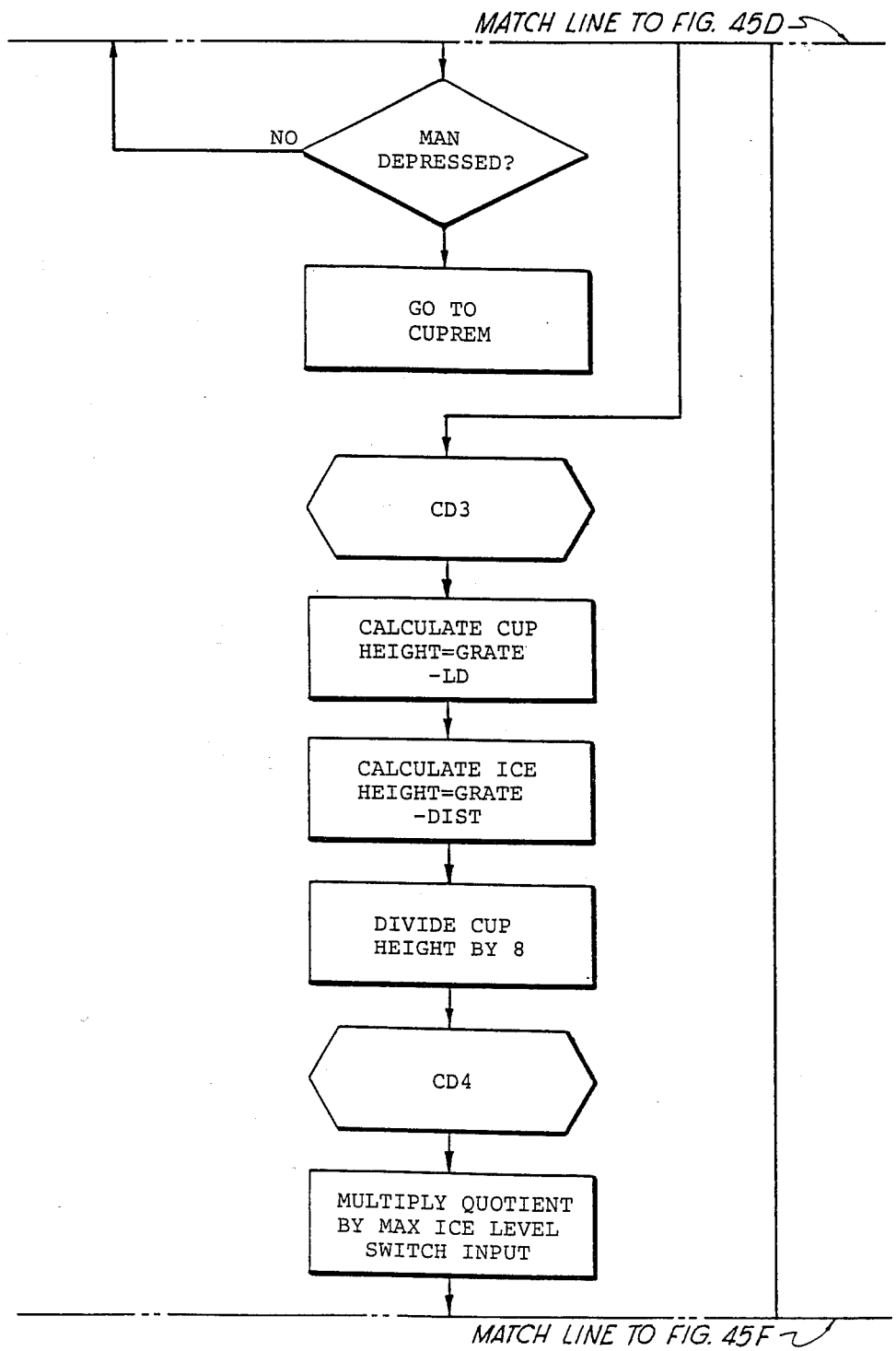
Figure 45F:
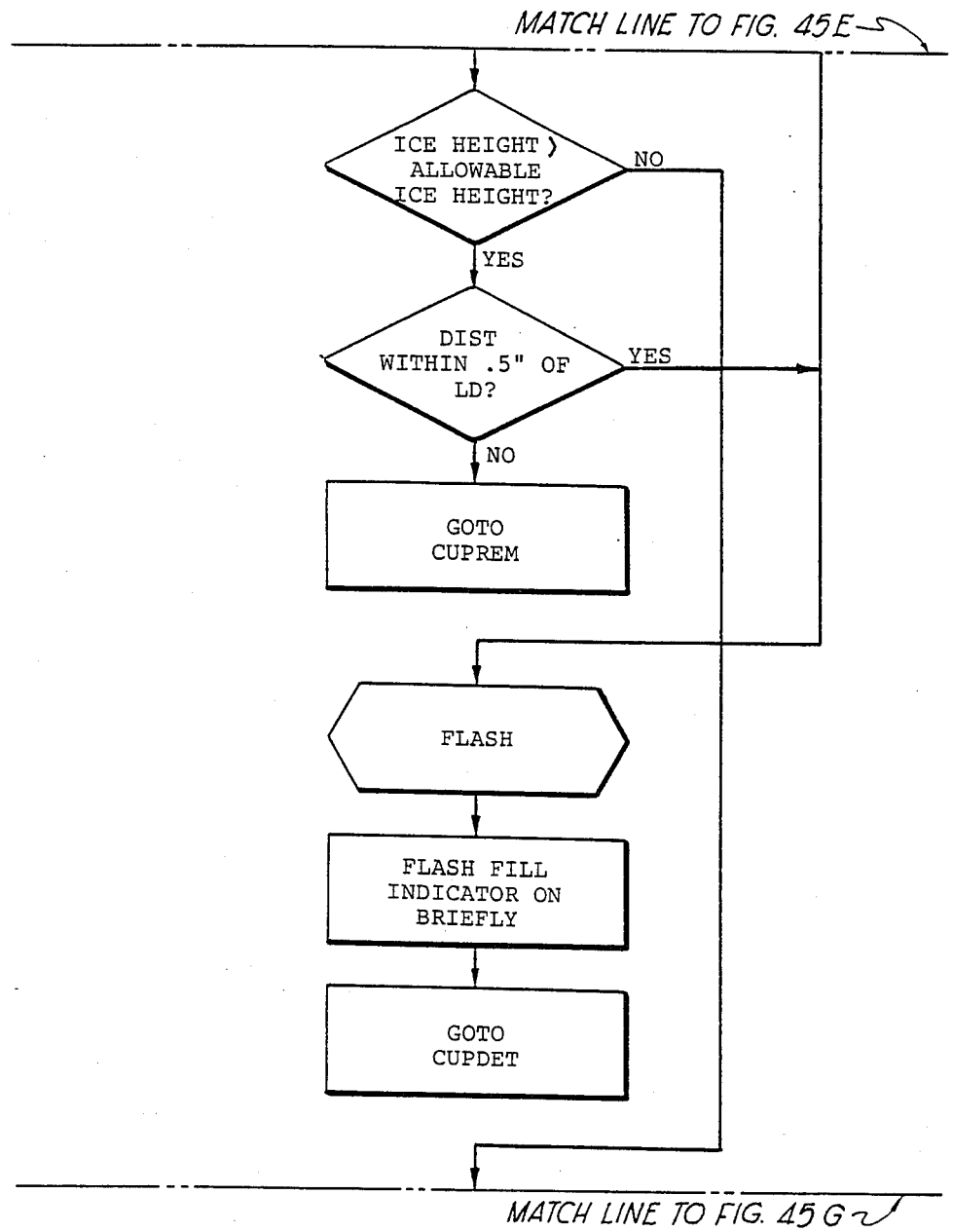
Figure 45G:
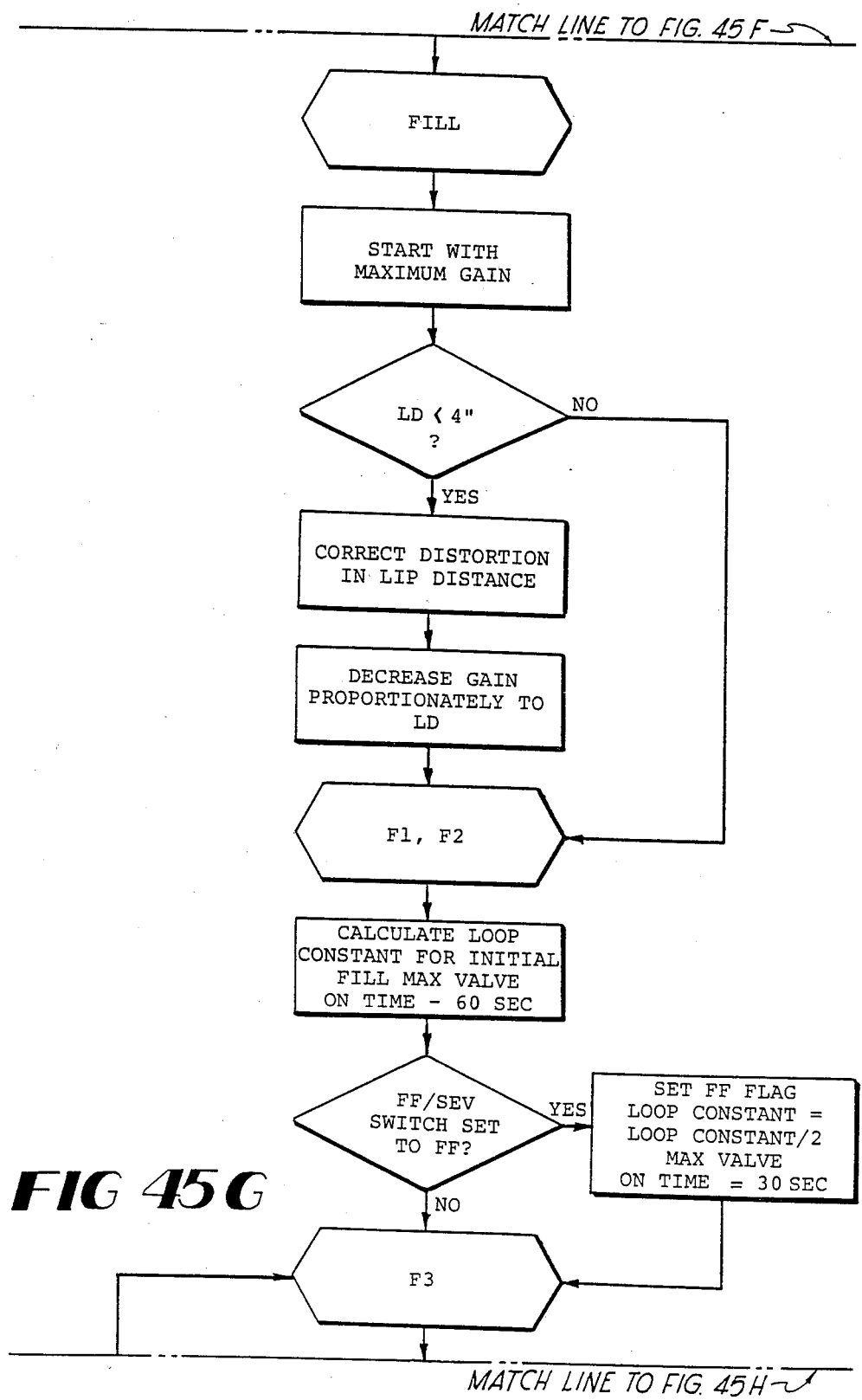
Figure 45I:
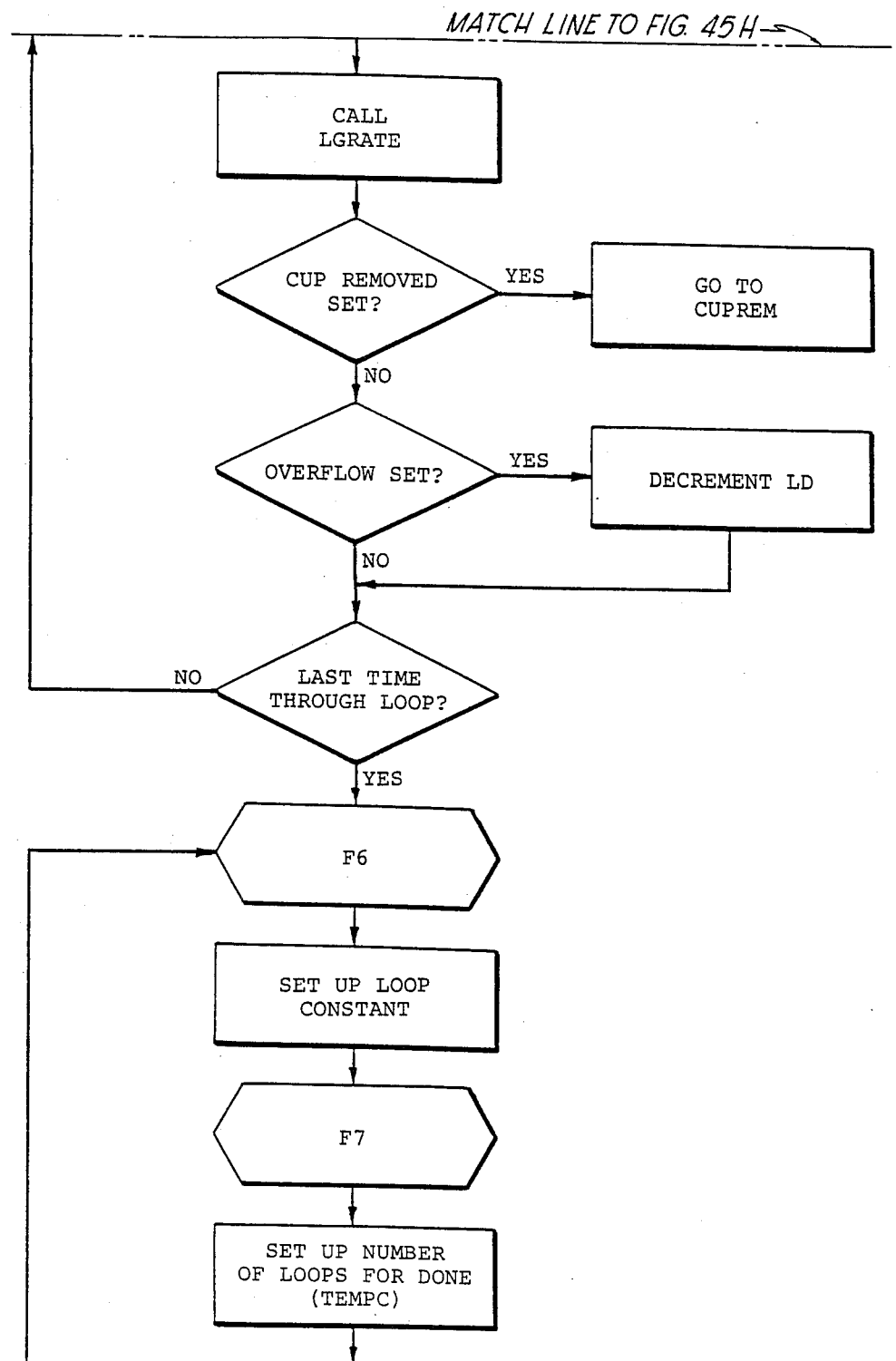
Figure 45K:
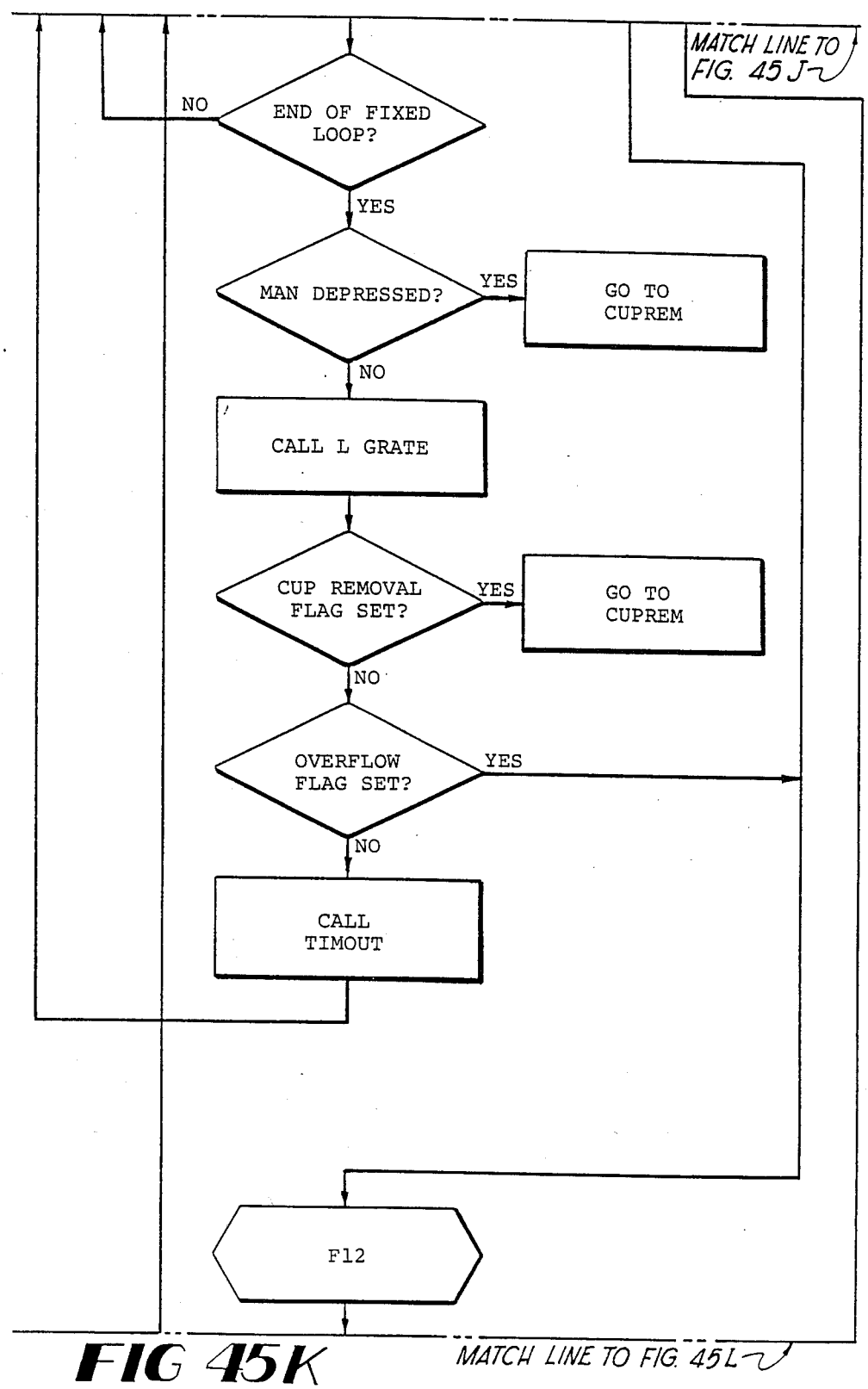
Figure 45M:
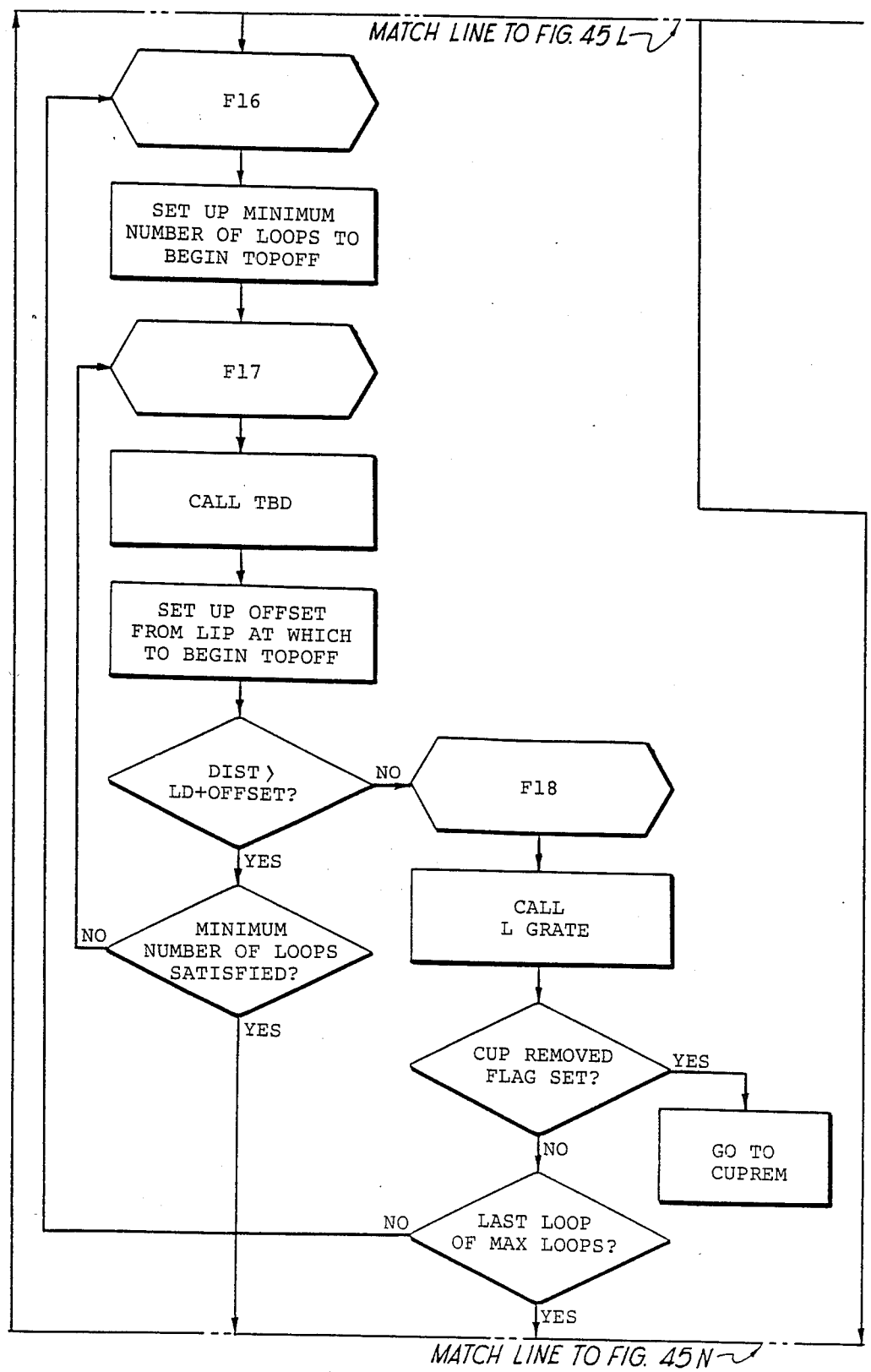
Figure 45:
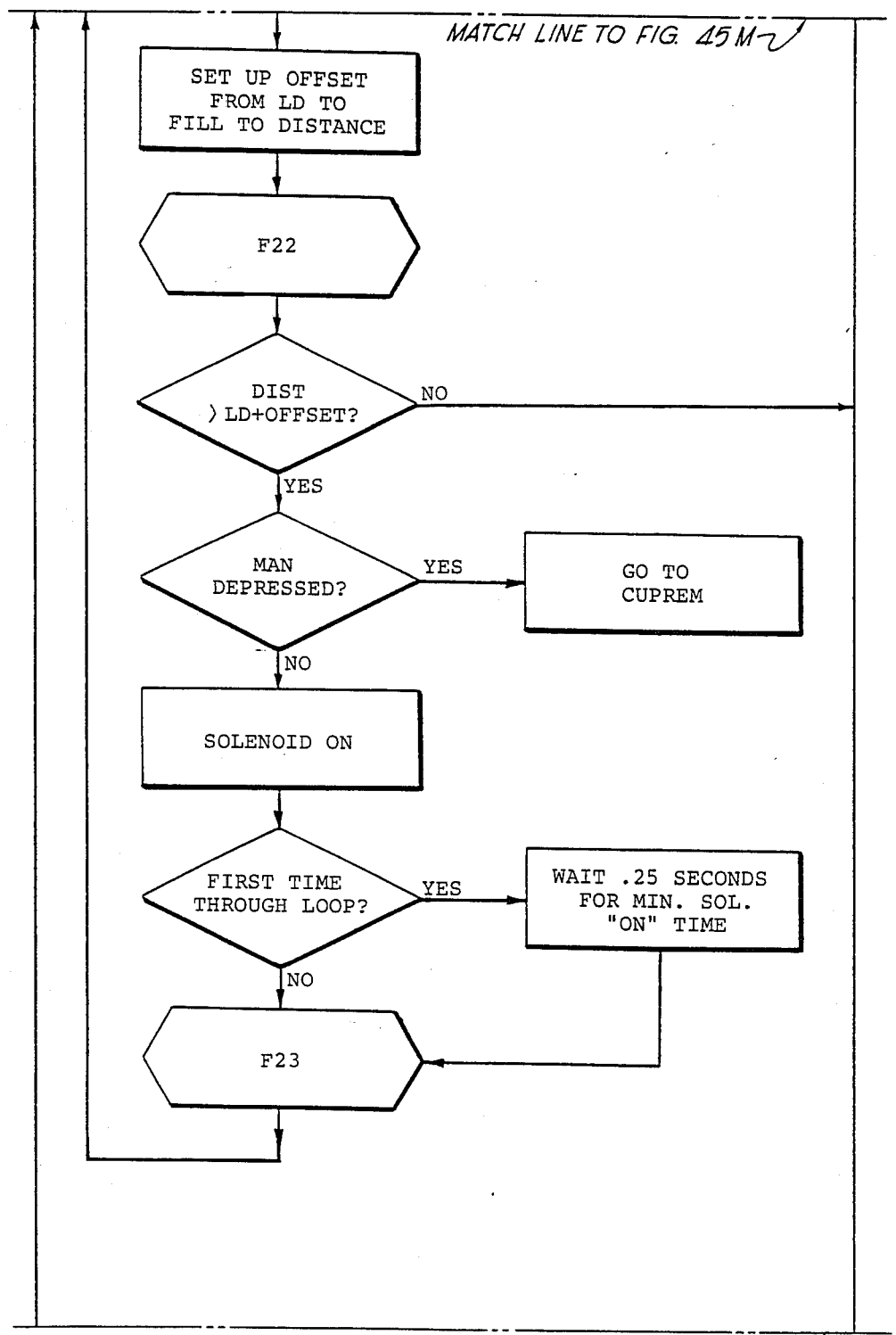
Figure 45P:
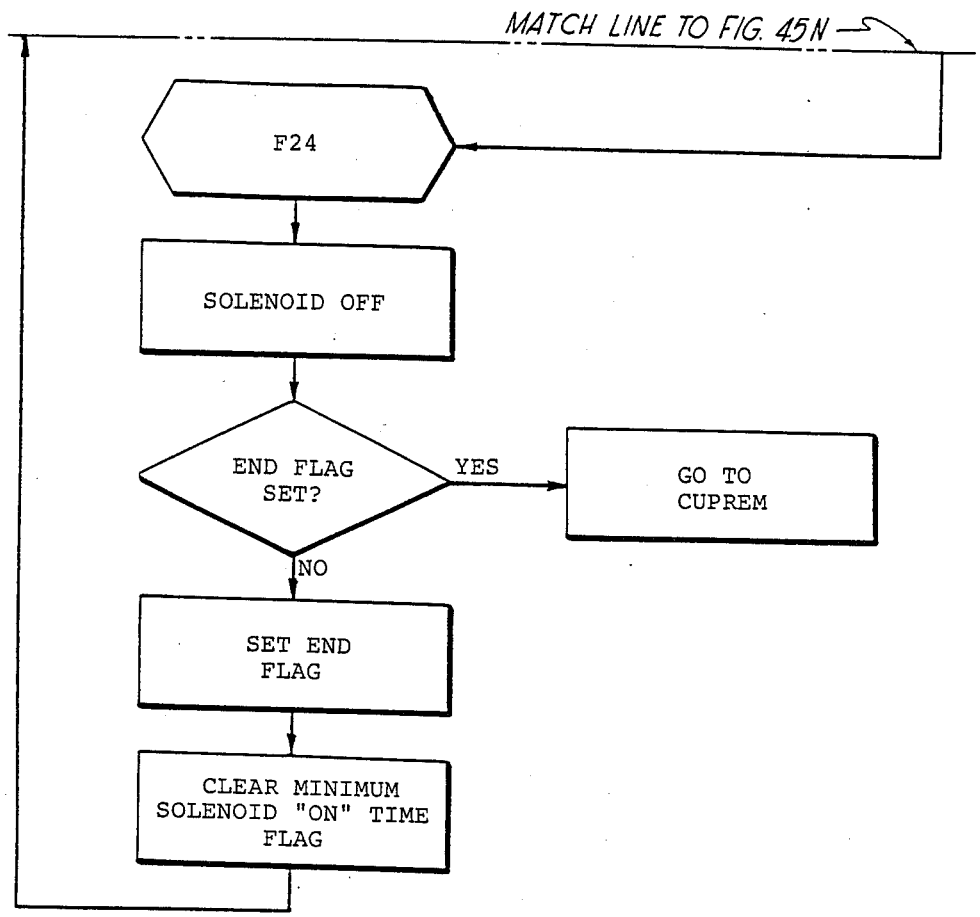
Figure 46:
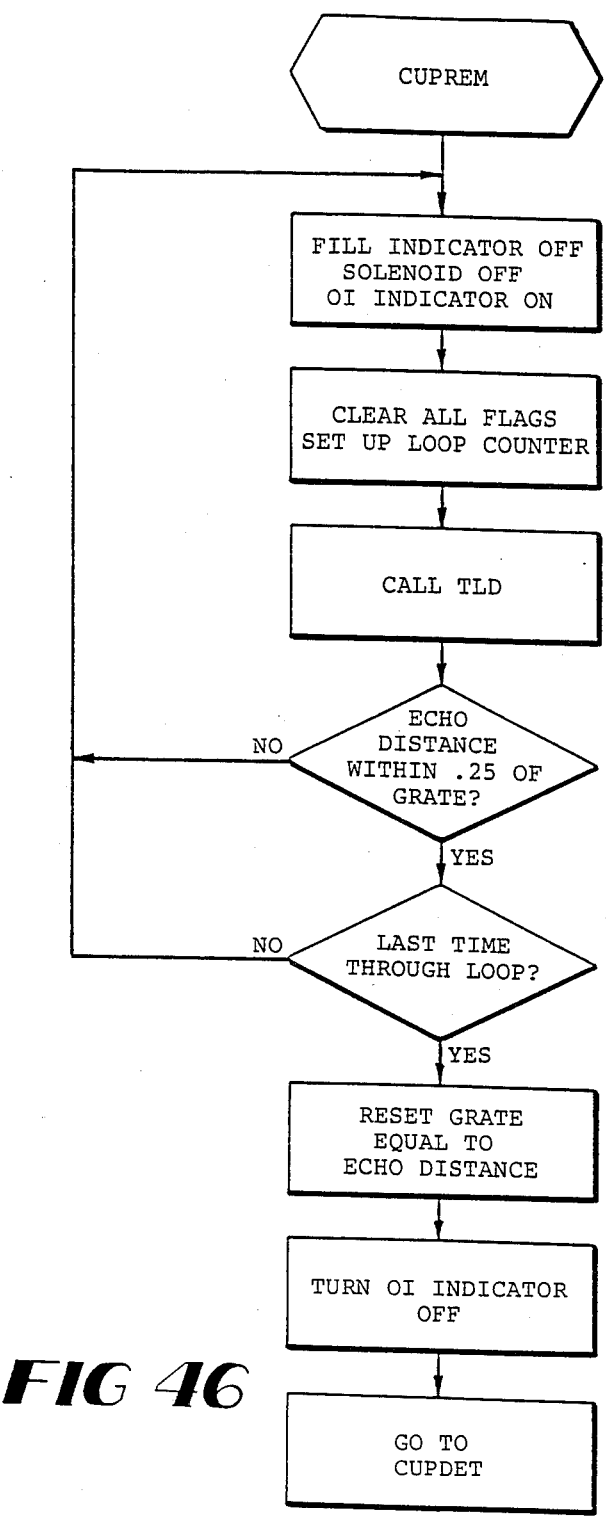

INIT (FIG. 45A) is used when the microcomputer is initialized by the "Master Clear" (hardware). During power up, the first instruction processed is set at location 777 octal. This instruction "GOTO INIT" commands the computer to begin executing this routine, which comprises the following:
a. All RAM are cleared.
b. Wait 1 second for power to stabilize.
Call TSTCHK and run the diagnostic routine if test flag is set.
d. Use TLD to look with maximum gain and no window for an echo distance between 7" and 13".
e. If it does not detect an echo within this range, the "Over Ice" indicator on the front panel flashes.
f. If it does detect an echo distance within 7" to 13", an average of 8 samples is stored in RAM as the Grate distance and the program continues at CUPDET.

CUPDET is the Cup Detection routine. This routine collects data using TLD and accepts a cup using the following procedure:
a. The manual fill switch on the front panel is monitored continuously to assure proper operation. If the manual switch is pressed, the computer begins the Cup Removal routine immediately. The DIP switch is read by calling TSTCHK and if the test flag is set, the CUPDET routine ends and the INIT routine begins.
b. A stable lip distance must be established more than 3" above the GRATE. A stable lip distance is defined as 5 consecutive echo distances from TLD separated by 60 milliseconds that correlate within 0.1". This corresponds to the cup lip being stable for 330 milliseconds. If the stable lip distance is too close to the crystals (0.6"), the Lip Distance is rejected, the FILL indicator flashes and CUPDET begins again.
c. A cup bottom or ice level must be discerned that is more than 0.1" above the Grate and more than 0.5" below the lip. This is accomplished using TBDW and varying the gain as follows: With minimum gain, obtain an echo distance using TBDW. If the echo distance is not more than 0.1" closer than the grate, then the gain is increased one step and another sample is taken. If the gain reaches the maximum, the FILL indicator flashes and the Cup Detection routine begins again.
d. The Ice/Bottom height is calculated from the last distance obtained as outlined in (C) above and the GRATE and then stored as the actual ice height. The cup height is calculated from the lip distance and the GRATE. The cup height is divided by 8 and the quotient is multiplied by the 3 bit binary number input as selected on the ice level programming switches. This allowable ice height is compared to the actual ice height and the Lip Distance. If the actual ice height is greater than allowed by the switch selection, but less than 0.5" below the Lip Distance, the cup is rejected and the Cup Removal routine begins. If the actual ice height is within 0.5" of the Lip Distance, the cup is not positioned correctly and the FILL indicator flashes before begining the Cup Detection routine again. If the actual ice height is less than the level selected by the switch, the FILL routine begins.

The FILL routine controls the complete filling and top off operation. The routine limits the solenoid operation to a maximum of 3 On/Off cycles. After each of the first 2 cycles, the routine waits for the foam to settle before starting the next cycle. When the cup is full, the Cup Removal routine begins. If the manual switch is pressed at anytime during the FILL routine, the Cup Removal routine begins immediately. The timout subroutine is called during the time the solendid valve is turned on by the fill program to monitor the valve on time. If the maximum valve on time is exceeded, the timeout subroutine turns the valve off and does not return on the fill routine. A detailed description of the FILL routine follows:
a. Before the solenoid is actuated, several checks and corrections are made. The gain is initially set at maximum. If the Lip Distance is less than 4", the gain is adjusted with the empirically derived equation:

Gain=Gain−⅛ (4"−lip distance)

If the Lip Distance is less than 4", the Lip Distance is adjusted with the empirically derived equation:

Lip Distance=Lip Distance−⅛ (4"−Lip Distance)

The Time Constant for this particular cup height is calculated with the equation:

Time Constant=cup height/4 for SEV and cup height/8 for Fast Flow.

This Time Constant is used in the first of the three cycles to provide an initial fill time proportional to the cup height.
b. The gain must be adjusted such that the fluid level is detected and the lip is not during the period when the cup vibrates such as at the beginning of a FILL. Also if the cup was not positioned perfectly, the Lip Distance may be slightly farther than originally detected. To adjust the gain, an initial filling period proportional to cup height is allowed to minimize cup vibration and adjust gain as necessary. During this time period the routine uses TBD to check if the echo distance is within 0.75" of the stored Lip Distance. If it is, the gain is reduced one step. If the gain reaches minimum, the Cup Removal routine begins. This time is also used to adjust the Lip Distance as follows: LGRATE is called and if an overflow is detected then the Lip Distance is decremented (an overflow in LGRATE is defined as more than 0.1" less than the stored Lip Distance). If LGRATE detects a missing cup then the Cup Removal routine begins immediately. At the end of this period, the solenoid valve stays on.
c. During the next time period the routine uses TBDW to monitor the liquid level. If the Foamy/Flat switch is set to Foamy, the solenoid turns off when the liquid level is within 0.5" for SEV or 0.7" for FFV. If the Foamy/Flat switch is set to Flat, the solenoid is not turned off until the liquid level reaches 0.2" for SEV and 0.3" for FFV, at which time the cup removal routine begins. This condition must be met in two consecutive checks for the solenoid to turn off. The Grate/Overflow detector subroutine checks to see if the cup has been removed or if TBDW has missed the liquid level rising and an overflow is imminent. If the cup is missing, the cup removal routine begins. If there is an overflow indicated, the solenoid is turned off.
d. A 4-second pause begins at this time to allow the foam to settle. The Grate/Overflow subroutine checks continuously for the cup to be removed. If it is, the cup removal routine begins immediately.

e. After the pause, another 4-second time period starts. Using TBD, the foam level is monitored. If the foam drops below 0.4" for 10 consecutive checks, this period ends and the first top-off period begins. If the foam does not drop below 0.4" within 4 seconds, the first top-off period begins anyway. The Grate/Overflow subroutine continuously checks for a missing cup. If a missing cup is detected, the cup removal routine begins.

f. The first top-off cycle uses TBD to determine if the liquid/foam level is within 0.1" for a normal 1½ ounces per second valve assembly and 0.05 for the faster 3 ounces per second valve assemblies. If this condition exists, the solenoid is not turned on and this cycle ends. If not, then the solenoid is turned on until the condition is met. For stability, the solenoid has a minimum on time of 0.25 seconds.

g. A repeat of "D", "E", and "F" occurs now to implement the second top-off cycle with the exception that in "F" the values are 0.2" for the normal 1½ ounces per second valve assembly and 0.3" for the faster 3 ounces per second valve assembly. The cup removal routine (CUPREM) turns the fill indicator off, the solenoid off, and the Over-Ice indicator on. It uses TLD and waits for an echo distance within 0.25" of the Grate. When this condition exists, a new Grate distance is stored, the Over-Ice indicator turns off, and the Cup Detection routine begins again.

While the preferred embodiments of this invention have been described above in detail, it is to be understood that variations and modifications can be made therein without departing from the spirit and scope of the present invention as set forth in the appended claims. For example, other materials can be used for the crystals and the lenses and other numbers of crystals can be used and other arrangements and locations can be used for the two crystals of the transducer assembly. In addition, a different ultrasonic transmitter and receiver can be used in place of the crystals, if desired, such as various ultrasonic foil devices. While two specific control circuits have been described in detail, other control circuits and other components thereof can be used. While a microcomputer has been described and is preferred, the control circuit can alternatively use a micropocessor connected to a remote RAM and ROM, for example. While the transducer assembly and the control module are shown attached to the dispenser valve assembly, this is not essential; they can be attached to the dispenser and just connected electrically to the valve assembly.

What is claimed is:

1. A transducer assembly for use in the ultrasonic automatic filling of a container with a beverage comprising:
   (a) a housing;
   (b) an ultrasonic transmitter crystal having a first lens connected to its lower surface for both coupling the transmitter crystal to air and being lens shaped for producing a shaped beam of ultrasonic energy from said transmitter crystal;
   (c) a separate ultrasonic receiver crystal having a second lens connected to its lower surface for both coupling the receiver crystal to air and being lens shaped for providing that the receiver crystal will receive a beam of ultrasonic energy from a predetermined area;
   (d) said transmitter crystal and first lens being located within but not touching a first non-ferrous metal tube;
   (e) said receiver crystal and second lens being located within but not touching a second non-ferrous metal tube;
   (f) said first and second metal tubes being located within said housing; and
   (g) polyurethane foam substantially filling the remaining space within said housing and within said tubes and holding said tubes and said crystals in place therein.

2. The assembly as recited in claim 1 including first and second electrical wires extending from the top of said assembly out of said foam, said first wire including first and second leads each being connected to a metal plating on opposite surfaces of said transmitter crystal and a third lead connected to said first metal tube, said second wire including first and second leads each being connected to a metal plating on opposite surfaces of said receiver crystal and a third wire connected to said second tube.

3. The assembly as recited in claim 1 wherein said lens is shaped to produce a beam having a footprint at twelve inclhes that is about three fourths of an inch wide and about two and one-half inches long.

4. The assembly as recited in claim 1 wherein said crystals are ceramic crystals made of one of PZT-4 or PZT-5a material and said lenses are made of one of ABS or acrylic plastic.

5. The assembly as recited in claim 1 wherein each of said lenses is glued to the respective one of said crystals.

6. The assembly as recited in claim 1 wherein said crystals and lenses are circular discs about 1½ inch in diameter.

7. The assembly as recited in claim 1 including ultrasonic energy absorbing walls extending downwardly below said transmitter crystal to absorb ultrasonic energy transmitted toward said walls.

8. The assembly as recited in claim 1 wherein each of said crystals is recessed into a cavity in a lower surface of said foam.

* * * * *

UNITED STATES PATENT AND TRADEMARK OFFICE
CERTIFICATE OF CORRECTION

PATENT NO. : 4,780,861

DATED : Oct. 25, 1988

INVENTOR(S) : William F. Stembridge et al.

It is certified that error appears in the above-identified patent and that said Letters Patent is hereby corrected as shown below:

Column 22, line 40:

In claim 3, line 3, delete "inclhes" and insert therefor --inches--.

Column 22, line 49:

In claim 6, line 2, delete "1½" and insert therefor --½--.

Signed and Sealed this

Third Day of March, 1992

Attest:

HARRY F. MANBECK, JR.

*Attesting Officer*  *Commissioner of Patents and Trademarks*